(12) United States Patent
Bakre et al.

(10) Patent No.: US 8,460,928 B2
(45) Date of Patent: Jun. 11, 2013

(54) METHODS OF SPECIFYING MESODERMAL, ENDODERMAL AND MESOENDODERMAL CELL FATES

(75) Inventors: Manjiri M. Bakre, Genome (SG); Lawrence W. Stanton, Genome (SG)

(73) Assignee: Agency for Science, Technology and Research, Centros (SG)

( * ) Notice: Subject to any disclaimer, the term of this patent is extended or adjusted under 35 U.S.C. 154(b) by 887 days.

(21) Appl. No.: 12/091,210

(22) PCT Filed: Oct. 25, 2006

(86) PCT No.: PCT/SG2006/000313
§ 371 (c)(1),
(2), (4) Date: Oct. 29, 2008

(87) PCT Pub. No.: WO2007/050043
PCT Pub. Date: May 3, 2007

(65) Prior Publication Data
US 2009/0304642 A1    Dec. 10, 2009

Related U.S. Application Data

(60) Provisional application No. 60/729,666, filed on Oct. 24, 2005.

(51) Int. Cl.
*C12N 5/0735* (2010.01)

(52) U.S. Cl.
USPC .......................... 435/377; 435/375; 435/366

(58) Field of Classification Search
USPC .......................... 435/366, 375, 377
See application file for complete search history.

(56) References Cited

FOREIGN PATENT DOCUMENTS
WO    2005/063971    7/2005

OTHER PUBLICATIONS

Haegele et al. Wnt signalling inhibits neural differentiation of embryonic stem cells by controlling bone morphogenetic protein expression. Molecular and Cellular Neuroscience 24 (2003) 696-708.*
Pera et al. 2004. Regulation of human embryonic stem cell differentiation by BMP-2 and its antagonist noggin. Journal of Cell Science 117 (7); 1269-1280.*
St-Onge et al. Pax6 is required for differentiation of glucagon-producing a-cells in mouse pancreas. Nature vol. 387 1997. p. 406-409.*
Maschhoff et al. Conservation of Sox4 gene structure and expression during chicken embryogenesis. Gene 320 (2003) 23-30.*
Wiese et al. Nestin expression—a property of multi-lineage progenitor cells? CMLS, Cell. Mol. Life Sci. 61 (2004) 2510-2522.*
Dravid, G. et al., "Defining the role of Wnt/beta-catenin signaling in the survival, proliferation, and self-renewal of human embryonic stem cells," Stem Cells, 23(10):1489-1501 (2005).
Kobayashi, T. et al., "Wnt4-transformed mouse embryonic stem cells differentiate into renal tubular cells," Biochemical and Biophysical Research Communications, Academic Press Inc., Orlando, FL, US; vol. 336(2):585-595 (2005).
Lako, M. et al., "Characterisation of Wnt gene expression during the differentiation of murine embryonic stem cells in vitro: role of Wnt3 in enhancing haemtopoietic differentiation," Mechanisms of Development, Elsevier Science Ireland LTD, IE, vol. 103:49-59 (2001).
Otero, J.J. et al., "Beta-catenin signaling is required for neural differentiation of embryonic stem cells," Development (Cambridge), vol. 131(15):3545-3557 (2004).
Sato, N. et al., "Maintenance of pluripotency in human and mouse embryonic stem cells through activation of Wnt signaling by a pharmacological GSK-3-specific inhibitor," Nature Medicine, Nature Publishing Group, New York, NY, US; vol. 10(1):55-63 (2003).
Terami, H. et al., "Wnt11 facilitates embryonic stem cell differentiation to Nkx2.5-positive cardiomyocytes," Biochemical and Biophysical Research Communications, Academic Press Inc., Orlando, Fl, US; vol. 325(3):968-975 (2004).

* cited by examiner

*Primary Examiner* — Taeyoon Kim
(74) *Attorney, Agent, or Firm* — Wilmer Cutler Pickering Hale and Dorr LLP

(57) ABSTRACT

We disclose a method for producing a mesodermal or a endodermal cell from a pluripotent stem cell, the method comprising activating a Wnt signalling pathway in the pluripotent stem cell. In some embodiments, the pluripotent stem cell is in a substantially 2 dimensional configuration, such as a monolayer, for at least a portion of the time when the Wnt signalling pathway is activated.

14 Claims, 28 Drawing Sheets

*** Active β-catenin

E14 Control (Day14)   E14 + Wnt3A (Day 14)   E14 + 1µM iGSK-3β (Day 14)

H1 Control (Day 15)

H1 + Wnt3A (Day 15)

H1 + 2µM iGSK-3β

H1 Control (Day 21)

H1 + Wnt3A (Day 21)

H1+ iGSK-3β (Day 21)

BIO: R = H
MeBIO: R = CH3

No Primary Ab control

Pitx2 Ab

T-brachyury

METHODS OF SPECIFYING MESODERMAL, ENDODERMAL AND MESOENDODERMAL CELL FATES

CROSS-REFERENCE TO RELATED APPLICATIONS

This application is a 371 National Stage of International Application No. PCT/SG2006/000313 filed on Oct. 25, 2006, which designates the United States, and which claims the benefit under 35 U.S.C. §119(e) of U.S. Provisional Application No. 60/729,666 filed on Oct. 24, 2005, the entire contents of which are incorporated herein by reference.

BACKGROUND

During early embryogenesis, the embryo is divided into two major lineages: the pluripotent inner cell mass and the trophoblast. The pluripotent inner cell mass subsequently generates all three germ layers, which are capable of further differentiation into terminally differentiated tissue specific cells.

Embryonic stem cells are self-renewing cells derived from the inner cell mass of the embryo at the blastocyst stage and the embryonic stem cells possess the potential to differentiate into any one of the three germ lineages (i.e., are pluripotent). The pluripotent stem cells have practical applications in clinical settings such as in the areas of regenerative medicine and chemotherapy.

There is a need in the art for methods and compositions that are capable of modulating the development of pluripotent stem cells, specifically the differentiation of pluripotent stem cells along a specific preferred lineage.

The evolutionary conserved Wnt signalling pathway controls many events in embryogenesis and also has a central role in tumorigenesis. The Wnt signalling pathway is a signalling cascade of a collection of proteins which regulates the phosphorylation and degradation of $\beta$-catenin, thereby regulating expression of $\beta$-catenin-dependent genes.

The Wnt genes belong to a family of proto-oncogenes expressed in several species ranging from invertebrates to vertebrates. These genes encode over twenty cysteine-rich, secreted glycoproteins that activate the Wnt signalling pathway by binding to Frizzled (Fz) receptors found on target cells.

Binding of Wnt ligands to Frizzled receptors activates the Dishevelled (Dsh/Dvl1) protein, allowing it to inhibit the activity of a multiprotein complex comprising $\beta$-catenin, Axin-adenomatous polyposis coli (APC) and glycogen synthase kinase (GSK)-3$\beta$. Inhibition of the $\beta$-catenin/APC/GSK-3$\beta$ complex prevents phosphorylation of $\beta$-catenin by GSK-3$\beta$. Phosphorylated $\beta$-catenin is targeted for ubiquitin mediated degradation by the proteosome, and therefore Wnt binding to the Frizzled receptor results in $\beta$-catenin accumulation in the cytoplasm.

Stabilized $\beta$-catenin translocates into the nucleus and binds to members of T-cell factor (Tcf)/Lymphoid enhancing factor (Lef) family of proteins, resulting in the transcription of Wnt target genes.

Reya et al (2003) Nature 423(6938):409-14 discloses a role for Wnt signalling in self-renewal of haematopoietic stem cells (non-pluripotent stem cells). Thus, activation of the Wnt signalling pathway in haematopoietic stem cells maintains pluripotency in these cells.

In contrast, a number of documents in the prior art suggest that activation of Wnt signalling in non-pluripotent stem cells leads to differentiation.

Thus, Lako et al (2001, Mechanisms of Development 103, 49-59) describes a role for Wnt signalling in enhancing differentiation of embryoid bodies. Cells in embryoid bodies are multipotent, but are not pluripotent, i.e., are not capable of giving rise to all three germ layers. Specifically, Lako discloses that activation of Wnt signalling by over-expression of Wnt3 results in haematopoietic differentiation of embryoid bodies.

International Patent Publication WO 2004/113513 describes the use of Wnt polypeptides in the modulation of proliferation or differentiation of a population of adult stem cells, specifically haematopoietic $CD45^+Sca1^+$ stem cells.

WO 2005/052141 provides a number of methods for inducing or inhibiting differentiation of foetal lung stem cells. One particular method disclosed in WO2005/052141 involves in vitro up-regulation of the Wnt pathway in foetal lung stem cells, which results in inhibition of differentiation.

Despite these teachings of the role of Wnt signalling in the induction of differentiation in multipotent stem cells, the Wnt signalling appears to have an opposite role in the regulation of the choice between pluripotency/differentiation in pluripotent embryonic stem cells. Thus, activation of Wnt signalling in embryonic stem cells appears to result in maintenance of the pluripotent state and inhibition of differentiation.

Thus, Sato et al (2004 Nature Medicine 10: 55-63) discloses that activation of Wnt signalling in human and mouse embryonic stem cells leads to maintenance of pluripotency of such stem cells and inhibition of differentiation. In support of this, US 2004/0014209 A1 discloses that inhibition of Wnt signalling pathway plays a role in the stimulation of differentiation of stem cells, including embryonic stem cells, into cardiac cells.

SUMMARY

In contrast to studies by (Sato et al. 2004) that suggest the involvement of Wnt pathway in maintaining pluripotency, our data demonstrate conclusively that sustained activation of Wnt pathway induces differentiation of ES cells. We find that activation of the Wnt signalling pathway in ES cells causes or induces the cells to differentiate along mesendodermal, mesodermal or endodermal pathways.

We have cultured the cells over multiple passages and have analyzed variety of markers. We show here that although the cells retain pluripotency markers viz Oct4 and Nanog even at day 21, the cells acquire a variety of meso/endodermal markers confirming induction of both mesoderm and endoderm in response to Wnt pathway activation. In addition we do not get induction of ectoderm.

According to a $1^{st}$ aspect of the present invention, we provide a method for producing a mesodermal or a endodermal cell from a pluripotent stem cell, the method comprising activating a Wnt signalling pathway in the pluripotent stem cell.

There is provided, according to a $2^{nd}$ aspect of the present invention, a mesodermal or endodermal cell produced according to the $1^{st}$ aspect of the invention.

We provide, according to a $3^{rd}$ aspect of the present invention, a mesendodermal cell produced according to the $1^{st}$ aspect of the invention.

As a $4^{th}$ aspect of the present invention, there is provided a pharmaceutical composition comprising such a mesodermal or endodermal cell, or such a mesendodermal cell, together with a pharmaceutically acceptable carrier, excipient or diluent.

We provide, according to a $5^{th}$ aspect of the present invention, use of such a mesodermal or endodermal cell, or such a mesendodermal cell, or such a pharmaceutical composition, in therapy, such as regenerative medicine.

The present invention, in a 6th aspect, provides a method of treatment of a disease in an individual, the method comprising introducing such a mesodermal or endodermal cell, or such a pharmaceutical composition, or as produced by a method according to the 1st aspect of the invention, to the individual.

In a 7th aspect of the present invention, there is provided a kit comprising a pluripotent stem cell, an activator of a Wnt signalling pathway, together with instructions for use to produce a mesodermal or endodermal cell.

According to an 8th aspect of the present invention, we provide a method of inducing expression of a mesoderm specific marker comprising activating a Wnt signalling pathway in a pluripotent stem cell.

We provide, according to a 9th aspect of the invention, a method of inducing expression of a endoderm specific marker comprising activating a Wnt signalling pathway in a pluripotent stem cell.

BRIEF DESCRIPTION OF THE FIGURES

FIG. 1 shows Wnt signalling in embryonic stem cells.

FIG. 2. Long term activation of the Wnt pathway in E14 cells induces mesendodermal differentiation. E14 cells are treated with control CM, Wnt-3A CM, iGSK-3β separately for 21 days as described in methods.

FIG. 3. Sustained Wnt pathway activation in human ES cells induces mesendodermal differentiation. H1 cells are treated with control CM, Wnt-3A CM, iGSK-3β separately for 21 days as described in methods.

DETAILED DESCRIPTION

Figure 1A:
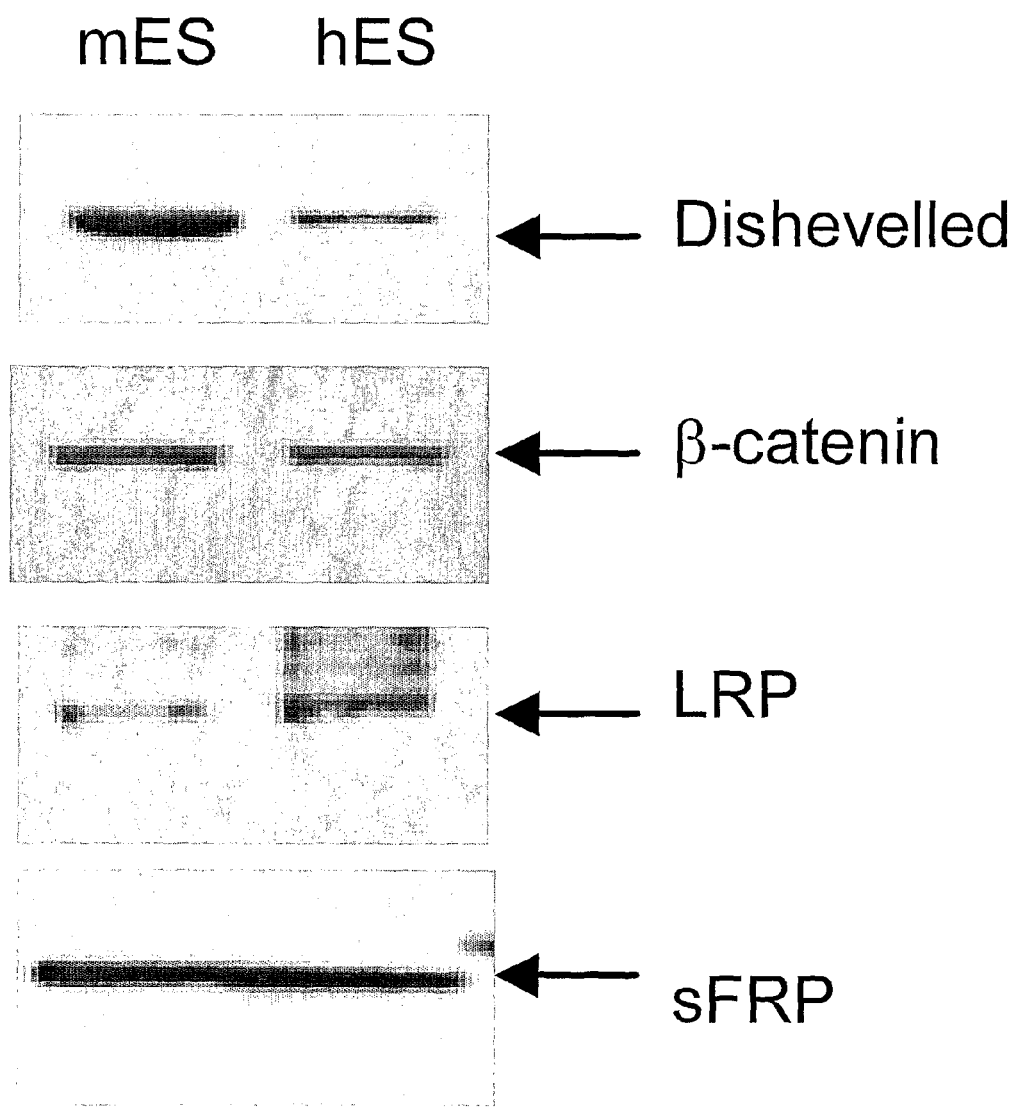
FIG. 1A. Wnt pathway proteins are present in undifferentiated mouse and human ES cells. Western blot analysis on ES cell lysates using anti-dishevelled, β-catenin, LRP and sFRP antibodies.

This invention is based on the demonstration that the Wnt signalling pathway plays a key role in the choice of cell fate of embryonic stem cells. Specifically, we demonstrate that the Wnt signalling pathway regulates the choice of the different fates or lineages an embryonic stem cell can potentially take, specifically, the choice between the three germ layers, mesoderm, endoderm and ectoderm.

Thus, we show in the Examples that, for both murine embryonic stem cells and human embryonic stem cells, when the Wnt signalling pathway is activated by various means, the embryonic stem cell differentiates along two specific pathways, the mesodermal pathway, or the endodermal pathway, but not the ectodermal pathway.

Our methods are therefore generally concerned with the production of differentiated cells from pluripotent stem cells, in particular, differentiated stem cells of defined and restricted lineages. In particular, we provide for methods to produce differentiated cells of mesodermal or endodermal lineages, or both, from pluripotent stem cells, by modulation (such as activation) of the Wnt signalling pathway in such cells. Accordingly, we broadly provide for the manipulation of the choice of cell fates between the mesodermal/endodermal lineage and the ectodermal lineage, by the manipulation of Wnt signalling pathway activity of a pluripotent stem cell. We further provide for differentiated and partially differentiated cells made by the methods described here.

Any component of the Wnt signalling pathway, as described in further detail below, may be activated in order produce mesodermal or endodermal differentiation. By activation of the Wnt signalling pathway, we mean the modulation of the activity of any member of the pathway, or any cellular or other mechanism that regulates the Wnt signalling pathway, which results in activation of transcription of a TCF regulated gene (i.e., a gene comprising a Tcf/LEF consensus binding site in its promoter), including TCF1, TCF2, TCF3, LEF1 and LEF2. TCF/LEF is described in Clevers and van de Wetering, 1997, Trends Genet. 1997 December; 13(12):485-9. In some embodiments, however, activation of the Wnt signalling pathway results in the activation of transcription of a Wnt target gene. Wnt target genes are described in further detail below.

In some embodiments, the activation of the Wnt signalling pathway results in an increase in activity of β-catenin, such as an accumulation of active β-catenin in the cytoplasm, such as an increase in the amount of phosphorylated β-catenin in the cytoplasm.

It will be evident that manipulation of Wnt signalling pathway activity may be used to cause or induce a pluripotent stem cell to enter a mesodermal or endodermal pathway of differentiation ab initio. That is to say, the activation of Wnt signalling as described here may be employed to cause an embryonic stem cell which is equally likely to adopt any of the three cell fates to enter a mesodermal or endodermal pathway of differentiation.

Furthermore, in addition to changing the pathway of the stem cell, activation of Wnt signalling activity may be used to strengthen the commitment or choice of a stem cell fate. That is to say, a stem cell which is in the process of differentiating along a mesodermal or endodermal pathway may be biased towards these pathways and not the ectodermal pathway, by activating Wnt signalling activity in the embryonic stem cell.

Alternatively, activation of the Wnt signalling pathway may be used to cause an embryonic stem cell which is still pluripotent, but already partially committed to differentiation along a specific pathway (e.g., an ectodermal pathway), to enter a mesodermal or endodermal pathway instead.

Furthermore, Wnt signalling may be activated in an embryonic stem cell which is pluripotent, but partially committed to an ectodermal and mesodermal lineage, to cause differentiation towards an endodermal or mesodermal pathway.

In some embodiments, the activity of the Wnt signalling pathway is increased to such an extent (or maintained at that level) that the embryonic stem cell remains in a mesodermal or endodermal differentiating pathway even if the embryonic stem cell is exposed to signals which would otherwise cause differentiation to another pathway, for example the ectodermal pathway.

Detection of Wnt signalling pathway activity may also be used to determine the status of an embryonic stem cell, i.e., whether it is in the process of, or committed to, differentiation along a mesodermal or endodermal pathway.

Embryonic stem cells, differentiating and differentiated cells treated according to the methods and compositions described here may be employed for a variety of purposes, including medical treatment, as described in further detail below.

Any means for increasing Wnt signalling activity may be used, including both direct and indirect modulation. These may include for example, modulating the expression of any endogenous gene for any member of the Wnt signalling pathway (described in further detail below) at the transcriptional, translational or post-translational level, such as modulating the persistence or breakdown of messenger RNA for the member of the Wnt signalling pathway, modulating the persistence or breakdown of protein, etc. They may also include modulation of the activity of a member of the Wnt signalling pathway, such as by use of agonists thereof. Furthermore, the expression and/or activity of activators of any member of the Wnt signalling pathway, may be modulated to modulate Wnt signalling activity. These are described in further detail below.

In some embodiments, the activity of Wnt signalling in the embryonic stem cell may be increased by 10%, 20%, 30%, 40%, 50% or 60% or more to effect differentiation of the stem cell towards mesodermal or endodermal lineages. In some embodiments, Wnt signalling activity may be increased by more than 50% in order to allow such differentiation to take place. In such embodiments, the activity or activation of the Wnt signalling pathway as assayed as described in "Assay for Wnt Signalling Pathway Activation" below.

The Wnt signalling pathway in the ES cell may be activated for more than 12 hours, such as more than 24 hours. In some embodiments, the Wnt signalling pathway is activated for 2 days or more, such as 3 days or more, 4 days or more, 5 days or more, 6 days or more or 7 days or more. In some embodiments, the Wnt signalling pathway in the ES cell is activated for between 8 to 10 days. It will be evident that the Wnt signalling pathway is activated for as long as necessary, depending on the application, for example, 2 weeks, 3 weeks, 4 weeks, etc, as required. In such embodiments, the Wnt signalling pathway may be activated continuously during that time.

In particular, we provide for the use of agonists of Wnt signalling for modulation of Wnt signalling pathway. Such agonists of Wnt signalling may furthermore be identified by screens and assays, also described in detail below.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855, Lars-Inge Larsson "*Immunocytochemistry: Theory and Practice*", CRC Press inc., Baca Raton, Fla., 1988, ISBN 0-8493-6078-1, John D. Pound (ed); "*Immunochemical Protocols, vol 80*", in the series: "Methods in Molecular Biology", Humana Press, Totowa, N.J., 1998, ISBN 0-89603-493-3, Handbook of Drug Screening, edited by Ramakrishna Seethala, Prabhavathi B.

Fernandes (2001, New York, N.Y., Marcel Dekker, ISBN 0-8247-0562-9); Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3; and The Merck Manual of Diagnosis and Therapy (17th Edition, Beers, M. H., and Berkow, R, Eds, ISBN: 0911910107, John Wiley & Sons). Each of these general texts is herein incorporated by reference. Each of these general texts is herein incorporated by reference.

Wnt Signalling Pathway

Any of the components of the Wnt signalling pathway may be modulated in order to activate the pathway.

Figure 7:
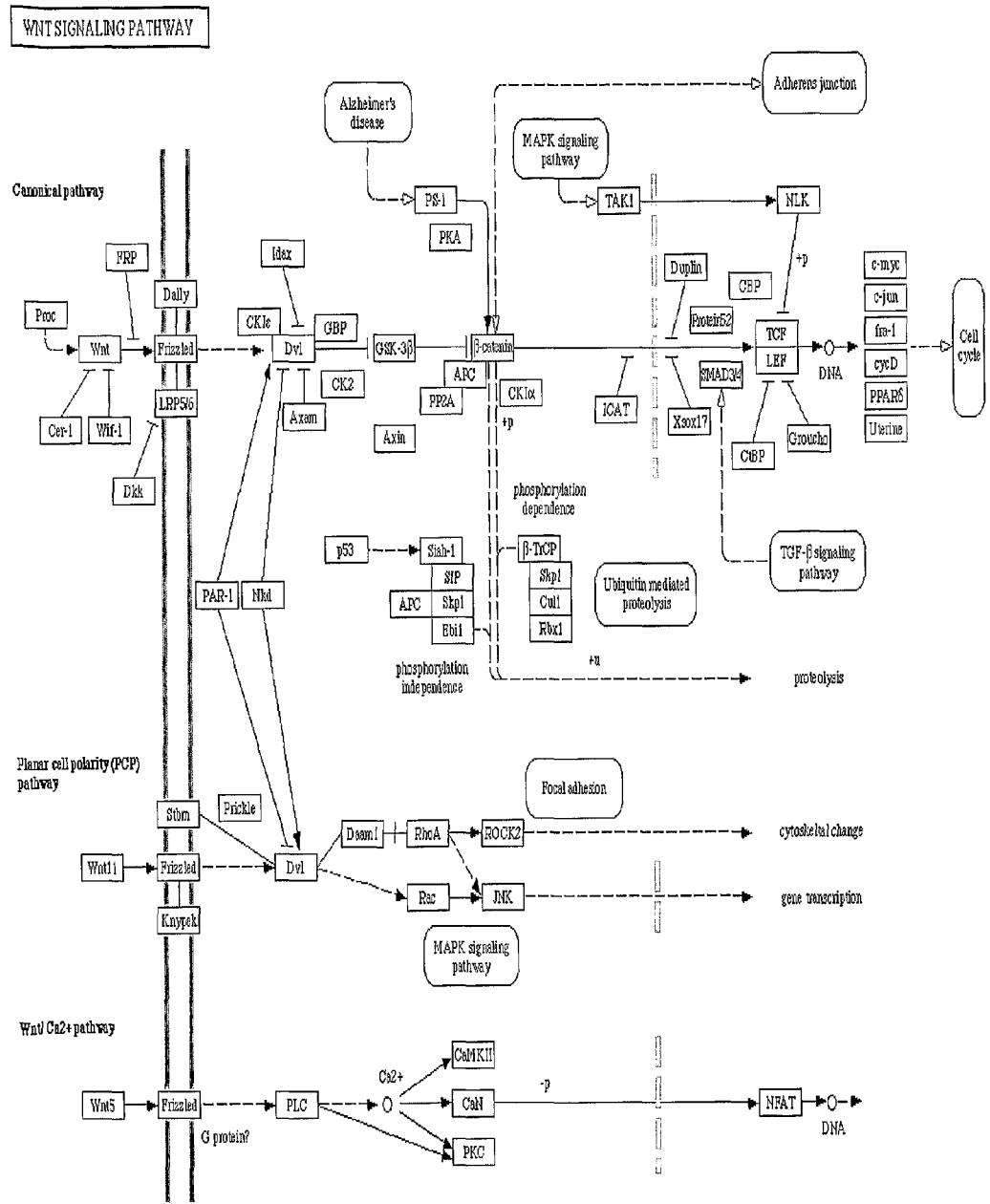
FIG. 7 shows a Wnt signalling pathway.

The Wnt signalling pathway is depicted in FIG. 7, and components of that pathway, as well as their accession numbers, are set out in Annex B. Accordingly, the activity of any protein or component depicted in FIG. 7 or Annex B may be modulated according to the methods and compositions described here, so long as the Wnt signalling pathway is activated, in order to cause an embryonic stem cell to differentiate along a mesodermal or endodermal pathway. Methods for determining whether the Wnt signalling pathway is activated are described in detail below.

In some embodiments, the Wnt signalling pathway is a "canonical" Wnt signalling pathway, i.e., the pathway that involves signalling from Wnt receptors (Frizzleds) to β-catenin (as opposed to non-canonical pathways which do not involve Wnt or β-catenin, such as described and reviewed in Veeman et al., 2003, Dev Cell. 5(3):367-77 and Strutt D, 2003, Development 130(19):4501-13).

The Wnt signalling pathway is described in Thorstensen et al (2003), Atlas Genet Cytogenet Oncol Haematol. April 2003 (http://www.infobiogen.fr/services/chromcancer/Deep/WntSignPathID20042.html). Detailed reviews of Wnt signalling and action are set out in Logan and Nusse (2004), Annu. Rev. Cell Dev. Biol. 20, 781-810 and Wodarz and Nusse (1998), Annu. Rev. Cell Dev. Biol. 14, 59-88. The latter document also describes a number of assays for Wnt signalling. See also http://www.stanford.edu/~rnusse/wntwindow.html.

Assays for Wnt Signalling Pathway Activation

Activation of the Wnt signalling pathway in an embryonic stem cell may be assessed in a number of ways, as known in the art. In general, such an assay will seek to detect the modulation of the target component, or a component downstream of the component which is the target of activation.

In some embodiments, an assay for activation of the Wnt signalling pathway may comprise detection of a reduced activity of GSK-3β. GSK-3β activity may be assessed in a number of ways, for example as described above in detail under "GSK-3β Kinase Assays". Such an assay may be particularly suitable where GSK-3β activity is targeted for inhibition as a means to activate the Wnt signalling pathway.

Alternatively, or in addition, an assay for activation of the Wnt signalling pathway may comprise detecting accumulation of β-catenin in the cytoplasm, or the nucleus, or both. Thus, an increase in the amount or quantity of β-catenin in either or both locations may be assessed as an indication of Wnt signalling pathway activation. This may be achieved by making nuclear or cytoplasmic extracts of the cells in question, e.g., embryonic stem cells or differentiating cells, using means known in the art, and detection of β-catenin protein by antibody Western blots. Particularly useful assays include those which detect active β-catenin, or non-phosphorylated forms of β-catenin, using antibodies specific for such forms, for example.

A monoclonal antibody capable of detecting specifically the active non-phosphorylated form of β-catenin is described in van Noort et al., (2002) J Biol. Chem. 2002 May 17; 277(20):17901-5, and is also available commercially from Upstate (Charlottesville, Va. 22903, USA) as "Anti-β-Catenin (non-phospho), clone 8E4" with catalogue number 05-601.

Activation of the Wnt signalling pathway may also be detected through detection of increase in the expression of Axin2, using Western blots with anti-Axin2 antibodies, for example. Axin 2 is located at 17q23-q24 and has accession number AF205888, AF078165 and NM_004655.

Phosphorylation of Dishevelled, or phosphorylation of the LRP tail (Tamai 2004 Mol. Cell. 2004 Jan. 16; 13(1):149-56) may also be detected as a means of gauging activation of Wnt signalling pathway.

In some embodiments, the activation of the Wnt signalling pathway is detected through use of appropriate reporter plasmids, which are transfected into cells of interest. Expression of the reporter is sensitive to activation of Wnt signalling, as a result of, for example, the promoter for the reporter comprising a response element.

One reporter which may be used in such an assay is a TOP Flash reporter, as described in Molenaar et al., (1996) Cell 86(3):391-9, and available from Upstate Biotech (Charlottesville, Va. 22903, USA, catalogue number 21-170). TOP-Flash comprises a TCF Reporter Plasmid with two sets of three copies of the TCF binding site upstream of the thymidine kinase (TK) minimal promoter and luciferase open reading frame. A control plasmid is FOP-Flash (catalogue number 21-169), containing mutated and non-active TCF-binding sites.

TOPFlash is transiently transfected into suitable receptor cells, such as embryonic stem cells, through use of a suitable transfection reagent such as Lipofectamine 2000 (Invitrogen). Luciferase expression may be detected by use of a luminometer, for example, as known in the art.

Another reporter which may be used in such an assay is Super8XTOPFlash, which comprises a luciferase reporter of β-catenin-mediated transcriptional activation. This reporter is described in detail in M. Veeman et al., Current Biology 13:680 (2003). The Super8XTOPFlash reporter has a higher signal/noise ratio than the TOPFlash reporters. In HEK cells, maximal activation of this reporter is ~100-fold (activation by Wnt) up to ~1,000-fold (activation by phosphorylation mutants of beta-catenin). An appropriate control plasmid is clone M51, Super8XFOPflash, which has mutant TCF/LEF binding sites.

The backbone of Super8XTOPFlash is the pTA-Luc vector of Clontech, which provides a minimal TA viral promoter driving expression of the firefly luciferase gene (see company publications for details). 8 TCF/LEF binding sites were cloned into the Mlu1 site of this vector (8 copies of: AGATCAAAGGgggta, with TCF/LEF binding site in CAP letters, and a spacer in lower case, separating each copy of the TCF/LEF site).

Detection of Wnt signalling pathway activation may be conducted on whole animals, which have been engineered to comprise transgenic reporters. These reporters are based on a multimerized TCF binding site, driving expression of LacZ (sometimes called TOP-GAL). Two transgenic mouse lines have been described, one by DasGupta and Fuchs (1999), Development, 126(20):4557-68. and one by Maretto et al. (2003) Proc Natl Acad Sci USA.100(6):3299-304. A TOP-dGFP Zebrafish line was generated by Dorsky and Moon (2002) and also described by Hurlstone et al. (2003) Nature 425(6958):633-7. Because the expression of Axin2 is under the control of Wnt signaling in many tissues, the transgenic line made by Jho et al., (2002) Mol Cell Biol. 22(4):1172-83, based on the Axin2 promoter and GFP, is also a useful Wnt reporter in animals. Similarly, Lustig et al., (2002) Mol Cell Biol. 22(4):1184-93 inserted LacZ into the endogenous Axin2/Conductin gene to visualize expression of this Wnt target in animals.

Whole animal assays are useful for detecting activators of Wnt signalling pathways which may be used in the methods and compositions described here.

Activation of Wnt Receptor

Frizzled Receptor

In particular, we provide for the activation of the Wnt signalling pathway by activating any of the receptors for Wnt signalling, i.e., a Wnt receptor. For example, any of the Frizzled receptors may be activated to activate the Wnt signalling pathway. Examples of Frizzled receptors are shown in the Tables below.

TABLE

Human Frizzled Receptors

| Gene Symbol | Gene Name | Location | Sequence Accession IDs | Aliases |
|---|---|---|---|---|
| FZD1 | frizzled homolog 1 (*Drosophila*) | 7q21 | AB017363, NM_003505 | |
| FZD2 | frizzled homolog 2 (*Drosophila*) | 17q21.1 | L37882 | |
| FZD3 | frizzled homolog 3 (*Drosophila*) | 8p21 | AJ272427 | |
| FZD4 | frizzled homolog 4 (*Drosophila*) | 11q14-q21 | AB032417 | |
| FZD5 | frizzled homolog 5 (*Drosophila*) | 2q33-q34 | U43318 | Hfz5 |
| FZD6 | frizzled homolog 6 (*Drosophila*) | 8q22.3-q23.1 | AB012911 | Hfz6 |
| FZD7 | frizzled homolog 7 (*Drosophila*) | 2q33 | AB010881 | FzE3 |
| FZD8 | frizzled homolog 8 (*Drosophila*) | 10p11.2 | AB043703, NM_031866 | |
| FZD9 | frizzled homolog 9 (*Drosophila*) | 7q11.23 | U82169 | FZD3 |
| FZD10 | frizzled homolog 10 (*Drosophila*) | 12q24.33 | AB027464 | |

TABLE

Mouse Frizzled Receptors

| Gene Symbol | Gene Name | Location | Sequence Accession IDs | Mouse Genome Informatics No. | Aliases |
|---|---|---|---|---|---|
| Fzd1 | frizzled homolog 1 (*Drosophila*) | 5 5.0 cM | BC053010, NM_021457 | 1196625 | Fz1 |
| Fzd2 | frizzled homolog 2 (*Drosophila*) | 11 syntenic | BC055727, BC049774, NM_020510 | 1888513 | Fzd10, Mfz10, Mfz10a |
| Fzd2-rs1 | frizzled homolog 2, related sequence 1 (*Drosophila*) | 5 2.0 cM | | 108548 | Fz2-rs1, Mfz2 |
| Fzd2-rs2 | frizzled homolog 2, related sequence 2 (*Drosophila*) | 11 62.0 cM | | 108500 | Fz2-rs2 |
| Fzd3 | frizzled homolog 3 (*Drosophila*) | 14 27.0 cM | BC050965, NM_021458 | 108476 | Fz3, Mfz3 |
| Fzd4 | frizzled homolog 4 (*Drosophila*) | 7 44.5 cM | BC015256, NM_008055 | 108520 | Fz4, Mfz4 |
| Fzd5 | frizzled homolog 5 (*Drosophila*) | 1 30.8 cM | AB052910, NM_022721 | 108571 | Fz5, Mfz5, 5330434N09Rik |
| Fzd6 | frizzled homolog 6 (*Drosophila*) | 15 13.1 cM | BC026150 NM_008056 | 108474 | Fz6, Mfz6 |
| Fzd7 | frizzled homolog 7 (*Drosophila*) | 1 30.1 cM | BC063077, NM_008057 | 108570 | Fz7, Mfz7 |
| Fzd8 | frizzled homolog 8 (*Drosophila*) | 18 2.0 cM | NM_008058 | 108460 | Fz8, Mfz8 |
| Fzd9 | frizzled homolog 9 (*Drosophila*) | 5 75.0 cM | XM_284144 (predicted) | 1313278 | Mfz9 |
| Fzd10 | frizzled homolog 10 (*Drosophila*) | 5 syntenic | NM_175284 | 2136761 | Fz10 |

TABLE-continued

Mouse Frizzled Receptors

| Gene Symbol | Gene Name | Location | Sequence Accession IDs | Mouse Genome Informatics No. | Aliases |
|---|---|---|---|---|---|
| Smo (smoothened) | smoothened homolog (*Drosophila*) | 6 7.2 cM | BC096028, BC048091, NM_176996 | 108075 | D13Mgi8, Smoh |

Receptor activation may be achieved in a number of ways, for example, by upregulating the expression of the receptor. This may for example be achieved by transfection of a suitable expression vector expressing the receptor into the embryonic stem cell. Furthermore, receptor activation may be achieved by introduction of a constitutively active Frizzled receptor to the embryonic stem cell, for example by transfection into the embryonic stem cell as an expression vector encoding the constitutively active receptor.

Wnt Ligands

Receptors for Wnt, such as Frizzled receptors, may also be activated by binding of Wnt ligand. Thus, the Wnt signalling pathway may be activated by increasing the activity or expression of Wnt ligand, or by decreasing the activity or expression of antagonists of Wnt or Frizzled.

Wnt ligands are known in the art, and include WNT1, WNT2, WNT2B/13, WNT3, WNT3A, WNT4, WNT5A, WNT5B, WNT6, WNT7A, WNT7B, WNT8A, WNT8B, WNT9A (previously WNT14), WNT9B (previously WNT15), WNT10A, WNT10B, WNT11 and WNT16. Exemplary Wnt ligands include Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11 and Wnt16. Such Wnt ligands, as well as their accession numbers, are set out in Annex A. Any one or more of these may be employed to activate Wnt signalling in embryonic stem cells.

Wnt ligands may be obtained from R&D Systems (Minnesota, USA) and from PeproTech, Inc (New Jersey, USA).

In some embodiments, the Wnt ligand comprises Wnt1 or Wnt3A, such as Wnt3A. The Wnt ligand may comprise Human WNT1 (PAL1) (ATCC 57198/57199), Human WNT1 (MGC 30915522), Human WNT3 (pHP1) (ATCC MBA-174), Mouse Wnt3 (ATCC MBA-175) or Mouse Wnt3A (ATCC MBA-176).

In addition, the Norrin ligand (Xu et al., 2004, *Vascular development in the retina and inner ear: control by Norrin and Frizzled-4, a high-affinity ligand-receptor pair*. Cell 116 (6):883-95), which binds to Frizzled with high affinity, may be used to activate the Wnt signalling pathway. The R-spondin2 protein (Kazanskaya et al (2004) Dev Cell. 7(4):525-34 and Kim et al., (2005) Science 309(5738):1256-9) also binds to the Frizzled receptors and may similarly be used in the methods and compositions described here.

The embryonic stem cell may be exposed to any of the known Wnt ligands, such as a purified polypeptide. Wnt ligands are available commercially from Calbiochem, and may also be made by recombinant means, such as by expression of an expression vector comprising a Wnt nucleic acid in a suitable host cell.

Alternatively, or in addition, the Wnt signalling pathway may be activated by exposing the embryonic stem cell to medium containing the Wnt ligand. An example of such a medium is a "conditioned medium", i.e., medium in which Wnt secreting cells, such as cells transfected with Wnt expression vectors is growing. The presence of the appropriate Wnt ligand in the conditioned medium may be established through known means, such as by Western blots (see also FIG. 1C).

Cells producing Active Wnt and Wingless protein include the following: Mouse Wnt3A (ATCC CRL-2647), Mouse Wnt5A (ATCC CRL-2814) and *Drosophila* Wingless (*Drosophila* Genomics Resource Centre, DGRC 165).

In some embodiments, Wnt3A conditioned medium is employed as a Frizzled receptor. This may be made as described in Example 19 and Shibamoto, et al. Gene Cells 3: 659-670. Lako et al, 2001, also describes the manufacture of Wnt3A and Wnt4 conditioned medium.

Wnt3A Conditioned Medium

An example protocol for making Wnt3A and Wnt5 conditioned medium, adapted from Lako et al, 2001, follows:

The murine Wnt3 and Wnt5a cDNAs are obtained by amplification from undifferentiated CGR8 cells with the following primers: Wnt3: 50-ACCATGGAGCCCCACCTGCT-30; 50-TGCAGGTGTGCACATCGTAG-30 Wnt5a: 50-AC-CATGAAGAAGCCCATTGG-30 50-TGCACACGAACTGATCCACA-30. These cDNAs are cloned into pcDNA3.1/CT-GFP-TOPO (Invitrogen) following the manufacturer's instructions and DNA prepared using the Qiagen midiprep kit. Three clones for each gene are sequenced thoroughly in order to make sure that no nucleotide change had occurred during the amplification steps. COS7 cells are maintained in DMEM (Gibco BRL) supplemented with 10% foetal calf serum in humidified incubators at 378 C with 5% CO2.

For production of conditioned media, the COS7 cells are transfected with the Wnt3 and Wnt5a expression constructs using the Fugene transfection kit (Boehringer Mannheim) following the manufacturer's instructions. A control construct containing the green fluorescent protein, GFP, under the control of CMV promoter is also transfected into COS7 cells. Mock transfections are performed in the absence of any DNA. The medium from each of these transfections is conditioned for 72 h, centrifuged at 3000×g and filter sterilised. To confirm secretion of the Wnt-GFP fusion proteins the conditioned medium (CM) is collected from transfected COS7 cells 72 h after transfection and subjected to fluorimetry studies using a Cytofluor Multiwell Plate reader (Perseptive Biosystems).

Over-Expression of Wnt Ligands

In other embodiments, the Wnt signalling pathway may be activated by increasing the expression of Wnt ligands. For example, activation of the Wnt signalling pathway by Wnt over-expression is described in detail in WO 2004/0014209. The teachings of this document may be used to prepare mRNAs from expression constructs and plasmids comprising Wnt sequences, for injection into embryonic stem cells for inducing differentiation. Furthermore, expression vectors may be transiently or permanently transfected into embryonic stem cells to achieve the same purpose.

Inhibition of Glycogen Synthase Kinase 3β

We provide generally for the activation of a Wnt signalling pathway by down-regulation of any antagonist or negative regulator or component of that pathway, for example, glycogen synthase kinase 3β, whether by inhibiting enzymatic activity or lowering protein concentration. Blocking negative regulators of Wnt signaling, such as Axin and APC through use for example of RNAi will also activate the Wnt pathway.

In particular embodiments, we provide for the activation of the Wnt signalling pathway by the inhibition of kinase activity in the pluripotent stem cell, in particular, glycogen synthase kinase 3 (GSK3) activity.

In some embodiments, the kinase activity that is inhibited is GSK-3β kinase activity. GSK-3β activity may be inhibited by inhibiting the enzymatic activity of GSK-3β, for example by use of chemical inhibitors or antagonists, which may be competitive or non-competitive, as described below. Such inhibitors may include kinase inhibitors.

Furthermore, GSK-3β activity may be down-regulated by down-regulating the expression of GSK-3β protein, such as by use of antisense RNA, or RNAi, or siRNA or by inhibiting the conversion of inactive forms of GSK-3β to active forms, or by increasing the rate of degradation of GSK-3β. The methods and compositions described here may also employ loss of function and dominant negative mutations in GSK-3β, described for example in Hedgepeth et al. (1997) *Activation of the Wnt signaling pathway: a molecular mechanism for lithium action*. Dev Biol. 185(1):82-91. Kinase deficient mutants of GSK-3β, for example as described in Crowder and Freeman, 2000, J. Biol. Chem. 275 (2000), pp. 34266-34271, may be transfected into embryonic stem cells to achieve mesodermal/endodermal differentiation.

Exposure to fibroblast growth factor (FGF) activates Akt and thus inhibits GSK-3β, as described in Hashimoto et al., 2002, J. Biol. Chem. 277 (2002), pp. 32985-32991; FGF may therefore be used as an activator of Wnt signalling.

Wnt signalling may also be activated via up-regulation, for example, over-expression, of FRAT1, a negative regulator of GSK-3. This is described in Crowder and Freeman, 2000, J. Biol. Chem. 275 (2000), pp. 34266-34271 and Culbert, et al., 2001, FEBS Lett. 507 (2001), pp. 288-294.

Methods and compounds suitable for inhibiting GSK-3β activity are set out in detail below.

A "kinase inhibitor", as the term is used in this document, is meant to refer to a compound that exhibits an $IC_{50}$ with respect to the relevant kinase, e.g., to GSK-3β, of no more than about 100 µM and more typically not more than about 50 µM, or less as set out below. Enzyme activities may be measured by the assays as set out in this document. "$IC_{50}$" is that concentration of inhibitor which reduces the activity of an enzyme (e.g., GSK-3β) to half-maximal level. Compounds which have been discovered to exhibit inhibitory activity against GSK-3β may be used in the methods and compositions described here.

Useful compounds may exhibit an $IC_{50}$ with respect to the relevant kinase, e.g., GSK-3β, of no more than about 10 µM, such as no more than about 5 µM, not more than about 1 µM or not more than about 200 nM, as measured in the cell-free GSK-3β kinase assay. In some embodiments, the compounds exhibit an $IC_{50}$ with respect to GSK-3β of no more than about 100 nM, such as no more than about 50nM. In some embodiments, "GSK-3β inhibitor" is used herein to refer to a compound that exhibits an IC50 with respect to GSK-3β of no more than about 100 pM and more typically not more than about 50 µM, as measured in the cell-free assay for GSK-3β inhibitory activity described generally hereinbelow. Alternatively, or in addition, the compound may be capable of inhibiting kinase activity, as set out below, to below 50%, below 35%, 25% or 15% of maximal activity.

Glycogen Synthase Kinase 3 (GSK-3β)

Glycogen synthase kinase-3 (GSK-3) is a serine/threonine protein kinase having a 47 kDa monomeric structure. It is also known as zeste-white-3/shaggy.

GSK-3 is one of several protein kinases which phosphorylates glycogen synthase (Embi, et al., 1980, Eur. J. Biochem., 107:519-527; Hemmings et al., 1982, Eur. J. Biochem. 119: 443-451). GSK-3 is also referred to in the literature as factor A ($F_A$) in the context of its ability to phosphorylate $F_C$, a protein phosphatase (Vandenheede et al., 1980, J. Biol. Chem. 255:11768-11774). Other names for GSK-3 and homologs thereof include zeste-white3/shaggy (zw3/sgg; the *Drosophila melanogaster* homolog), ATP-citrate lyase kinase (ACLK or MFPK; Ramakrishna et al., 1989, Biochem. 28:856-860; Ramakrishna et al., 1985, J. Biol. Chem. 260: 12280-12286), GSLA (the *Dictyostelium* homolog; Harwood et al., 1995, Cell 80:139-48), and MDSI, MCK1, and others (yeast homologs; Hunter et al., 1997, TIBS 22:18-22).

The gene encoding GSK-3 is highly conserved across diverse phyla. GSK-3 exists in two isoforms in vertebrates, GSK-3α and GSK-3β. In vertebrates, the amino acid identity among homologs is in excess of 98% within the catalytic domain of GSK-3 (Plyte et al., 1992, Biochim. Biophys. Acta 1114:147-162). It has been reported that there is only one form of GSK-3 in invertebrates, which appears to more closely resemble GSK-3β than GSK-3α. Amino acid similarities (allowing for conservative replacements) between the slime mold and fission yeast proteins with the catalytic domain of human GSK-3β are 81% and 78%, respectively (Plyte et al., 1992, supra). The remarkably high degree of conservation across the phylogenetic spectrum suggests a fundamental role for GSK-3 in cellular processes.

GSK-3 has been demonstrated to phosphorylate numerous proteins in vitro, including, but not limited to glycogen synthase, phosphatase inhibitor I-2, the type-II subunit of cAMP-dependent protein kinase, the G-subunit of phosphatase-1, ATP-citrate lyase, acetyl coenzyme A carboxylase, myelin basic protein, a microtubule-associated protein, a neurofilament protein, an N-CAM cell adhesion molecule, nerve growth factor receptor, c-Jun transcription factor, JunD transcription factor, c-Myb transcription factor, c-Myc transcription factor, L-myc transcription factor, adenomatous polyposis coli tumor suppressor protein, tau protein, and β-catenin (Plyte et al., 1992, Biochim. Biophys. Acta 1114:147-162; Korinek et al., 1997, Science 275:1784-1787; Miller et al., 1996, Genes & Dev. 10:2527-2539). The phosphorylation site recognized by GSK-3 has been determined in several of these proteins (Plyte et al., 1992, supra). The diversity of these proteins belies a wide role for GSK-3 in the control of cellular metabolism, growth, and development. GSK-3 tends to phosphorylate serine and threonine residues in a proline-rich environment, but does not display the absolute dependence upon these amino acids which is displayed by protein kinases which are members of the mitogen-activated protein (MAP) kinase or cdc2 families of kinase enzymes.

Among the proteins which are phosphorylated by GSK-3 is c-Jun, the expression product of the c-jun proto-oncogene and the cellular homolog of the v-jun oncogene of avian sarcoma virus (Dent et al., 1989, FEBS Lett. 248:67-72). Jun acts as a component of the activator protein-1 (AP-1) transcription factor complex, which binds to a palindromic consensus binding site (the AP-1 site). c-Jun is both necessary and sufficient to induce transcription of genes having an AP-1 site (Angel et al., 1988, Nature 332:166-171; Angel et al., 1988, Cell: 55:875-885; Chiu et al., 1988, Cell 54:541-552; Bohmann et al., 1989, Cell 59:709-717; Abate et al., 1990, Mol. Cell. Biol. 10:5532-5535). Transcription of a gene having an AP-1 site may be initiated by either a Fos-Jun heterodimer or by a Jun-Jun homodimer, although the Fos-Jun heterodimer binds to DNA more stably than the Jun-Jun homodimer and is consequently a more potent transcription activator. Fos is the expression product of another proto-oncogene, c-fos (Schonthal et al., 1988, Cell 54:325-334; Sassone-Corsi, 1988, Nature 334:314-319). Phosphorylation of c-Jun by GSK-3 severely reduces the binding affinity of Jun-Jun homodimer for AP-1 sites (Boyle et al., 1991, Cell 64:573-584; Plyte et al., 1992, supra).

GSK-3 is a negative regulator of the wnt signaling pathway. The wnt pathway is a highly conserved signaling pathway that regulates cell fate decisions in both vertebrates and invertebrates (Perrimon, 1994, Cell 76:781-784; Perrimon, 1996, Cell 86:513-516; Miller et al., 1996, Genes & Dev. 10:2527-2539). Much of the pathway has been determined from detailed genetic analysis in Drosophila. At present, identified components of this signaling pathway include wnts (the secreted ligand), frizzled (the wnt receptor), and the intracellular mediators disheveled, GSK-3 (denoted zw3/sgg in Drosophila), and β-catenin (denoted armadillo in Drosophila). In 10T1/2 cells, wnt signaling inhibits GSK-3 p enzymatic activity (Cook et al., 1996, EMBO J. 15:4526-4536). This result is consistent with epistasis experiments in Drosophila which suggest an inhibitory role for GSK-3β/zw3/sgg in the wnt pathway. Wnt signaling leads to stabilization of β-catenin protein in Drosophila (Peifer et al., 1994, Dev., 120:369-380; van Leeuwen, et al., 1994, Nature 368:342-344) as well as Xenopus (Yost et al., 1996, Genes & Dev., 10:1443-1454). It has also been demonstrated that treatment of Drosophila S2 cells with LiCl leads to accumulation of armadillo protein (Stambolic et al., 1996, Curr. Biol. 6:1664-1668). Stabilization of β-catenin is associated with translocation of β-catenin to the nuclei of cells responding to wnt signaling (Funayama et al., 1995, J. Cell Biol., 128:959-968; Schneider et al., 1996, Mech. Dev., 57:191-198; Yost et al., 1996, supra). In addition, ectopic expression of conserved genes, including wnts, disheveled, and β-catenin, leads to second axis formation in Xenopus. Second axis formation in Xenopus is also observed following lithium treatment. Although β-catenin was originally discovered as a cadherin-binding protein, it has recently been shown to function as a transcriptional activator when complexed with members of the Tcf family of DNA binding proteins (Molenaar et al., 1996, Cell 86:391; Behrens et al., 1996, Nature 382:638).

As used above and elsewhere herein the following terms have the meanings defined below: "Glycogen synthase kinase 3" and "GSK-3" are used interchangeably herein to refer to any protein having more than 60%, such as more than 70%, more than 80%, more than 90% or 95%, sequence homology to the human GSK-3 beta amino acid sequence (Genbank Accession No. L33801), for example to the sequence of amino acids between positions 56 and 340 of that sequence. Sequences of GSK-3α and GSK-3β have also been disclosed as accession numbers P49840 and P49841 respectively, and the terms "Glycogen synthase kinase 3" and "GSK-3" may in addition be used to indicate sequences having more than 60%, etc sequence homology to these two sequences.

To determine the percent homology of two amino acid sequences or of two nucleic acids, the sequences are aligned for optimal comparison purposes (e.g., gaps can be introduced in the sequence of one polypeptide or nucleic acid for optimal alignment with the other polypeptide or nucleic acid). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=number of identical positions/total number of positions×100).

GSK-3-β Kinase Assays

In general, a cell-free GSK-3 kinase assay can be readily carried out by: (1) incubating GSK-3 with a peptide substrate, radiolabeled ATP (such as, for example, $\gamma^{33}$P- or $\gamma^{32}$P-ATP, both available from Amersham, Arlington Heights, Ill.), magnesium ions, and optionally, one or more candidate inhibitors; (2) incubating the mixture for a period of time to allow incorporation of radiolabeled phosphate into the peptide substrate by GSK-3 activity; (3) transferring all or a portion of the enzyme reaction mix to a separate vessel, typically a microtiter well that contains a uniform amount of a capture ligand that is capable of binding to an anchor ligand on the peptide substrate; (4) washing to remove unreacted radiolabeled ATP; then (5) quantifying the amount of $^{33}$P or $^{32}$P remaining in each well. This amount represents the amount of radiolabeled phosphate incorporated into the peptide substrate. Inhibition is observed as a reduction in the incorporation of radiolabeled phosphate into the peptide substrate.

Suitable peptide substrates for use in the cell free assay may be any peptide, polypeptide or synthetic peptide derivative that can be phosphorylated by GSK-3β in the presence of an appropriate amount of ATP. Suitable peptide substrates may be based on portions of the sequences of various natural protein substrates of GSK-3 or other enzyme, and may also contain N-terminal or C-terminal modifications or extensions including spacer sequences and anchor ligands. Thus, the peptide substrate may reside within a larger polypeptide, or may be an isolated peptide designed for phosphorylation by GSK-3β, etc For example, a peptide substrate can be designed based on a subsequence of the DNA binding protein CREB, such as the SGSG-linked CREB peptide sequence within the CREB DNA binding protein described in Wang et al., Anal. Biochem., 220: 397-402 (1994), incorporated herein by reference. In the assay reported by Wang et al., the Cterminal serine in the SXXXS motif of the CREB peptide is enzymatically prephosphorylated by cAMP-dependent protein kinase (PKA), a step which is required to render the N-terminal serine in the motif phosphorylatable by GSK-3. As an alternative, a modified CREB peptide substrate can be employed which has the same SXXXS motif and which also contains an N-terminal anchor ligand, but which is synthesized with its Cterminal serine prephosphorylated (such a substrate is available commercially from Chiron Technologies PTY Ltd., Clayton, Australia). Phosphorylation of the second serine in the SXXXS motif during peptide synthesis eliminates the need to enzymatically phosphorylate that residue with PKA as a separate step, and incorporation of an anchor ligand facilitates capture of the peptide substrate after its reaction with GSK-3.

Generally, a peptide substrate used for a kinase activity assay may contain one or more sites that are phosphorylatable by GSK-3β and one or more other sites that are phosphorylatable by other kinases, but not by the relevant kinase. Thus, these other sites can be prephosphorylated in order to create a motif that is phosphorylatable by the kinase. The term "prephosphorylated" refers herein to the phosphorylation of a substrate peptide with nonradiolabeled phosphate prior to conducting a kinase assay using that substrate peptide.

Such prephosphorylation can conveniently be performed during synthesis of the peptide substrate.

The SGSG-linked CREB peptide can be linked to an anchor ligand, such as biotin, where the serine near the C terminus between P and Y is prephosphorylated. As used herein, the term "anchor ligand" refers to a ligand that can be attached to a peptide substrate to facilitate capture of the peptide substrate on a capture ligand, and which functions to hold the peptide substrate in place during wash steps, yet allows removal of unreacted radiolabeled ATP. An exemplary anchor ligand is biotin. The term "capture ligand" refers herein to a molecule which can bind an anchor ligand with high affinity, and which is attached to a solid structure. Examples of bound capture ligands include, for example, avidin- or streptavidin-coated microtiter wells or agarose beads. Beads bearing capture ligands can be further combined with a scintillant to provide a means for detecting captured radiolabeled substrate peptide, or scintillant can be added to the captured peptide in a later step.

The captured radiolabeled peptide substrate can be quantitated in a scintillation counter using known methods. The signal detected in the scintillation counter will be proportional to the GSK-3β kinase activity if the enzyme reaction has been run under conditions where only a limited portion (e.g., less than 20%) of the peptide substrate is phosphorylated. If an inhibitor is present during the reaction, the relevant kinase activity will be reduced, and a smaller quantity of radiolabeled phosphate will thus be incorporated into the peptide substrate.

Hence, a lower scintillation signal will be detected. Consequently, GSK-3β inhibitory activity will be detected as a reduction in scintillation signal, as compared to that observed in a negative control where no inhibitor is present during the reaction.

A cell-based GSK-3β kinase activity assay typically utilizes a cell that can express both GSK-3β and a GSK-3β substrate, such as, for example, a cell transformed with genes encoding GSK-3β and its substrate, including regulatory control sequences for the expression of the genes. In carrying out the cell-based assay, the cell capable of expressing the genes is incubated in the presence of a compound. The cell is lysed, and the proportion of the substrate in the phosphorylated form is determined, e.g., by observing its mobility relative to the unphosphorylated form on SDS PAGE or by determining the amount of substrate that is recognized by an antibody specific for the phosphorylated form of the substrate. The amount of phosphorylation of the substrate is an indication of the inhibitory activity of the compound, i.e., inhibition is detected as a decrease in phosphorylation as compared to the assay conducted with no inhibitor present. GSK-3 inhibitory activity detected in a cell-based assay may be due, for example, to inhibition of the expression of GSK-3 or by inhibition of the kinase activity of GSK-3.

Chemical Inhibitors of GSK-3β Activity

As noted above, the Wnt signalling pathway can be activated by inhibition of GSK-3β activity. In some embodiments, the GSK-3β is exposed to a chemical inhibitor thereof in order to achieve this.

A number of chemical inhibitors of GSK-3β activity are known in the art, as described in for example U.S. Pat. No. 6,441,053. Methods for identifying inhibitors of GSK-3β activity are also set out in that document. Such methods typically involve providing a mixture comprising GSK-3, a phosphate source, and a GSK-3 substrate, incubating the mixture in the presence or absence of a test compound, and assessing the activity of GSK-3 in the mixture. A reduction of GSK-3 activity following incubation of the mixture in the presence of the test compound is an indication that the test compound is an inhibitor of GSK-3.

Lithium

In one embodiment, our methods and compositions employ lithium and its salts, including lithium chloride for activation of the Wnt signalling pathway. The use of lithium in this manner is described in Hedgepeth et al. (1997) *Activation of the Wnt signaling pathway: a molecular mechanism for lithium action*. Dev Biol. 185(1):82-91, as well as in Davies, et al. (2000), Biochem. J. 351, pp. 95-105 and Patel et al., (2002), J. Mol. Biol. 315 (2002), pp. 677-685.

Lithium may be used at concentrations of between 1 micromolar and 500 millimolar in order to activate Wnt signalling for differentiation. A suitable concentration is greater than 10 mM.

Indirubins

In some embodiments, the chemical inhibitors of GSK-3β comprise indirubins, for example, Tyrian purple indirubins, as described in detail in Meijer et al., (2003). *GSK-3-Selective Inhibitors Derived from Tyrian Purple Indirubins*. Chemistry & Biology, Vol. 10, 1255-1266. In particular, we provide for the use of 6-bromoindirubins, such as the use of indirubins substituted at position 5 or position 6. The indirubin may be substituted at position 6.

6-bromoindirubin-3'-oxime (BIO)

Figure 6:
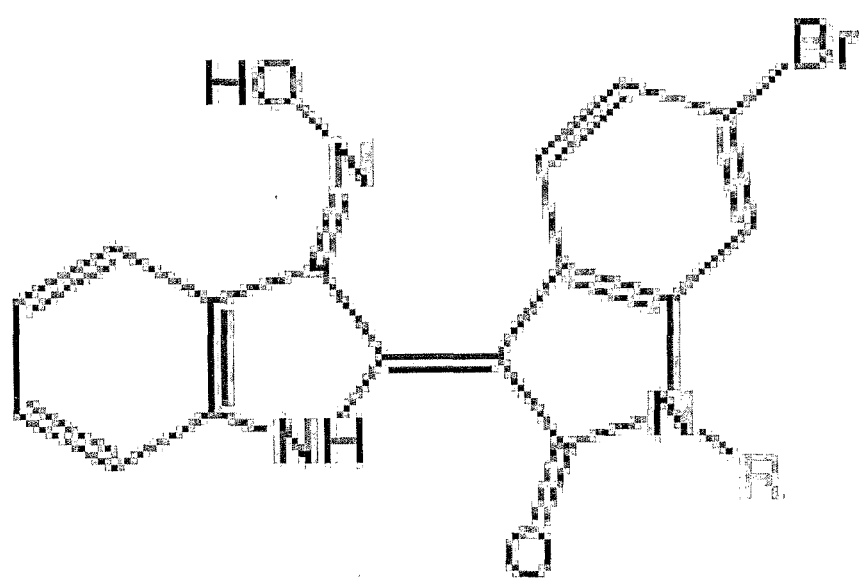
FIG. 6 shows the structures of BIO and MeBIO.

In some embodiments, the GSK-3β inhibitor comprises 6-bromoindirubin-3'-oxime (BIO), as depicted in FIG. 6. The embryonic stem cell may be exposed to the indirubin, such as 6-bromoindirubin-3'-oxime (BIO), at a concentration of between 1 nM and 1 mM, such as more than 500 nM, more than 750 nM, less than 500 μM, less than 100 μM, less than 50 μM, or less than 25 μM, in order to achieve differentiation along mesodermal/endodermal pathways. In some embodiments, the concentration is between 0.1 μM and 10 μM, such as between 1 μM and 10 μM, for example below 5 μM, such as around 1 μM or 2 μM.

In other embodiments, our methods and compositions make use of chemical inhibitors of GSK-3β which comprise iGSK-3β and its variants. iGSK-3β may be used at the concentrations recited above as for BIO.

Other Inhibitors of GSK-3

Coghlan et al, Chem. Biol. 2000 October; 7(10):793-803 describe two molecules, SB-216763 and SB-415286, structurally distinct maleimides, as inhibitors of GSK3. Pai et al, Mol Biol Cell. 2004 May; 15(5):2156-63 report that low concentrations of Deoxy-cholic acid (DCA, 5 and 50 micro M) increase tyrosine phosphorylation of beta-catenin, induce urokinase-type plasminogen activator (uPA), uPA receptor (uPAR) and cyclin D1 expression and enhance colon cancer cell proliferation and invasiveness. Park et al, Biochem Biophys Res Commun. 2005 Mar. 4; 328(1):227-34 suggest that quercetin inhibits Wnt signaling at the level of TCF. Liu et al., Angew Chem Int Ed Engl. 2005 Mar. 18; 44(13):1987-90 report on 2-amino-4-[3,4-(methylenedioxy)benzyl-amino]-6-(3-methoxyphenyl)pyrimidine as an agonist of Wnt signaling. Each of these compounds may therefore be used to activate the Wnt signalling pathway in a pluripotent stem cell.

In other embodiments, the methods and compositions described here employ inhibitors of GSK-3β, for example, those available from Calbiochem (San Diego, USA). These include 1-Azakenpaullone (Calbiochem catalogue no. 191500), Alsterpaullone (Calbiochem catalogue no. 126870), FRATtide (Calbiochem catalogue no. 344265), GSK-3b Inhibitor VII (Calbiochem catalogue no. 361548), GSK-3b Inhibitor XI (Calbiochem catalogue no. 361553), GSK-3b Inhibitor I (Calbiochem catalogue no. 361540), GSK-3b Inhibitor II (Calbiochem catalogue no. 361541), GSK-3b Inhibitor III (Calbiochem catalogue no. 361542), GSK-3 Inhibitor IX (Calbiochem catalogue no. 361550).

Other GSK-3β inhibitors available from Calbiochem include InSolution™ GSK-3 Inhibitor IX (Calbiochem catalogue no. 361552), GSK-3 Inhibitor X (Calbiochem catalogue no. 361551), GSK-3 Inhibitor XIII (Calbiochem catalogue no. 361555), GSK-3 Inhibitor XIV, Control, MeBIO (Calbiochem catalogue no. 361556), GSK-3b Inhibitor VI (Calbiochem catalogue no. 361547), GSK-3b Inhibitor XII, TWS119 (Calbiochem catalogue no. 361554), GSK-3b Inhibitor VIII (Calbiochem catalogue no. 361549), GSK-3b Peptide Inhibitor (Calbiochem catalogue no. 361545), GSK-3b Peptide Inhibitor, Cell-permeable (Calbiochem catalogue no. 361546), Indirubin-3'-monoxime (Calbiochem catalogue no. 402085), Kenpaullone (Calbiochem catalogue no. 422000). The GSK-3β inhibitors may be used at any effective concentration, for example, typically between 1 μM and 10 μM.

In other embodiments, Wnt signalling may be activated by use of the cyclin dependent kinase (CDK) inhibitors described in Leclerc, et al., (2001), J. Biol. Chem. 276 (2001), pp. 251-260, and Knockaert et al., (2002), J. Biol. Chem. 277 (2002), pp. 25493-25501.

β-Catenin

As the term is used in this document, β-catenin refers to a sequence having NCBI GeneID 93703. β-catenin in its phosphorylated form is targeted for destruction, while the non-phosphorylated form is active. Accumulation of β-catenin in the cytoplasm leads to accumulation in the nucleus and consequent activation of transcription of Wnt responsive genes or Wnt target genes.

Accordingly, we provide for the activation of Wnt signalling by activation of β-catenin, by which we mean any process which ultimately leads to an increase of β-catenin activity in the cell, such as accumulation of active (non-phosphorylated) β-catenin in the cell. Such processes may include anything that increases the expression or activity of β-catenin, such as transfection of an embryonic stem cell with an expression vector which expresses β-catenin (or a constitutively active version thereof, as described below). They may also include, alternatively, or in addition, inhibiting or down-regulating of degradation of β-catenin, such as by down-regulation of phosphorylation of β-catenin, by use of kinase inhibitors, or phosphatases, etc.

The methods and compositions described here may also make use of β-catenin to activate Wnt signalling. Such constitutively active β-catenin forms include for example β-catenin which is not capable of being degraded, such as by not being able to be phosphorylated. Non-phosphorylable forms of β-catenin may be those in which lack one or more sites required for phosphorylation, whether sites for kinase binding, or for phosphate attachment. Mutant forms are described in Munemitsu et al (1996) Mol Cell Biol. 16(8):4088-94 and Yost et al. (1996) Genes Dev. 10(12):1443-54. Over-expression of β-catenin by transfection of an expression construct is also described in Reya et al., (2003) Nature 423(6938):409-14. In some embodiments, the β-catenin construct is a N terminally truncated form as described in Reya et al.

Mutant beta-catenin forms further include mutants in which one or more of the residues specified in Wnt signaling and cancer. Genes Dev. 2000 Aug. 1; 14(15):1837-51 are mutated to another amino acid, for example alanine. They further include deletion mutants lacking N-terminal 50-90 amino acids i.e., residues which are phosphorylated by GSK-3b, APC, Dsh complex.

Such mutant forms are Wnt unresponsive, and may be supplied to the embryonic stem cell (whether externally in the medium or internally as expression products) to cause differentiation along the mesodermal or endodermal pathway.

Configurations

In some embodiments, substantially all the cells in a population of interest are exposed to the signal causing the activation of the Wnt signalling pathway simultaneously. They may receive substantially the same level of signal, such as for substantially the same amount of time. In some embodiments, the cells are configured in relation to each other and to the container in which they grow, in such a way to achieve these purposes.

For example, the cells may be arranged in a two dimensional configuration to enable even exposure to the signal. Thus, in certain embodiments, the pluripotent stem cell is in a substantially 2 dimensional configuration for at least a portion of the time when the Wnt signalling pathway is activated. In some embodiments, the pluripotent stem cell is in such a configuration for substantially all of the time when the Wnt signalling pathway is activated.

By a two dimensional configuration we mean a configuration in which cells are allowed to grow along two dimensions, without substantially growing along a third. In some embodiments, there is no substantial "stacking" of cells on top of one another. At least some of the cells, such as a majority,=or all the cells, may be attached directly or indirectly to a substrate. The cell may attach directly to the substrate and grow on it. The cell may be attached indirectly to the substrate by being attached to a cell which is in direct attachment to the substrate. The cell may be in contact with a substrate.

The substrate may comprise the surface of a container, or a feeder layer. The cells may be attached to the substrate. In some embodiments, the cells are in a flattened configuration.

Examples of configurations include monolayers. In some embodiments, the cells are not arranged in the form of an embryoid body. At least 70%, such as at least 80% of the cells in a population, may be differentiating along the same pathway.

Embryonic Stem Cells and Progenitor Cells

The methods described here are capable of producing partially differentiated progenitor cells, and cell lines thereof, of mesodermal or endodermal lineages.

When embryonic stem cells differentiate, they generally recapitulate the complexity of early mammalian development where embryonic stem cells transit through a series of lineage restriction to generate progenitor cells of decreasing lineage potential before finally generating terminally differentiated cells representing all three germ layers (Wiles, Methods in Enzymology. 1993; 225:900-918).

Typically, stem cells generate an intermediate cell type or types before they achieve their fully differentiated state, referred to as a precursor or progenitor cell. Progenitor or precursor cells in foetal or adult tissues are partly differentiated cells that divide and give rise to differentiated cells. Such cells are usually regarded as "committed" to differentiating along a particular cellular development pathway, Progenitor cells are therefore sometimes referred to as "committed stem cells".

Our methods are capable of producing of progenitor cells and cell lines of various types, particularly mesodermal or endodermal types.

For example, we disclose a method of making peripheral blood progenitor cells (PBPC), haematopoeitic progenitor cells, myeloid progenitor cells, bone marrow stromal cells, skeletal muscle progenitor cells, pancreatic islet progenitor cells, mesenchymal progenitor cells, cardiac mesodermal stem cells, lung and liver progenitor cells.

Progenitor cells of mesodermal or endodermal types made according to the methods described here can be used for a variety of commercially important research, diagnostic, and therapeutic purposes. These uses are generally well known in the art, but will be described briefly here.

For example, the methods and compositions described here may be employed on embryonic stem cells to generate mesodermal or endodermal progenitor cell populations for regenerative therapy. Progenitor cells may be made by ex vivo expansion or directly administered into a patient. They may also be used for the re-population of damaged tissue following trauma.

Thus, hematopoietic progenitor cells may be used for bone marrow replacement, while cardiac progenitor cells may be used for cardiac failure patients. Skin progenitor cells may be employed for growing skin grafts for patients and endothelial progenitor cells for endothelization of artificial prosthetics such as stents or artificial hearts.

Embryonic stem cells may be used as sources of mesodermal or endodermal progenitor cells for the treatment of degenerative diseases such as diabetes, Alzheimer's disease, Parkinson's disease, etc. Embryonic stem cells may be used as sources of mesodermal or endodermal progenitors for NK or dendritic cells for immunotherapy for cancer, which mesodermal or endodermal progenitors may be made by the methods and compositions described here.

It will be evident that the methods and compositions described here enable the production of mesodermal or endodermal progenitor cells, which may of course be made to further differentiate using methods known in the art to terminally differentiated cell types. Thus, any uses of terminally differentiated cells will equally attach to those mesodermal or endodermal progenitor cells for which they are sources.

Mesodermal or endodermal progenitor cells produced by the methods and compositions described here may be used for, or for the preparation of a pharmaceutical composition for, the treatment of a disease. Such disease may comprise a disease treatable by regenerative therapy, including cardiac failure, bone marrow disease, skin disease, burns, degenerative disease such as diabetes, Alzheimer's disease, Parkinson's disease, etc and cancer.

Characteristics of Progenitor Cells

The methods and compositions described here may be used to induce differentiation of embryonic stem cells into mesodermal or endodermal progenitor cells, which are partially differentiated.

In some embodiments, the progenitor cells and cell lines (or the differentiated cells derived from them) do not display one or more characteristics of embryonic stem cells. Such characteristics may include expression of the OCT4 gene and alkaline phosphatase activity. The progenitor cell line may exhibit reduced expression of one or more characteristic markers of pluripotency. Such pluripotency markers are described in further detail below, but include Nanog, BMP4, FGF5, Oct4, Sox-2 and Utf1.

Progenitor cells made by the methods described here may be non-tumorigenic. The progenitor cells when implanted into an immune compromised or immunodeficient host animal do not result in tumours, compared to implantation of parental embryonic stem cells which results in tumour formation. The immune compromised or immunodeficient host animal may be a SCID mouse or a Rag1 −/− mouse. In some embodiments, the progenitor cells do not form tumours after prolonged periods of implantation, such as greater than 2 weeks or greater than 2 months, such as greater than 9 months.

Progenitor cells made by the methods described here may also display one or more of the following characteristics. They may have a substantially stable karyotype as assessed by chromosome number, when maintained in cell culture for at least 10 generations. They also may display a substantially stable gene expression pattern from generation to generation. By this we mean that the expression levels one or more, such as substantially all, of a chosen set of genes does not vary significantly between a progenitor cell in one generation and a progenitor cell in the next generation.

The set of genes may comprise one or more, a subset, or all of, the following: cerberus (GenBank Accession nos: NM_009887, AF031896, AF035579), FABP (GenBank Accession nos: NM_007980, M65034, AY523818, AY523819), Foxa2 (GenBank Accession nos: NM_010446, X74937, L10409), Gata-1 (GenBank Accession nos: NM_008089, X15763, BC052653), Gata-4 (GenBank Accession nos: NM_008092, AF179424, U85046, M98339, AB075549), Hesx1 (GenBank Accession nos: NM_010420, X80040, U40720, AK082831), HNF4a (GenBank Accession nos: NM_008261, D29015, BC039220), c-kit (GenBank Accession nos: NM_021099, Y00864, AY536430, BC075716, AK047010, BC026713, BC052457, AK046795), PDGFRα (NM_011058, M57683, M84607, BC053036), Oct4 (GenBank Accession nos: NM_013633, X52437, M34381, BC068268), Runx1 (GenBank Accession nos: NM_009821, D26532, BC069929, AK051758), Sox17 (GenBank Accession nos: NM_011441, D49474, L29085, AK004781), Sox2 (GenBank Accession nos: NM_011443, U31967, AB108673), Brachyury (NM_009309, X51683), TDGF1 (GenBank Accession nos: NM_011562, M87321) and Tie-2 (GenBank Accession nos: NM_013690, X67553, X71426, D13738, BC050824).

The methods described here enable the production of progenitor cells and progenitor cell lines as well as fully differentiated cells, which comprise clonal descendants of progenitor cells. The term "clonal descendant" of a cell refers to descendants of the cells which have not undergone substantially any transforming treatment or genetic alteration. Such clonal descendants have not undergone substantial genomic changes are substantially genetically identical to the parent cell, or an ancestor, such as the embryonic stem cell (save with reduced potency). The term "progenitor cell" may also be taken to include cell lines derived from progenitor cells, i.e., progenitor cell lines, and vice versa.

Mesoderm and Endoderm

The identification of mesodermal and endodermal cells, including terminally differentiated cells as well as cells committed to mesodermal and endodermal pathways is known in the art.

Markers of mesodermal differentiation or commitment include T-brachyury, Gata 2, Nkx2.5, Albumin, Flk1, Runx1, Runx2, Hand1,2 and Tbx5. The expression of any one or more of these markers may be detected to detect a mesodermal cell. Markers of endodermal differentiation or commitment include Sox17, Foxa2, Gata 4-6, AFP, MixL1, Goosecoid, Sox7, IPF1. The expression of any one or more of these markers may be detected to detect a endodermal cell.

In some aspects, the methods and compositions described here provide for the production of mesendodermal cells from ES cells by the activation of the Wnt signalling pathway.

Anatomic proximity and common signaling networks link the earliest mesoderm and endoderm cells to form primitive mesendoderm that is distinguished from the ectoderm (Kimelman and Griffin 2001, Rodaway and Patient 2001).

The primitive mesendoderm has some degree of developmental plasticity which can be utilized to segregate into mesoderm or endoderm in response to appropriate inducers.

By a "mesendodermal" cell, we mean a cell which has the potential to develop along mesodermal or endodermal pathways. Such a cell may be a bipotent cell. In some embodiments, such a cell does not, and cannot, differentiate along an ectodermal pathway. In some embodiments, mesendodermal cells express one or more mesodermal and/or endodermal markers, as described elsewhere in this document.

Differentiated Mesodermal or Endodermal Cells

Differentiated cells, such as partially or terminally differentiated cells, may be derived from the progenitor cells or cell lines made according to the methods described. For example, mesodermal or endodermal cells can be terminally differentiated by exposure to a growth factor or hormone. We therefore disclose methods for generating differentiated cells, the methods comprising generating progenitor cells or cell lines as described, and deriving differentiated cells from these.

Differentiated cells which may be made according to the methods described here may include any or all of the following:

i) adipocyte: the functional cell type of fat, or adipose tissue, that is found throughout the body, particularly under the skin. Adipocytes store and synthesize fat for energy, thermal regulation and cushioning against mechanical shock ii) cardiomyocytes: the functional muscle cell type of the heart that allows it to beat continuously and rhythmically iii) chondrocyte: the functional cell type that makes cartilage for joints, ear canals, trachea, epiglottis, larynx, the discs between vertebrae and the ends of ribs iv) fibroblast: a connective or support cell found within most tissues of the body. Fibroblasts provide an instructive support scaffold to help the functional cell types of a specific organ perform correctly.

v) hepatocyte: the functional cell type of the liver that makes enzymes for detoxifying metabolic waste, destroying red blood cells and reclaiming their constituents, and the synthesis of proteins for the blood plasma vi) hematopoietic cell: the functional cell type that makes blood. Hematopoietic cells are found within the bone marrow of adults. In the fetus, hematopoietic cells are found within the liver, spleen, bone marrow and support tissues surrounding the fetus in the womb.

vii) myocyte: the functional cell type of muscles viii) osteoblast: the functional cell type responsible for making bone ix) islet cell: the functional cell of the pancreas that is responsible for secreting insulin, glucogon, gastrin and somatostatin. Together, these molecules regulate a number of processes including carbohydrate and fat metabolism, blood glucose levels and acid secretions into the stomach.

In some embodiments, the differentiation of Wnt-activated ES cells is carried out in vitro.

We find that the Wnt-activated cells generated using the methods and compositions described here can give rise to mesoderm and endoderm. Thus, these cells provide an improved source of cells that will give rise to therapeutically important cell types that derive from mesoderm and endoderm.

Endoderm derived cells of interest include pancreatic and hepatic cell types. The mesoderm potential of these cells we will enable the generation of cells from this lineage, including; cardiomyocytes, endothelial cells, chondrocytes, and osteoblast cells for example.

Combinations with Other Methods

The methods described herein of Wnt pathway activation of pluripotent cells may be employed on their own, or may be combined with any of the known methods of generating meso and endodermal derivatives and/or differentiated cells, examples of which are described below. The Wnt pathway may be activated prior to, subsequent to, or at the same time as, these methods.

Specifically, a mesodermal or a endodermal cell may be derived from a pluripotent stem cell by a method comprising activating a Wnt signalling pathway in the pluripotent stem cell. Subsequently, any of the known methods described below may be used to derive a specific differentiated cell type from the resulting mesodermal or a endodermal cell.

Thus, for example, the methods described in Kania, Blyszczuk et al. 2003; Kania, Blyszczuk et al. 2004 may be employed in combination with Wnt pathway activation as described here in order to generate hepatocytes.

Furthermore, the methods described in Assady, Maor et al. 2001; Segev, Fishman et al. 2004 may be employed in combination with Wnt pathway activation as described here in order to generate pancreatic cells.

Furthermore, the methods described in Yamashita, Itoh et al. 2000 may be employed in combination with Wnt pathway activation as described here in order to generate endothelial cells.

Furthermore, the methods described in Mummery, Ward et al. 2002; Xu, Police et al. 2002; Kehat, Amit et al. 2003; Mummery, Ward-van Oostwaard et al. 2003 may be employed in combination with Wnt pathway activation as described here in order to generate cardiomyocytes Furthermore, the methods described in Buttery, Bourne et al. 2001; Cao, Heng et al. 2005 may be employed in combination with Wnt pathway activation as described here in order to generate osteogenic cells Furthermore, the methods described in Kramer, Bohrnsen et al. 2006 may be employed in combination with Wnt pathway activation as described here in order to generate chondrocytes.

These established methods have shown potential in mouse and/or human ES cell differentiation. However, the efficiencies of the differentiation processes are limited. According to the methods and compositions described here, it is possible to improve upon these established methods by treatment of the progenitor cells derived as described herein by Wnt pathway activation. Since such cells are committed towards meso- and endoderm, they will likely have an improved efficiency in giving rise to the desired cell types.

Uses of Progenitor Cells and Differentiated Cells

Mesodermal or endodermal progenitor cell lines and differentiated cells made according to the methods and compositions described here may be used for a variety of commercially important research, diagnostic, and therapeutic purposes.

For example, populations of differentiated mesodermal or endodermal cells may be used to prepare antibodies and cDNA libraries that are specific for the differentiated phenotype. General techniques used in raising, purifying and modifying antibodies, and their use in immunoassays and immunoisolation methods are described in Handbook of Experimental Immunology (Weir & Blackwell, eds.); Current Protocols in Immunology (Coligan et al., eds.); and Methods of Immunological Analysis (Masseyeff et al., eds., Weinheim: VCH Verlags GmbH). General techniques involved in preparation of mRNA and cDNA libraries are described in RNA Methodologies: A Laboratory Guide for Isolation and Characterization (R. E. Farrell, Academic Press, 1998); cDNA Library Protocols (Cowell & Austin, eds., Humana Press); and Functional Genomics (Hunt & Livesey, eds., 2000). Relatively homogeneous cell populations are particularly suited for use in drug screening and therapeutic applications.

These and other uses of mesodermal or endodermal progenitor cell lines and mesodermal or endodermal differentiated cells are described in further detail below, and elsewhere in this document. The progenitor cell lines and differentiated cells may in particular be used for the preparation of a pharmaceutical composition for the treatment of disease. Such disease may comprise a disease treatable by regenerative therapy, including cardiac failure, bone marrow disease, skin disease, burns, degenerative disease such as diabetes, Alzheimer's disease, Parkinson's disease, etc and cancer.

Drug Screening

Mesodermal or endodermal progenitor cell lines and mesodermal or endodermal differentiated cells made according to the methods and compositions described here may also be used to screen for factors (such as solvents, small molecule drugs, peptides, polynucleotides, and the like) or environmental conditions (such as culture conditions or manipulation) that affect the characteristics of differentiated cells.

In some applications, progenitor cell lines and differentiated cells are used to screen factors that promote maturation, or promote proliferation and maintenance of such cells in long-term culture. For example, candidate maturation factors or growth factors are tested by adding them to progenitor cells or differentiated cells in different wells, and then determining any phenotypic change that results, according to desirable criteria for further culture and use of the cells.

Furthermore, gene expression profiling of mesodermal or endodermal progenitor cell lines and differentiated mesodermal or endodermal cells may be used to identify receptors, transcription factors, and signaling molecules that are unique or highly expressed in these cells. Specific ligands, small molecule inhibitors or activators for the receptors, transcription factors and signaling molecules may be used to modulate differentiation and properties of progenitor cell lines and differentiated cells.

Particular screening applications relate to the testing of pharmaceutical compounds in drug research. The reader is referred generally to the standard textbook "In vitro Methods in Pharmaceutical Research", Academic Press, 1997, and U.S. Pat. No. 5,030,015), as well as the general description of drug screens elsewhere in this document. Assessment of the activity of candidate pharmaceutical compounds generally involves combining the differentiated cells with the candidate compound, determining any change in the morphology, marker phenotype, or metabolic activity of the cells that is attributable to the compound (compared with untreated cells or cells treated with an inert compound), and then correlating the effect of the compound with the observed change.

The screening may be done, for example, either because the compound is designed to have a pharmacological effect on mesodermal or endodermal cell types, or because a compound designed to have effects elsewhere may have unintended side effects. Two or more drugs can be tested in combination (by combining with the cells either simultaneously or sequentially), to detect possible drug—drug interaction effects. In some applications, compounds are screened initially for potential toxicity (Castell et al., pp. 375-410 in "In vitro Methods in Pharmaceutical Research," Academic Press, 1997). Cytotoxicity can be determined in the first instance by the effect on cell viability, survival, morphology, and expression or release of certain markers, receptors or enzymes. Effects of a drug on chromosomal DNA can be determined by measuring DNA synthesis or repair. [$^3$H]thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (PP 375-410 in "In vitro Methods in Pharmaceutical Research," Academic Press, 1997) for further elaboration.

Tissue Regeneration

Mesodermal or endodermal progenitor cell lines and mesodermal or endodermal differentiated cells made according to the methods and compositions described here may also be used for tissue reconstitution or regeneration in a human patient in need thereof. The cells are administered in a manner that permits them to graft to the intended tissue site and reconstitute or regenerate the functionally deficient area.

For example, the methods and compositions described here may be used to modulate the differentiation of stem cells into mesodermal or endodermal cell types. Progenitor cell lines and differentiated cells may be used for tissue engineering, such as for the growing of skin grafts. Modulation of stem cell differentiation may be used for the bioengineering of artificial organs or tissues, or for prosthetics, such as stents.

Hepatocytes and hepatocyte precursors prepared using our methods can be used to repair liver damage. One such example is damage caused by intraperitoneal injection of D-galactosamine (Dabeva et al., Am. J. Pathol. 143:1606, 1993). Efficacy of treatment can be determined by immunohistochemical staining for liver cell markers, microscopic determination of whether canalicular structures form in growing tissue, and the ability of the treatment to restore synthesis of liver-specific proteins. Liver cells can be used in therapy by direct administration, or as part of a bioassist device that provides temporary liver function while the subject's liver tissue regenerates itself following fulminant hepatic failure.

Furthermore, cardiomyocytes prepared according to the methods described here can be used for the treatment of cardiac cryoinjury, which causes 55% of the left ventricular wall tissue to become scar tissue without treatment (Li et al., Ann. Thorac. Surg. 62:654, 1996; Sakai et al., Ann. Thorac. Surg. 8:2074, 1999, Sakai et al., J. Thorac. Cardiovasc. Surg. 118:715, 1999). Successful treatment will reduce the area of the scar, limit scar expansion, and improve heart function as determined by systolic, diastolic, and developed pressure. Cardiac injury can also be modeled using an embolization coil in the distal portion of the left anterior descending artery (Watanabe et al., Cell Transplant. 7:239, 1998), and efficacy of treatment can be evaluated by histology and cardiac function. Cardiomyocyte preparations can be used in therapy to regenerate cardiac muscle and treat insufficient cardiac function (U.S. Pat. No. 5,919,449 and WO 99/03973).

Cancer

Mesodermal or endodermal progenitor cell lines and differentiated cells made by the methods and compositions described here may be used for the treatment of cancer.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia.

More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer. Further examples are solid tumor cancer including colon cancer, breast cancer, lung cancer and prostrate cancer, hematopoietic malignancies including leukemias and lymphomas, Hodgkin's disease, aplastic anemia, skin cancer and familiar adenomatous polyposis. Further examples include brain neoplasms, colorectal neoplasms, breast neoplasms, cervix neoplasms, eye neoplasms, liver neoplasms, lung neoplasms, pancreatic neoplasms, ovarian neoplasms, prostatic neoplasms, skin neoplasms, testicular neoplasms, neoplasms, bone neoplasms, trophoblastic neoplasms, fallopian tube neoplasms, rectal neoplasms, colonic neoplasms, kidney neoplasms, stomach neoplasms, and parathyroid neoplasms. Breast cancer, prostate cancer, pancreatic cancer, colorectal cancer, lung cancer, malignant melanoma, leukaemia, lympyhoma, ovarian cancer, cervical cancer and biliary tract carcinoma are also included.

In some embodiments, the mesodermal or endodermal progenitor cell lines and differentiated cells made according to the methods and compositions described here are used to treat T cell lymphoma, melanoma or lung cancer.

The mesodermal or endodermal progenitor cell lines and differentiated cells made according to the methods and compositions described here may also be used in combination with anticancer agents such as endostatin and angiostatin or cytotoxic agents or chemotherapeutic agent. For example, drugs such as such as adriamycin, daunomycin, cis-platinum, etoposide, taxol, taxotere and alkaloids, such as vincristine, and antimetabolites such as methotrexate. The term "cytotoxic agent" as used herein refers to a substance that inhibits or prevents the function of cells and/or causes destruction of cells. The term is intended to include radioactive isotopes (e.g. I, Y, Pr), chemotherapeutic agents, and toxins such as enzymatically active toxins of bacterial, fungal, plant or animal origin, or fragments thereof.

Also, the term includes oncogene product/tyrosine kinase inhibitors, such as the bicyclic ansamycins disclosed in WO 94/22867; 1,2-bis(arylamino) benzoic acid derivatives disclosed in EP 600832; 6,7-diamino-phthalazin-1-one derivatives disclosed in EP 600831; 4,5-bis(arylamino)-phthalimide derivatives as disclosed in EP 516598; or peptides which inhibit binding of a tyrosine kinase to a SH2-containing substrate protein (see WO 94/07913, for example). A "chemotherapeutic agent" is a chemical compound useful in the treatment of cancer. Examples of chemotherapeutic agents include Adriamycin, Doxorubicin, 5-Fluorouracil (5-FU), Cytosine arabinoside (Ara-C), Cyclophosphamide, Thiotepa, Busulfan, Cytoxin, Taxol, Methotrexate, Cisplatin, Melphalan, Vinblastine, Bleomycin, Etoposide, Ifosfamide, Mitomycin C, Mitoxantrone, Vincristine, VP-16, Vinorelbine, Carboplatin, Teniposide, Daunomycin, Carminomycin, Aminopterin, Dactinomycin, Mitomycins, Nicotinamide, Esperamicins (see U.S. Pat. No. 4,675,187), Melphalan and other related nitrogen mustards, and endocrine therapies (such as diethylstilbestrol (DES), Tamoxifen, LHRH antagonizing drugs, progestins, anti-progestins etc).

Stem Cells

As used in this document, the term "stem cell" refers to a cell that on division faces two developmental options: the daughter cells can be identical to the original cell (self-renewal) or they may be the progenitors of more specialised cell types (differentiation). The stem cell is therefore capable of adopting one or other pathway (a further pathway exists in which one of each cell type can be formed). Stem cells are therefore cells which are not terminally differentiated and are able to produce cells of other types.

Stem cells as referred to in this document may include totipotent stem cells, pluripotent stem cells, and multipotent stem cells.

Totipotent Stem Cells

The term "totipotent" cell refers to a cell which has the potential to become any cell type in the adult body, or any cell of the extraembryonic membranes (e.g., placenta). Thus, the only totipotent cells are the fertilized egg and the first 4 or so cells produced by its cleavage.

Pluripotent Stein Cells

"Pluripotent stem cells" are true stem cells, with the potential to make any differentiated cell in the body. However, they cannot contribute to making the extraembryonic membranes which are derived from the trophoblast. Several types of pluripotent stem cells have been found. In some embodiments, the pluripotent stem cell comprises an embryonic stem cell Embryonic Stem Cells Embryonic Stem (ES) cells may be isolated from the inner cell mass (ICM) of the blastocyst, which is the stage of embryonic development when implantation occurs.

Embryonic Germ Cells

Embryonic Germ (EG) cells may be isolated from the precursor to the gonads in aborted fetuses.

Embryonic Carcinoma Cells

Embryonic Carcinoma (EC) cells may be isolated from teratocarcinomas, a tumor that occasionally occurs in a gonad of a fetus. Unlike the first two, they are usually aneuploid. All three of these types of pluripotent stem cells can only be isolated from embryonic or fetal tissue and can be grown in culture. Methods are known in the art which prevent these pluripotent cells from differentiating.

Adult Stem Cells

Adult stem cells comprise a wide variety of types including neuronal, skin and the blood forming stem cells which are the active component in bone marrow transplantation. These latter stem cell types are also the principal feature of umbilical cord-derived stem cells. Adult stem cells can mature both in the laboratory and in the body into functional, more specialised cell types although the exact number of cell types is limited by the type of stem cell chosen.

Multipotent Stem Cells

Multipotent stem cells are true stem cells but can only differentiate into a limited number of types. For example, the bone marrow contains multipotent stem cells that give rise to all the cells of the blood but not to other types of cells. Multipotent stem cells are found in adult animals. It is thought that every organ in the body (brain, liver) contains them where they can replace dead or damaged cells.

Methods of characterising stem cells are known in the art, and include the use of standard assay methods such as clonal assay, flow cytometry, long-term culture and molecular biological techniques e.g. PCR, RT-PCR and Southern blotting.

In addition to morphological differences, human and murine pluripotent stem cells differ in their expression of a number of cell surface antigens (stem cell markers). Antibodies for the identification of stem cell markers including the Stage-Specific Embryonic Antigens 1 and 4 (SSEA-1 and SSEA-4) and Tumor Rejection Antigen 1-60 and 1-81 (TRA-1-60, TRA-1-81) may be obtained commercially, for example from Chemicon International, Inc (Temecula, Calif., USA). The immunological detection of these antigens using monoclonal antibodies has been widely used to characterize pluripotent stem cells (Shamblott M. J. et. al. (1998) PNAS 95: 13726-13731; Schuldiner M. et. al. (2000). PNAS 97: 11307-11312; Thomson J. A. et. al. (1998). Science 282: 1145-1147; Reubinoff B. E. et. al. (2000). Nature Biotechnology 18:

399-404; Henderson J. K. et. al. (2002). Stem Cells 20: 329-337; Pera M. et. al. (2000). J. Cell Science 113: 5-10.).

Sources of Pluripotent Stem Cells

Pluripotent stem cells of various types, including embryonic stem cells, which may include the following non-limiting examples, may be used in the methods and compositions described here for producing mesodermal or endodermal progenitor cells, mesodermal or endodermal progenitor cell lines and mesodermal or endodermal differentiated cells.

Pluripotent stem cells of any vertebrate species can be used. Included are stem cells from humans; as well as non-human primates, domestic animals, livestock, and other non-human mammals.

Amongst the stem cells suitable for use in this invention are primate pluripotent stem (pPS) cells derived from tissue formed after gestation, such as a blastocyst, or fetal or embryonic tissue taken any time during gestation. Non-limiting examples are primary cultures or established lines of embryonic stem cells.

Media and Feeder Cells

Media for isolating and propagating pPS cells can have any of several different formulas, as long as the cells obtained have the desired characteristics, and can be propagated further. Suitable sources are as follows: Dulbecco's modified Eagles medium (DMEM), Gibco#11965-092; Knockout Dulbecco's modified Eagles medium (KO DMEM), Gibco#10829-018; 200 mM L-glutamine, Gibco#15039-027; non-essential amino acid solution, Gibco 11140-050; beta-mercaptoethanol, Sigma#M7522; human recombinant basic fibroblast growth factor (bFGF), Gibco#13256-029. Exemplary serum-containing embryonic stem (ES) medium is made with 80% DMEM (typically KO DMEM), 20% defined fetal bovine serum (FBS) not heat inactivated, 0.1 mM non-essential amino acids, 1 mM L-glutamine, and 0.1 mM beta-mercaptoethanol. The medium is filtered and stored at 4 degrees C. for no longer than 2 weeks. Serum-free embryonic stem (ES) medium is made with 80% KO DMEM, 20% serum replacement, 0.1 mM non-essential amino acids, 1 mM L-glutamine, and 0.1 mM beta-mercaptoethanol. An effective serum replacement is Gibco#10828-028. The medium is filtered and stored at 4 degrees C. for no longer than 2 weeks. Just before use, human bFGF is added to a final concentration of 4 ng/mL (Bodnar et al., Geron Corp, International Patent Publication WO 99/20741).

Feeder cells (where used) are propagated in mEF medium, containing 90% DMEM (Gibco#11965-092), 10% FBS (Hyclone#30071-03), and 2 mM glutamine. mEFs are propagated in T150 flasks (Corning#430825), splitting the cells 1:2 every other day with trypsin, keeping the cells subconfluent. To prepare the feeder cell layer, cells are irradiated at a dose to inhibit proliferation but permit synthesis of important factors that support human embryonic stem cells (.about.4000 rads gamma irradiation). Six-well culture plates (such as Falcon#304) are coated by incubation at 37 degrees C. with 1 mL 0.5% gelatin per well overnight, and plated with 375,000 irradiated mEFs per well. Feeder cell layers are typically used 5 h to 4 days after plating. The medium is replaced with fresh human embryonic stem (hES) medium just before seeding pPS cells.

Conditions for culturing other stem cells are known, and can be optimized appropriately according to the cell type. Media and culture techniques for particular cell types referred to in the previous section are provided in the references cited.

Embryonic Stem Cells

Embryonic stem cells can be isolated from blastocysts of members of the primate species (Thomson et al., Proc. Natl. Acad. Sci. USA 92:7844, 1995). Human embryonic stem (hES) cells can be prepared from human blastocyst cells using the techniques described by Thomson et al. (U.S. Pat. No. 5,843,780; Science 282:1145, 1998; Curr. Top. Dev. Biol. 38:133 ff., 1998) and Reubinoff et al, Nature Biotech. 18:399, 2000.

Briefly, human blastocysts are obtained from human in vivo preimplantation embryos. Alternatively, in vitro fertilized (IVF) embryos can be used, or one cell human embryos can be expanded to the blastocyst stage (Bongso et al., Hum Reprod 4: 706, 1989). Human embryos are cultured to the blastocyst stage in G1.2 and G2.2 medium (Gardner et al., Fertil. Steril. 69:84, 1998). Blastocysts that develop are selected for embryonic stem cell isolation. The zona pellucida is removed from blastocysts by brief exposure to pronase (Sigma). The inner cell masses are isolated by immunosurgery, in which blastocysts are exposed to a 1:50 dilution of rabbit anti-human spleen cell antiserum for 30 minutes, then washed for 5 minutes three times in DMEM, and exposed to a 1:5 dilution of Guinea pig complement (Gibco) for 3 minutes (see Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps either by exposure to calcium and magnesium-free phosphate-buffered saline (PBS) with 1 mM EDTA, by exposure to dispase or trypsin, or by mechanical dissociation with a micropipette; and then replated on mEF in fresh medium. Dissociated cells are replated on mEF feeder layers in fresh embryonic stem (ES) medium, and observed for colony formation. Colonies demonstrating undifferentiated morphology are individually selected by micropipette, mechanically dissociated into clumps, and replated. embryonic stem cell-like morphology is characterized as compact colonies with apparently high nucleus to cytoplasm ratio and prominent nucleoli. Resulting embryonic stem cells are then routinely split every 1-2 weeks by brief trypsinization, exposure to Dulbecco's PBS (without calcium or magnesium and with 2 mM EDTA), exposure to type IV collagenase (.about.200 U/mL; Gibco) or by selection of individual colonies by micropipette. Clump sizes of about 50 to 100 cells are optimal.

Self-Renewal and Differentiation

Self-Renewal

Stem cells which are self-renewing may be identified by various means known in the art, for example, morphology, immunohistochemistry, molecular biology, etc.

Such stem cells may display increased expression of Oct4 and/or SSEA-1. Expression of any one or more of Flk-1, Tie-2 and c-kit may be decreased. Stem cells which are self-renewing may display a shortened cell cycle compared to stem cells which are not self-renewing.

For example, in the two dimensions of a standard microscopic image, human embryonic stem cells display high nuclear/cytoplasmic ratios in the plane of the image, prominent nucleoli, and compact colony formation with poorly discernable cell junctions. Cell lines can be karyotyped using a standard G-banding technique (available at many clinical diagnostics labs that provides routine karyotyping services, such as the Cytogenetics Lab at Oakland Calif.) and compared to published human karyotypes.

Human embryonic stem and human embryonic germ cells may also be characterized by expressed cell markers. In general, the tissue-specific markers discussed in this disclosure can be detected using a suitable immunological technique—such as flow cytometry for membrane-bound markers, immunohistochemistry for intracellular markers, and enzyme-linked immunoassay, for markers secreted into the medium. The expression of protein markers can also be detected at the mRNA level by reverse transcriptase-PCR using marker-specific primers. See U.S. Pat. No. 5,843,780 for further details.

Stage-specific embryonic antigens (SSEA) are characteristic of certain embryonic cell types. Antibodies for SSEA markers are available from the Developmental Studies Hybridoma Bank (Bethesda Md.). Other useful markers are detectable using antibodies designated Tra-1-60 and Tra-1-81 (Andrews et al., Cell Linesfrom Human Gem Cell Tumors, in E. J. Robertson, 1987, supra). Human embryonic stem cells are typically SSEA-1 negative and SSEA-4 positive. hEG cells are typically SSEA-1 positive. Differentiation of pPS cells in vitro results in the loss of SSEA-4, Tra-1-60, and Tra-1-81 expression and increased expression of SSEA-1. pPS cells can also be characterized by the presence of alkaline phosphatase activity, which can be detected by fixing the cells with 4% paraformaldehyde, and then developing with Vector Red as a substrate, as described by the manufacturer (Vector Laboratories, Burlingame Calif.).

Embryonic stem cells are also typically telomerase positive and OCT-4 positive. Telomerase activity can be determined using TRAP activity assay (Kim et al., Science 266:2011, 1997), using a commercially available kit (TRAPeze.RTM. XK Telomerase Detection Kit, Cat. s7707; Intergen Co., Purchase N.Y.; or TeloTAGGG.TM. Telomerase PCR ELISA plus, Cat. 2,013,89; Roche Diagnostics, Indianapolis). hTERT expression can also be evaluated at the mRNA level by RT-PCR. The LightCycler TeloTAGGG.TM. hTERT quantification kit (Cat. 3,012,344; Roche Diagnostics) is available commercially for research purposes.

Differentiation

Differentiating cells, including progenitor cell lines and differentiated cells derived from these, may display enhanced dephosphorylation of 4E-BP1 and/or S6K1. They may display decreased expression of Oct4 and/or SSEA-1. Expression of any one or more of Flk-1, Tie-2 and c-kit may be increased. Expression of any one or more of Brachyury, AFP, nestin and nurr1 expression may be increased. Stem cells which are self-renewing may display a lengthened cell cycle compared to stem cells which are not self-renewing.

Differentiating stem cells, i.e., cells which have started to, or are committed to a pathway of differentiation can be characterized according to a number of phenotypic criteria, including in particular transcript changes. The criteria include but are not limited to characterization of morphological features, detection or quantitation of expressed cell markers and enzymatic activity, gene expression and determination of the functional properties of the cells in vivo. In general, differentiating stem cells will have one or more features of the cell type which is the final product of the differentiation process, i.e., the differentiated cell. For example, if the target cell type is a muscle cell, a stem cell which is in the process of differentiating to such a cell will have for example a feature of myosin expression.

In many respects, therefore, the criteria will depend on the fate of the differentiating stem cell, and a general description of various cell types is provided below.

Markers of interest for differentiated or differentiating neural cells include beta-tubulin EIII or neurofilament, characteristic of neurons; glial fibrillary acidic protein (GFAP), present in astrocytes; galactocerebroside (GalC) or myelin basic protein (MBP); characteristic of oligodendrocytes; OCT-4, characteristic of undifferentiated human embryonic stem cells; nestin, characteristic of neural precursors and other cells. A2B5 and NCAM are characteristic of glial progenitors and neural progenitors, respectively. Cells can also be tested for secretion of characteristic biologically active substances. For example, GABA-secreting neurons can be identified by production of glutamic acid decarboxylase or GABA. Dopaminergic neurons can be identified by production of dopa decarboxylase, dopamine, or tyrosine hydroxylase.

Markers of interest for differentiated or differentiating liver cells include alpha-fetoprotein (liver progenitors); albumin, $\alpha_1$-antitrypsin, glucose-6-phosphatase, cytochrome p450 activity, transferrin, asialoglycoprotein receptor, and glycogen storage (hepatocytes); CK7, CK19, and gamma-glutamyl transferase (bile epithelium). It has been reported that hepatocyte differentiation requires the transcription factor BNF-4 alpha (Li et al., Genes Dev. 14:464, 2000). Markers independent of HNF-4 alpha expression include alpha$_1$-antitrypsin, alpha-fetoprotein, apoE, glucokinase, insulin growth factors 1 and 2, IGF-1 receptor, insulin receptor, and leptin. Markers dependent on HNF-4 alpha expression include albumin, apoAI, apoAII, apoB, apoCIII, apoCII, aldolase B, phenylalanine hydroxylase, L-type fatty acid binding protein, transferrin, retinol binding protein, and erythropoietin (EPO).

Cell types in mixed cell populations derived from pPS cells can be recognized by characteristic morphology and the markers they express. For skeletal muscle: myoD, myogenin, and myf-5. For endothelial cells: PECAM (platelet endothelial cell adhesion molecule), Flk-1, tie-i, tie-2, vascular endothelial (VE) cadherin, MECA-32, and MEC-14.7. For smooth muscle cells: specific myosin heavy chain. For cardiomyocytes: GATA-4, NRx2.5, cardiac troponin I, alpha-myosin heavy chain, and ANF. For pancreatic cells: pdx and insulin secretion. For hematopoietic cells and their progenitors: GATA-1, CD34, AC133, β-major globulin, and β-major globulin like gene PH1.

Certain tissue-specific markers listed in this disclosure or known in the art can be detected by immunological techniques—such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. Sequence data for the particular markers listed in this disclosure can be obtained from public databases such as GenBank (URL www.ncbi.nlm.nih.gov:80/entrez).

EXAMPLES

Example 1

Materials and Methods

Preparation of Cell Lysates and Western Blotting

Cells are washed twice in cold PBS and then total protein is extracted using lysis buffer from Cell Signaling supplemented with 25 mM Sodium Fluoride (NaF), 1 mM sodium ortho-vanadate (Na3VO4), 1% DOC, 1% NP40 and proteases inhibitor cocktail tablet (Roche). The cell lysates are incubated on ice for 20 mins, spun at 13000 rpm at 4° C. for 15 mins.

Protein estimation is performed on the supernatant. 40 µg of protein is loaded per lane and resolved on 12% SDS-PAGE. Resolved proteins are transferred to the nitrocellulose membrane. The blots are incubated with primary antibodies, β-actin, (Chemicon), Oct4, Nanog, Wnt-3A (Santa Cruz Biotechnology), SSEA 4 (DHSB), active β-catenin (UBI) and appropriate HRP conjugated secondary antibodies (Pierce) diluted in 5% skim milk. Blots are developed using ECL Western Blot detection reagents (Pierce).

RNA Extraction

MESCs are trypsinised and resuspended in trizol. Total RNA is extracted using Trizol reagent (Gibco). RNA is purified further using the spin column according to the manufacturer's instruction (Qiagen). 1 µg of total RNA is converted to cDNA using Archive kit containing the buffer solution, random primers, reverse transcriptase and dNTPs (Promega) according to the manufacturer's instruction. cDNAs are diluted 1:10 to use for real-time PCR.

Conventional PCR

1 µg of total RNA of E14s is converted to cDNA as described above. PCR mix is prepared using E14 cDNAs, 10× buffer (Invitrogen), 2.5 mM dNTPs (Promega), 1.5 mM $MgCl_2$ (Invitrogen), 1 µM of forward and reverse primers (Proligos) and Taq Polymerase. The PCR thermal profile used are; 1) 95° C. for 10 mins, 2) 30 cycles of 95° C. for 1 min, annealing temperature at 55° C. and 1 min of 72° C. for elongation, 3) 72° C. for 5 mins and kept cool at 4° C.

The frizzled gene sequences are as followed: frizzled 2 forward sequences are 5'-ACA TCG CCT ACA ACC AGA CC-3'; frizzled 2 reverse sequences are—5'-GAG ATA GGA CGG CAC CTT GA-3'; frizzled 5 forward sequences are—5'-GGC ATC TTC ACC CTG CTC TA-3'; frizzled 5 reverse sequences are—5'-GCCTCCAGGCCTTCCTATAC-3'; frizzled 7 forward sequences are—5'-TCT GTC CCT CAC TTG GTT CC-3'; 3' and the frizzled 7 reverse sequences are 5'-AAG TAG CAG GCC AAC ACG AT-3'

Luciferase Assay

Luciferase assays are performed in 293-T cells and mES cells. TOP Flash and FOP Flash plasmids are purchased from Upstate Biotech Inc. Cells are transiently transfected with the plasmids using Lipofectamine 2000 (Invitrogen). Plasmid (pRL-TK) encoding *Renilla luciferease* is used to normalize transfection efficiency. Luciferase assays are performed using Promega kit according to the manufacturer's instructions.

Real-Time PCR

PCR mix is prepared by mixing diluted cDNA (see RNA extraction above), mastermix (Applied Biosystems) and probes according to the manufacturer's instruction. cDNA made from untreated mES or hES cells at the appropriate day are used as controls for the treated cells.

Samples are processed using ABI7900HT Sequence Detection Machine. Results are analyzed using SDS2.2. Results are expressed as fold increase over untreated mouse or human ES cells.

Fluorescene-Assorted Cells Sorting (FACS)

HESCs are trypsinised and aliquoted in $5 \times 10^5$ cells per sample. Cells are fixed and permeabilised using FIX and PERM cell kit (Caltag Laboratories). Cells are incubated with anti-SSEA-4 antibody (DHSB) at room temperature (RT) for 15 mins. Cells are washed twice with 1% Bovine Serum Albumin (BSA) in PBS. Cells are incubated with FITC-conjugated goat-anti-mouse secondary antibody at RT for 15 mins. The cells are washed twice again with PBS containing 1% BSA and analyzed using the FACS Analyzer (BD). Control is done without primary antibody and the rest of the procedure followed as mentioned earlier.

6-bromoindirubin-3'-oxime (BIO)

6-bromoindirubin-3'-oxime (BIO) is obtained from Ali Brivanlou (Rockefeller University).

Example 2

Mouse Embryonic Stem Cells

Mouse Embryonic Stem Cells (mESCs)-E14TG2a are obtained from ATCC. mESCs are cultured feeder-free on 0.1% gelatin-coated dishes in the presence of Leukemia Inhibitory Factor (LIF) with growth media comprising DMEM, 15% ES qualified FCS, 1 mM non-essential amino acids, 0.1 mM 2-mercaptoethanol and 1 mM L-glutamine (all from Invitrogen).

Example 3

Human Embryonic Stem Cells

Human Embryonic Stem Cells (hESCs)-H1 are obtained from Wi Cell Research Institute, Madison, Wis. (Thomson et al. 1998). H1 cells are cultured on irradiated Mouse Embryonic Fibroblasts (MEFs) and maintained in growth media comprising DMEM/F12 media with 20% knockout serum replacement, 1 mM L-glutamine, 1 mM non-essential amino acids, 0.1 mM β-mercaptoethanol and 4 ng/ml basic fibroblast growth factor (bFGF) (all from Invitrogen).

Human Embryonic Kidney (293T) cells are cultured with DMEM and 10% FCS (all from Invitrogen). Cells are incubated at 37° C. with 5% $CO_2$.

Example 4

Wnt3A Conditioned Medium

Wnt-3A conditioned medium (CM) and control CM are prepared from L cells over-expressing and secreting Wnt-3A as described in (Shibamoto et al. 1998).

Example 5

Activation of Wnt Signalling in Mouse Embryonic Stem Cells

Mouse ES cells are cultured continuously for up to 3 weeks on 0.1% gelatin coated dishes in presence of LIF with either growth medium alone (control) or in the presence of 1 µM GSK-3β inhibitor (iGSK-3β, Eli Lilly) or 50% growth media and 50% Wnt-3A CM. Cells are passaged using 0.25% trypsin every 2 days with medium changed every alternate day.

Example 6

Activation of Wnt Signalling in Human Embryonic Stem Cells

Similarly H1 cells are cultured continuously for 3 weeks on irradiated MEFs in presence of bFGF with either growth medium alone (control) or in the presence of 2 µM GSK-3β inhibitor (iGSK-3β, Eli Lilly) or with 50% Wnt-3A CM and 50% growth media. Medium is changed every day and cells are passaged once a week, using collagenase type IV (Gibco).

Example 7

Components of the Wnt Signalling Pathway are Present in Undifferentiated Mouse and Human ES Cells Comprehensive transcriptome profiling of undifferentiated mouse and human ES cells indicated that these cells express all intracellular components of the Wnt signaling pathway including an antagonist, sFRP (Brandenberger et al. 2004). These results suggest that ES cells are poised to respond to Wnt ligands.

Figure 1B:
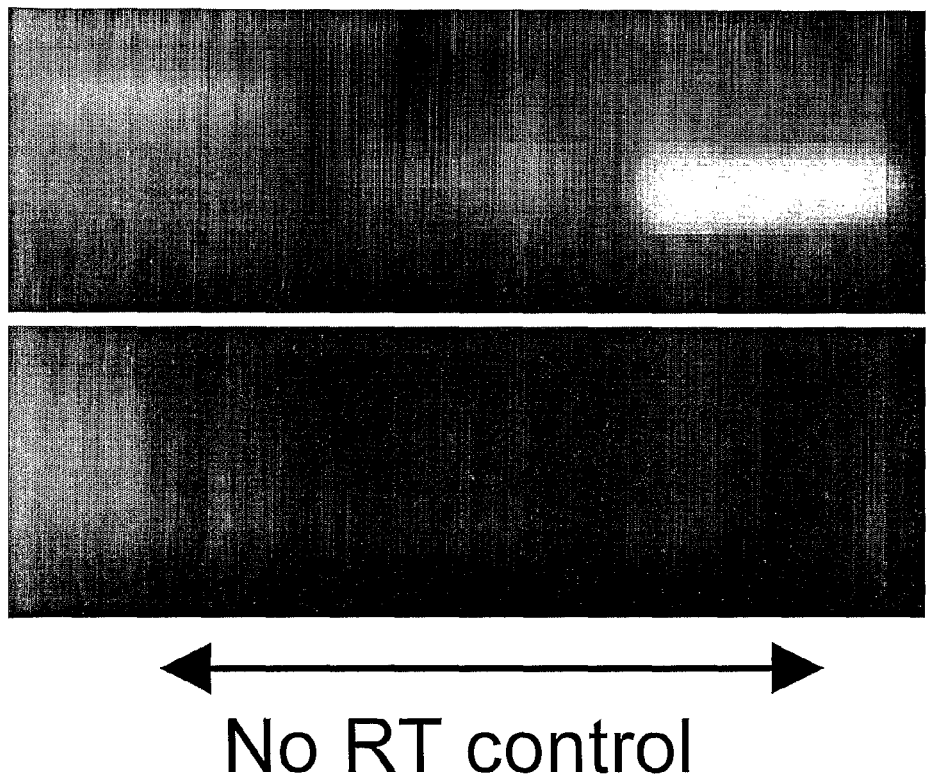
FIG. 1B. Presence of frizzled receptors in E14 cells. RT-PCR analysis performed on undifferentiated E14 cDNA indicates presence of frizzled receptors 2, 5 and 7. No RT control is shown in the bottom panel.

We performed Western blot analysis using undifferentiated mouse and human ES cell lysates and confirmed the presence of Wnt signaling molecules LRP receptor, disheveled and β-catenin and the antagonist sFRP (FIG. 1A). RT PCR analysis performed on undifferentiated E14 RNA confirms the presence of three frizzled (Fz) receptors viz Fz 2, Fz 5 and Fz 7 (FIG. 1B). The presence of signaling proteins and antagonists suggests that ES cells are regulating/inhibiting Wnt signaling as a means to control differentiation.

Example 8

Activity of Wnt Signalling Activators

We evaluated differentiation of ES cells in response to activation of the Wnt pathway. Wnt signaling is induced in two ways; by addition of active Wnt-3A and by addition of a selective inhibitor of GSK-3β.

Wnt3A

Figure 1C:
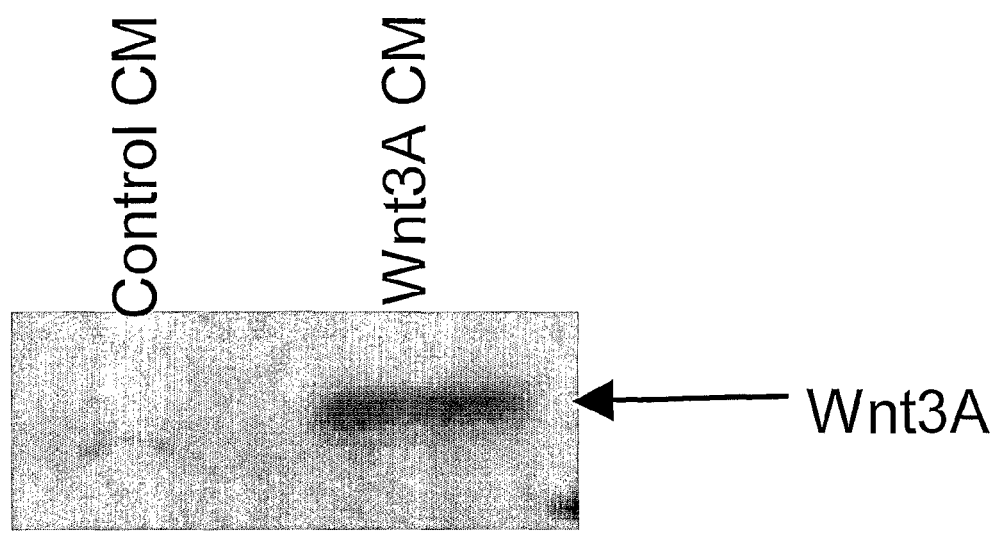
FIG. 1C. Wnt-3A protein is present in the conditioned medium (CM). Western blot analysis on 25 µL of un-concentrated control and Wnt-3A CM using anti-Wnt-3A antibodies.

Wnt-3A conditioned medium (CM) is made from Wnt-3A over-expressing and secreting cells L cells (Shibamoto et al. 1998). Conditioned medium made from L cells is used as control CM. The presence of Wnt-3A protein in the CM is confirmed by western blotting using anti-Wnt-3A antibodies (FIG. 1C).

Figure 1D:
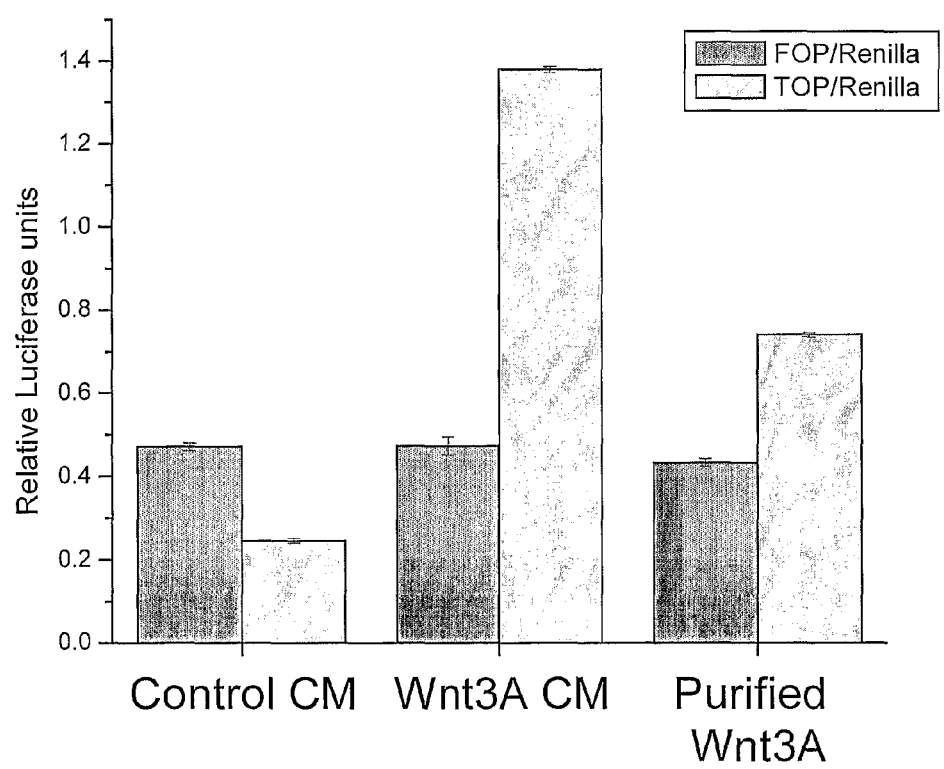
FIG. 1D. Wnt-3A present in the CM is active. Luciferase reporter assays performed using lysates from transiently transfected 293T cells treated with the indicated CM or purified Wnt-3A (10 ng/ml).

To determine the biological activity of Wnt-3A protein present in the CM, luciferase reporter assay system is used in which luciferase expression is under TCF binding sites (TOP flash) or mutated, non-responsive binding sites (FOP Flash). The Wnt-3A CM when added to 293 T cells and mouse ES cells increased the luciferase reporter activity in the TOP FLASH assays (FIG. 1D). The Wnt-3A CM is more active than purified Wnt-3A (100 ng/ml) obtained from commercial sources and control CM from L cells did not have any effect on luciferase assays (FIG. 1D).

iGSK-3β

Figure 1E:
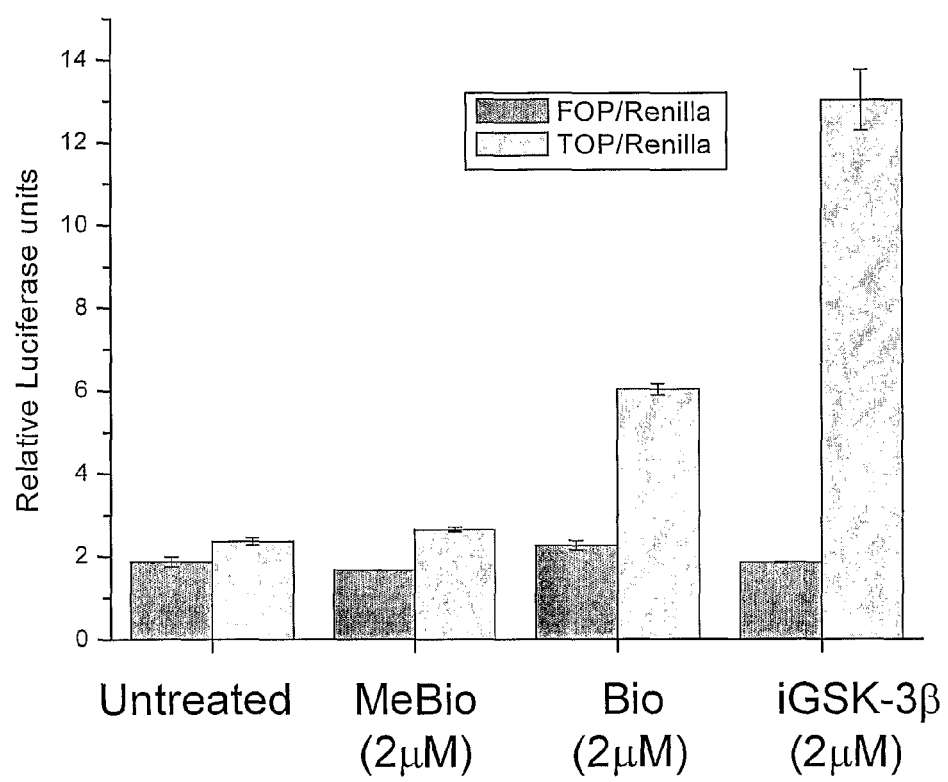
FIG. 1E. Wnt-3A present in CM increases cytoplasmic β-catenin levels. H1 cells are treated with the indicated CM or iGSK-3β and lysates are immunoblotted with anti-active β-catenin antibody.

We used a specific inhibitor of GSK-3β (called iGSK-3β) from Eli Lilly as an intracellular activator of Wnt pathway. Luciferase reporter assays are performed using our iGSK-3β and BIO to compare the specificity and potency of these compounds to activate Wnt pathway (Sato et al. 2004). The iGSK-3β significantly increased luciferase activity (FIG. 1E) in the reporter assays which is 50% more than what is achieved using BIO compound at the same concentration (FIG. 1E) indicating higher potency of the iGSK-3β over BIO.

Example 9

Accumulation of Active β-Catenin

Activation of Wnt pathway leads to accumulation of dephosphorylated β-catenin in the cytoplasm (Shibamoto et al. 1998).

Figure 1F:
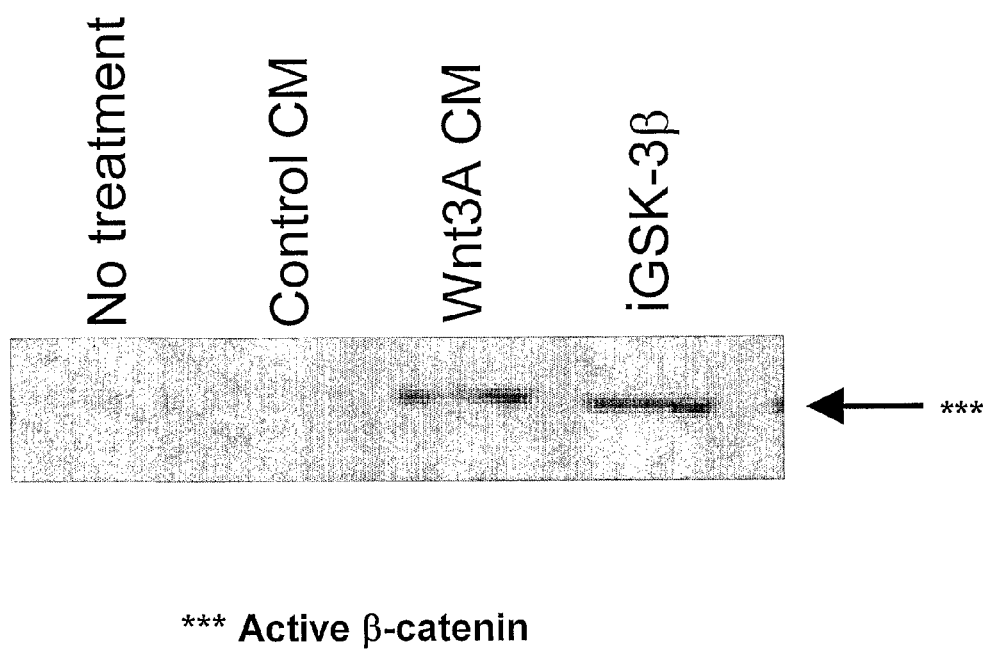
FIG. 1F. Luciferase reporter assays confirm specificity of iGSK-3β to activate Wnt pathway. Assays are done as described in FIG. 1D above. Note that iGSK-3β is more potent than BIO.

Addition of Wnt-3A CM and iGSK-3β on mouse and human ES cells led to accumulation of active β-catenin analyzed by Western blotting using antibody against active/dephosphorylated β-catenin (FIG. 1F). Control CM from L cells did not have any effect in elevating β-catenin levels (FIG. 1F). This indicates that there is active Wnt signaling in ES cells.

Example 10

Short Term Activation of Wnt Signalling Pathway Induces Meso/Endodermal Differentiation of Mouse Embryonic Stem Cells To analyze if activation of Wnt signaling in ES cells will induce differentiation or maintain pluripotency of ES cells, we performed a short time course (days 4-8) of differentiation of E14 cells (mouse embryonic stem cells) using Wnt-3A CM, control CM and iGSK-3β. Real time PCR analysis is performed to assess the changes in marker gene expression.

Figure 1G:
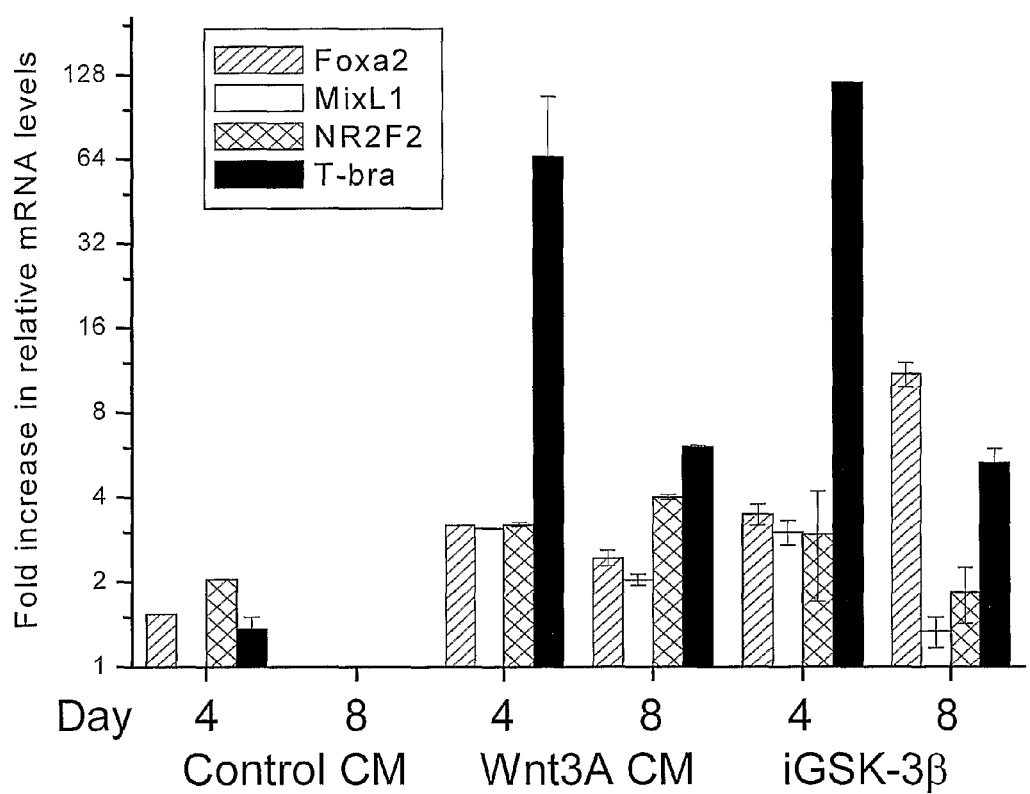
FIG. 1G. Short term activation of Wnt pathway in E14 cells induces differentiation. E14 cells are treated with control CM, Wnt-3A CM, iGSK-3β separately for 4-8 days as described in methods. Real-time PCR analysis of marker gene expression is shown.

Addition of Wnt-3A CM and iGSK-3β to E14 cells induces differentiation of cells as evidenced by (5-100 fold) up-regulation of markers of differentiation (Mixl1, Foxa2, T-brachyury) as early as day 4 (FIG. 1G). Mixl1 has been implicated in endoderm development (Hart et al. 2002). Since the differentiating cells expressed both Foxa2 and T-brachyury, they could be differentiating towards bi-potential mesendodermal cells (Kubo et al. 2004). The control CM had no effect on inducing differentiation of E14 cells even at day 8 indicating that the differentiation of E14 cells observed is due to Wnt-3A present in the CM.

Short term (4 day) treatment of human ES cells gave similar results and again the control CM had no effect on inducing differentiation of human ES cells. These results suggest that the biologically active Wnt-3A present in the CM induces meso/endodermal differentiation of ES cells and we explored this further by performing a long term activation of the Wnt pathway in mouse and human ES cells.

Example 11

Long Term Activation of Wnt Signalling Pathway Induces Meso/Endodermal Differentiation of Mouse Embryonic Stem Cells (21 Days)

In order to establish the effect of long term activation of Wnt pathway in undifferentiated ES cells, feeder free E14 cells (mouse embryonic stem cells) are treated with Wnt-3A and 1 µM iGSK-3β separately for three weeks.

To track the differentiation status of these treated cells, real time PCR analysis is performed using untreated E14 cDNA as control and data plotted is fold increase over untreated E14 cells. We did not get differentiation along ectoderm/neuroectoderm since expression of Nestin, Sox4, Pax6 is not observed.

Figure 2A:
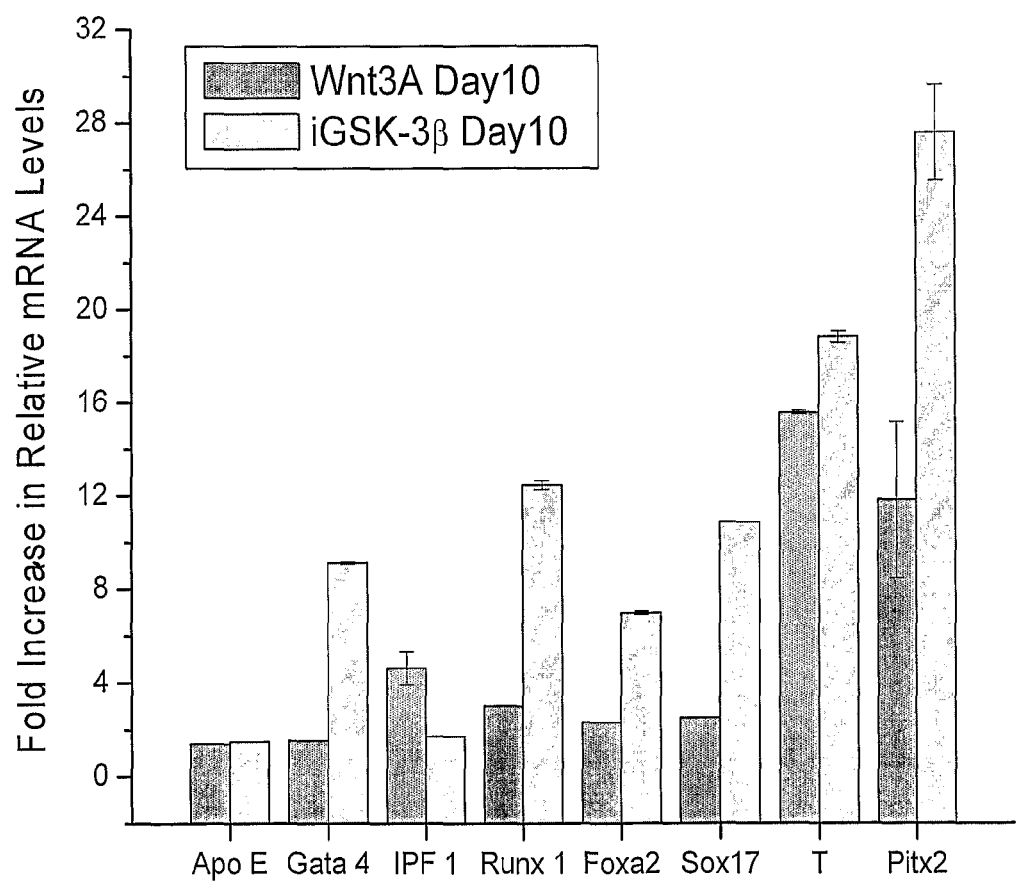
FIG. 2A shows real-time PCR analysis using key lineage specific marker gene primers (ABI) after 10 days of treatment.

A substantial increase (10-100 fold) in expression of many mesoderm (T-brachyury, Runx1, Pitx2) and endoderm (Gata4, Foxa2, Sox17) specific transcription factors is seen at both day 10 and day 21 (FIGS. 2A,B). 20-100 fold up-regulation of T-brachyury and Pitx2 (FIGS. 2A, B) which are direct targets of β-catenin indicated that indeed Wnt pathway has been activated in both the treated cells. Up-regulation of Pitx2, indicated strong mesodermal potential. In *Xenopus*, Veg T induces expression of Sox17, Sox17 and β-catenin then cooperate to regulate transcription of endodermal genes such as Foxa2, Edd, Foxa1. (Sinner D et al. 2004). In accordance with this, in response to Wnt activation in our cells, T-brachyury (VegT ortholog) could be regulating endodermal genes such as Foxa2 via Sox17.

Figure 2B:
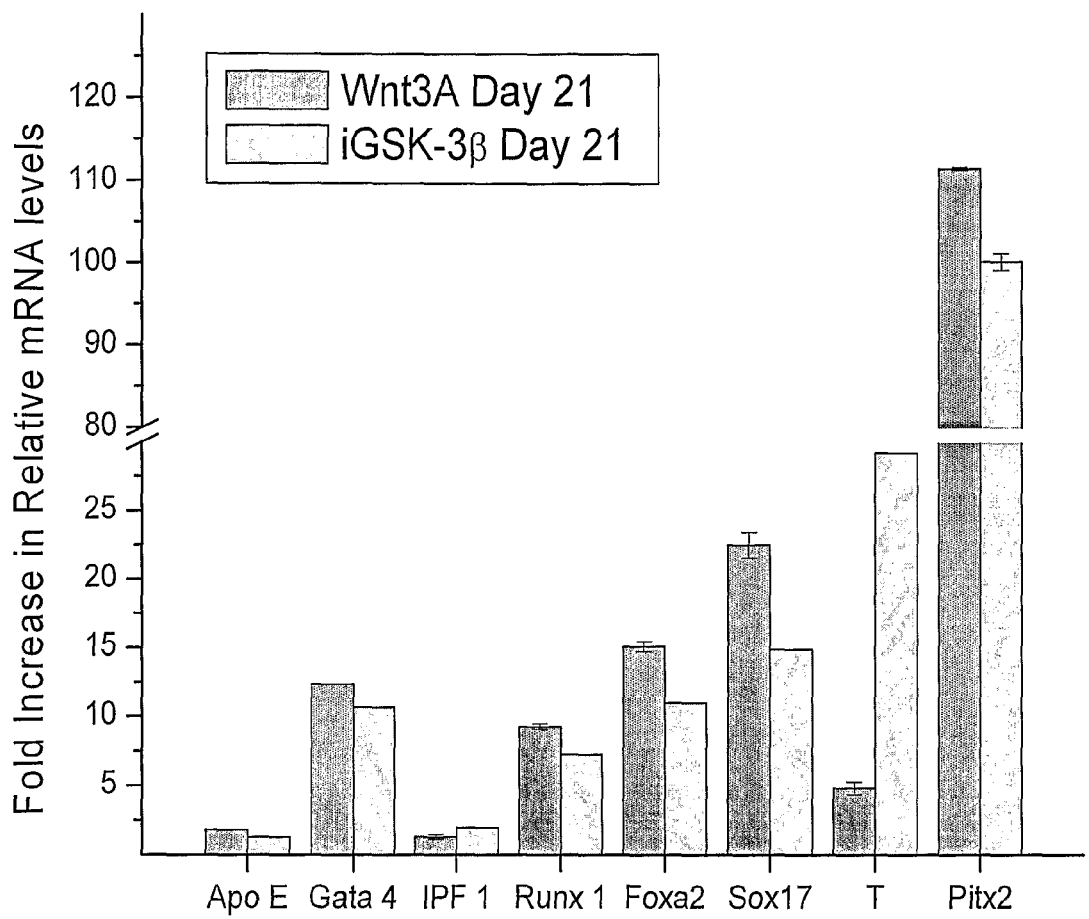
FIG. 2B shows real-time PCR analysis using key lineage specific marker gene primers (ABI) after 21 days of treatment.

At day 10 iGSK-3β treated cells showed more increase in levels of marker gene expression compared to Wnt-3A treated cells (FIG. 2A), however by day 21, both cells showed a comparable increase in marker gene expression (FIG. 2B). At both day 10 and 21 there is a strong up-regulation (10-100 fold) of Foxa2 and Sox17 (FIGS. 2A,B), markers of definitive endoderm which can also be expressed by visceral endoderm (Keller 2005). 20 fold up-regulation of T-brachyury (which is not expressed in visceral endoderm) in the same cells (FIG. 2A and FIG. 2B) confirmed that the cells are differentiating along definitive endoderm (Keller 2005).

Lack of induction of IPF1 indicated that cells are not differentiating along pancreatic endoderm. T-brachyury, transcription factors of GATA family are usually expressed by the bipotential mesendodermal progenitor cells early in differentiation. These progenitors later specify either mesoderm or endoderm by expressing either T-brachyury, NRx2.5 and twist or Foxa2, Sox17 and GATA4-6 respectively in response to appropriate stimuli, suggesting that the final fate of our treated cells can be further manipulated to specific cell type (reviewed in Technau and Scholz 2003).

Figure 2C:
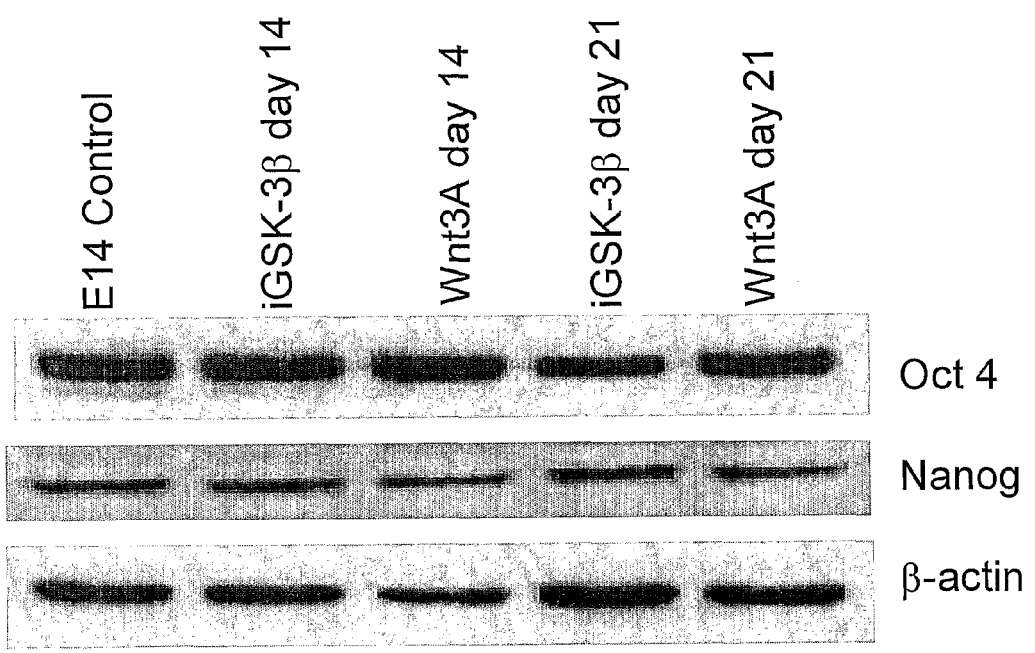
FIG. 2C. Differentiating E14 cells retain pluripotency markers. Western blot analysis performed on cell lysates at the indicated days using Oct4 and Nanog antibodies. B-actin is shown as a loading control.

By day 21 Wnt-3A and iGSK-3β treated cells showed primarily meso/endodermal differentiation, however, the Wnt-3A treated cells had reduced (5 fold) T-brachyury and increased (110 fold) Pitx2 expression compared to iGSK-3β treated cells. Thus, although canonical Wnt pathway is activated in both the cases there are subtle difference in the way cells respond to different activators. Morphologically, the E14 cells treated with Wnt-3A and iGSK-3β looked different from untreated cells. The treated cells are more flat and spread out as compared to typical compact morphology of the undifferentiated ES cells. iGSK-3β treated cells showed distinct signs of differentiation such as presence of individual cells with distinct shape and the appearance of embryoid body like structures (FIG. 2C).

Figure 2D:
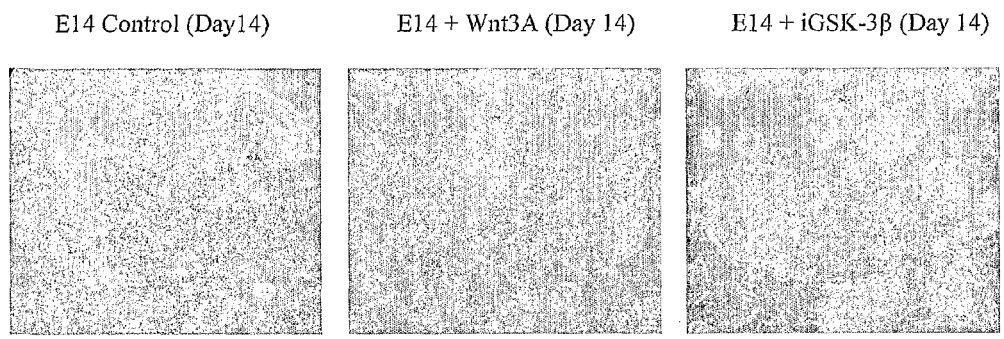
FIG. 2D. Bright field pictures of E14 cells (control) and treated with Wnt-3A and iGSK-3β for 14 days in culture. The entire time course experiment is repeated thrice and obtained reproducible results. Results of one experiment are shown here.

Differentiation of ES cells typically results in down-regulation of pluripotency markers-Oct4 and Nanog. By Western blot analysis (FIG. 2D) and real time PCR, undifferentiated E14 cells expressed high levels of Oct4 and Nanog however as cells differentiated in response to Wnt activation, they retained Oct4 and Nanog even at day 21 (FIG. 2D). Presence of Nanog in the differentiating cells once again rules out differentiation along visceral endoderm (Mitsui et al. 2004). Presence of Oct4 could be responsible for suppression of extra embryonic differentiation (Hay et al. 2004).

Example 11A

Long Term Activation of Wnt Signalling Pathway Induces Meso/Endodermal Differentiation of Mouse Embryonic Stem Cells (30 Days)

The experiments described above in Example 11 are repeated for a time frame of 30 days. Identical results are obtained.

The expression of pluripotency markers together with markers of mesoderm and endoderm indicates that sustained Wnt signaling induces differentiation of undifferentiated E14 cells to a multipotent population with meso/endodermal specification. Previously, Rathjen et al. 1999 have reported similar findings when ES cells are induced to differentiate with HepG2 CM.

Example 12

Sustained Wnt Pathway Activation in Human Embryonic Stem Cells Induces Meso/Endodermal Differentiation Mouse and human ES cells although similar in many ways they have numerous important differences including lack of active LIF signaling pathway in human ES cells (Ginis et al. 2004).

To establish the role of long term activation of Wnt pathway in human ES cells, H1 cells (Wi cells) cultured on irradiated mouse embryonic fibroblasts are treated with Wnt-3A and iGSK-3β separately for 21 days. The differentiation status of the treated cells is analyzed by real time PCR, Western blotting and FACS analysis. Real time PCR is performed using untreated H1 cDNA as control and data plotted is fold increase over untreated H1 cells.

Figure 3A:
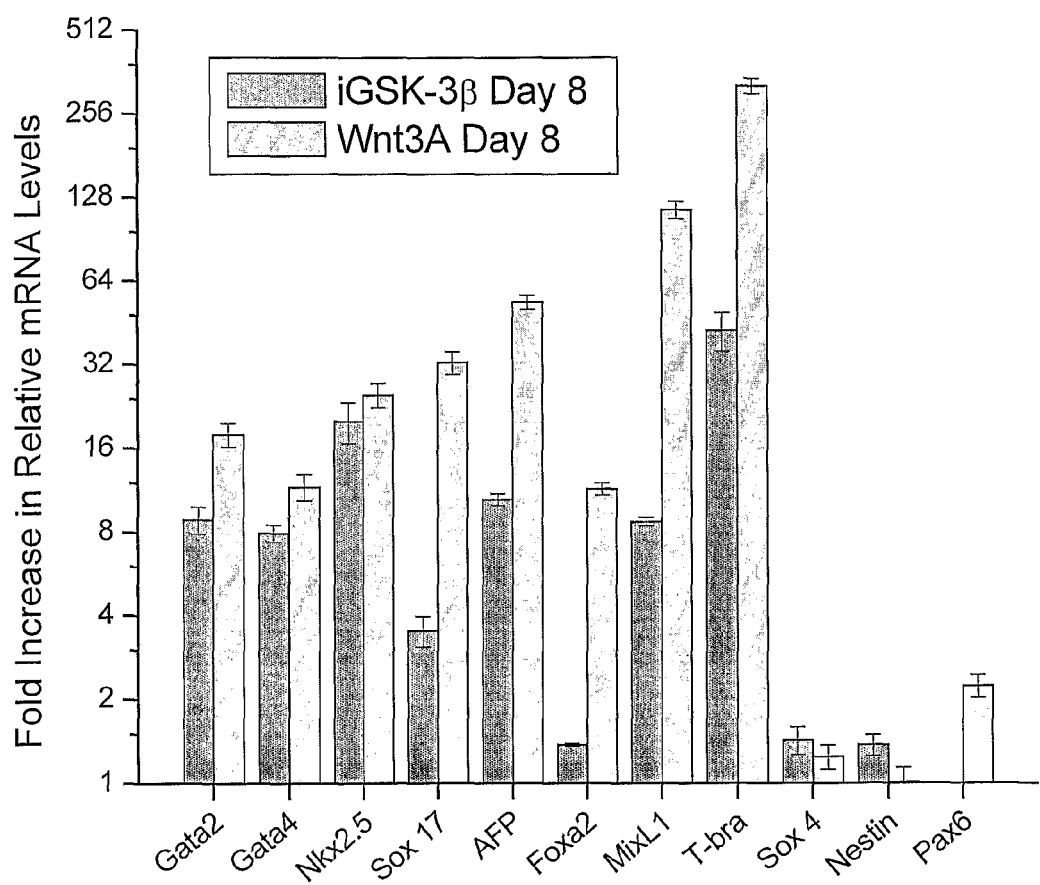
FIG. 3A shows real-time PCR analysis performed on RNA extracted from differentiating H1 cells using key lineage specific marker gene primers (ABI) after 8 days of treatment.
Figure 3B:
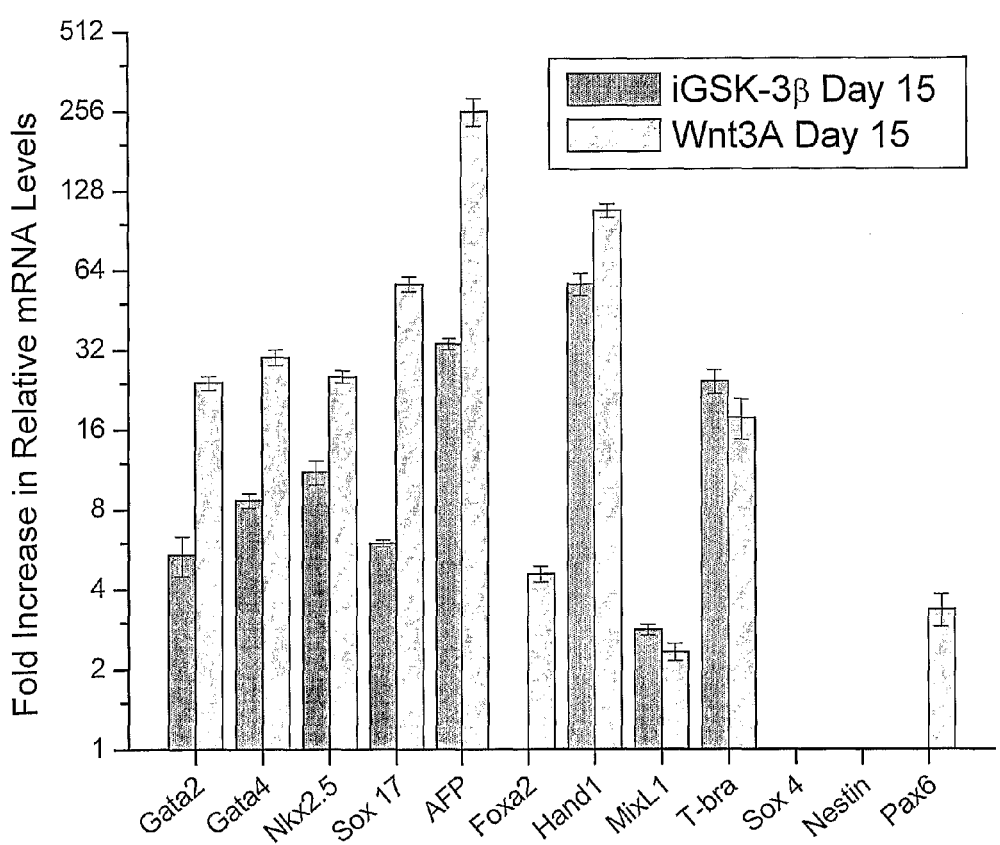
FIG. 3B shows real-time PCR analysis performed on RNA extracted from differentiating H1 cells using key lineage specific marker gene primers (ABI) after 15 days of treatment.

The absolute increase in mRNA levels for marker genes in H1 cells at day 8 (FIG. 3A) is (up to 500 fold) much stronger than mouse ES cells (up to 30 fold) treated with the same compounds for similar time points (FIG. 2A) indicating higher sensitivity of human ES cells to Wnt pathway activation. In response to Wnt pathway activation, H1 cells did not express markers indicative of ectoderm/neuroectoderm viz Pax6, Sox4 and nestin even at day 15 (FIG. 3A and FIG. 3B). 10-500 fold up regulation of T-brachyury, Gata 2, NRx2.5, Hand1 indicated mesodermal differentiation by day 8 (FIG. 3A). However, the differentiating cells had increased (up to 100 fold) levels of endodermal markers such as Foxa2, AFP, Gata4, Sox17 at day 8 (FIG. 3B), thus indicating that cells are differentiating along both these lineages.

Figure 3C:
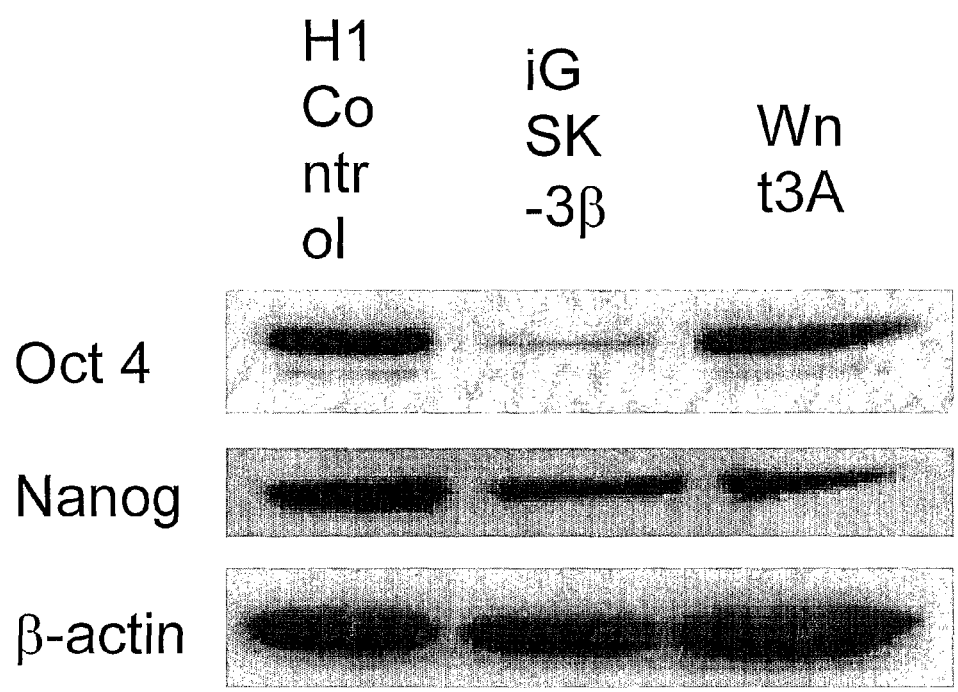
FIG. 3C. Differentiating H1 cells retain pluripotency markers. Western blot analysis is performed on cell lysates at the indicated days using Oct-4 and Nanog antibodies. B-actin is shown as a loading control.

Mixl1 is usually expressed early in endoderm formation (Hart et al 2002, Shivdasani 2002) and is most critical for endodermal differentiation. Sustained Wnt activation induced up to 100 fold expression of Mixl1 in the H1 cells within 8 days and as expected the expression had reduced to 5 fold by day 15. The differentiating H1 cells retained pluripotency markers—Oct4 and Nanog (FIG. 3C) thus ruling out extra embryonic or visceral endodermal differentiation (Hay et al 2004, Mitsui et al 2003). Levels of Nanog did not decrease compared to control H1 cells although there is a partial decrease in Oct4 levels in iGSK-3β treated H1 cells (FIG. 3C). The presence of pluripotency markers along with markers of differentiation again suggests that sustained Wnt signaling induces differentiation of H1 cells towards meso/endoderm.

Figure 3D:
FIG. 3D. Bright field pictures of H1 cells (control) and treated with Wnt-3A and iGSK-3β for 15 days in culture.
Figure 3D:
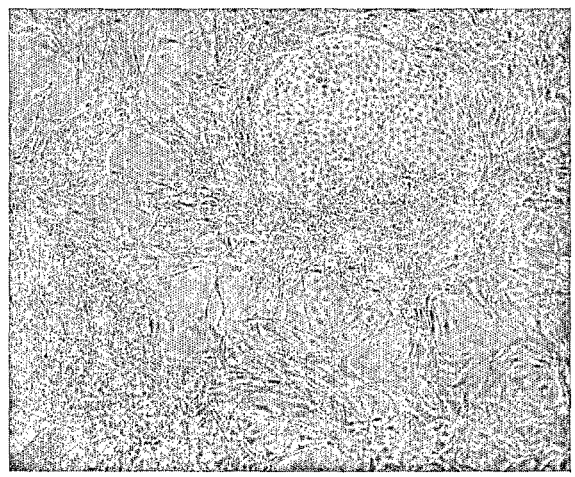
Figure 3D:
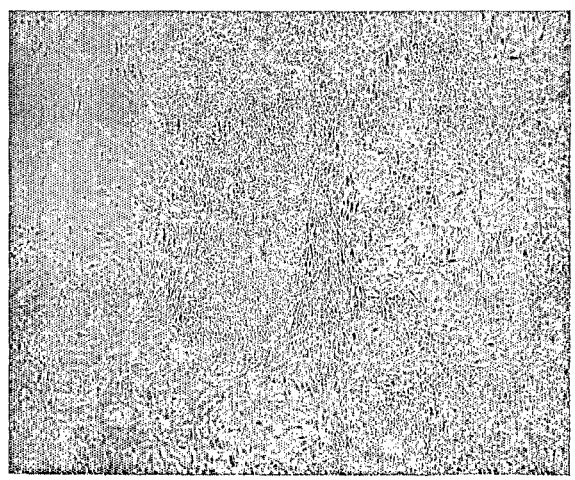
Figure 4A:
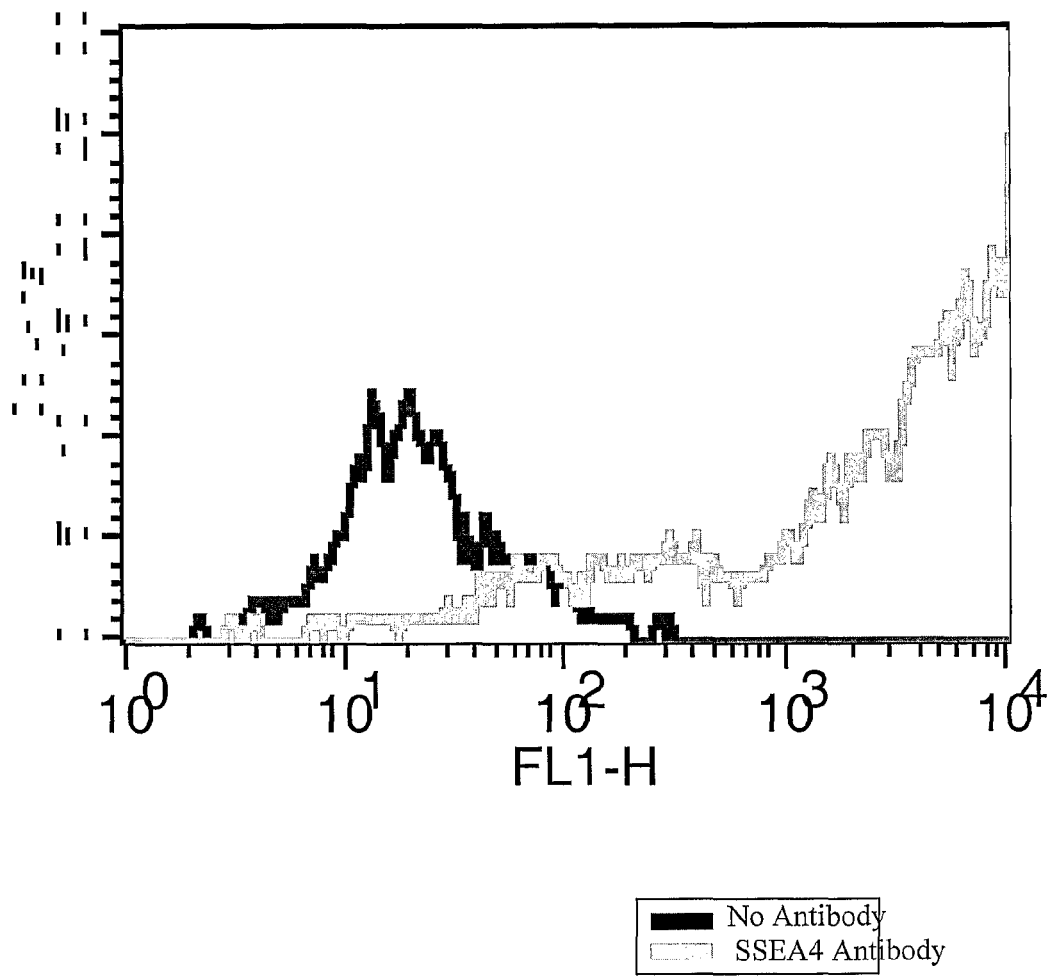
FIG. 4A-4C. Long term activation of the Wnt pathway in H1 cells leads to loss of SSEA 4 staining. H1 cells are treated with control CM (FIG. 4A), Wnt-3A CM (FIG. 4B), iGSK-3β (FIG. 4C) separately for 21 days as described in methods. On day 21 cells are trypsinized and stained with SSEA4 antibody (DHSB) as described in methods. FACS analysis is performed using FACS Bioanalyzer (BD).
Figure 4B:
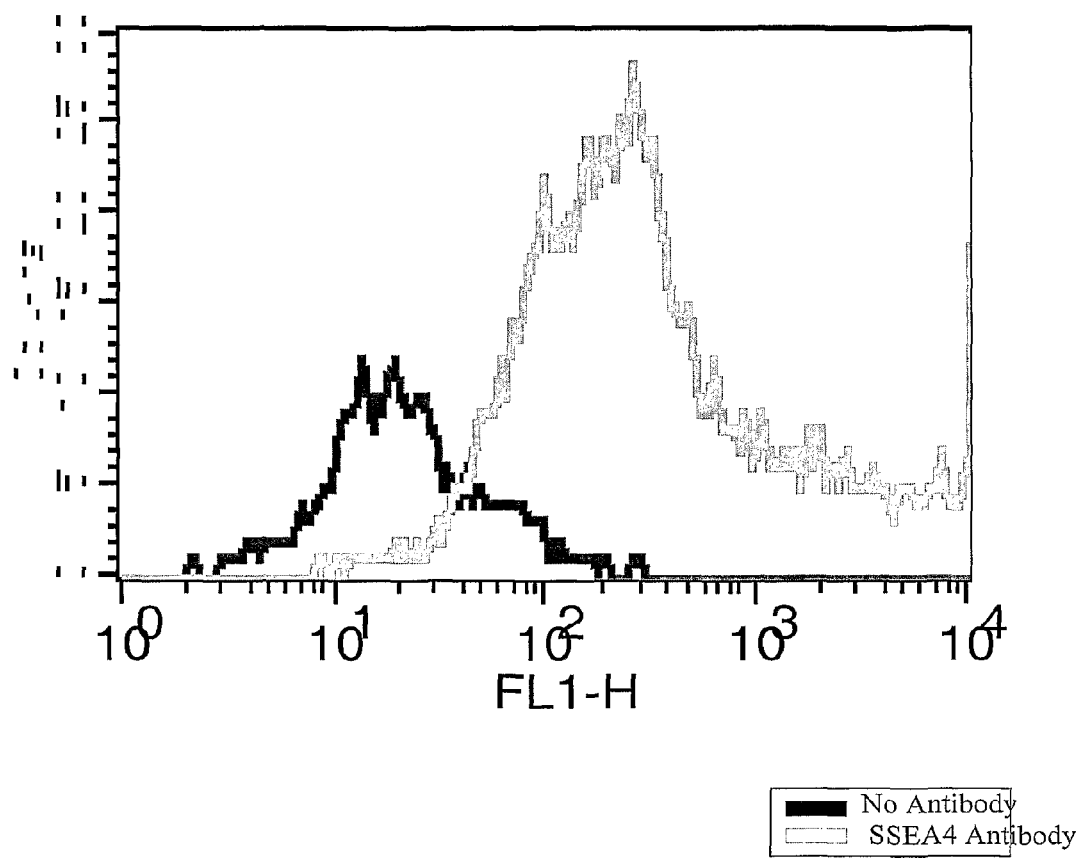
Figure 4C:
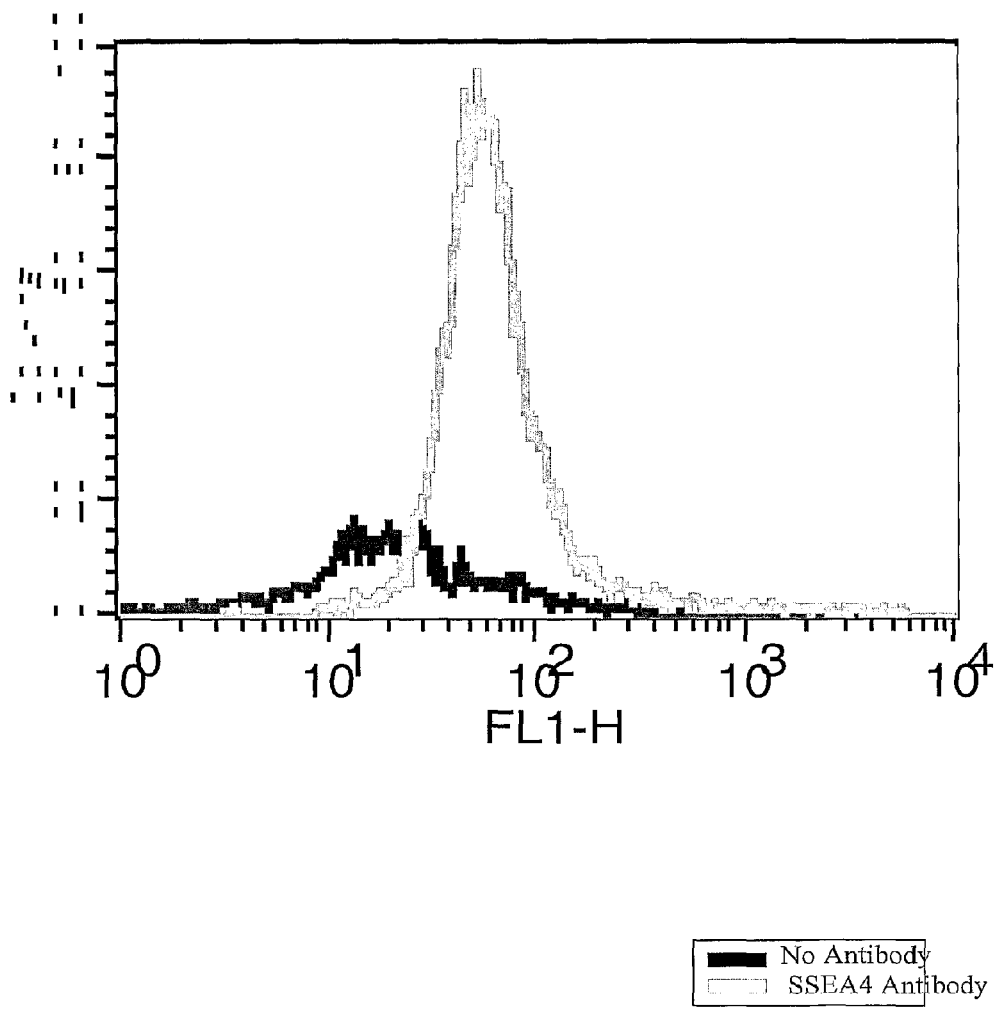
Figure 5:
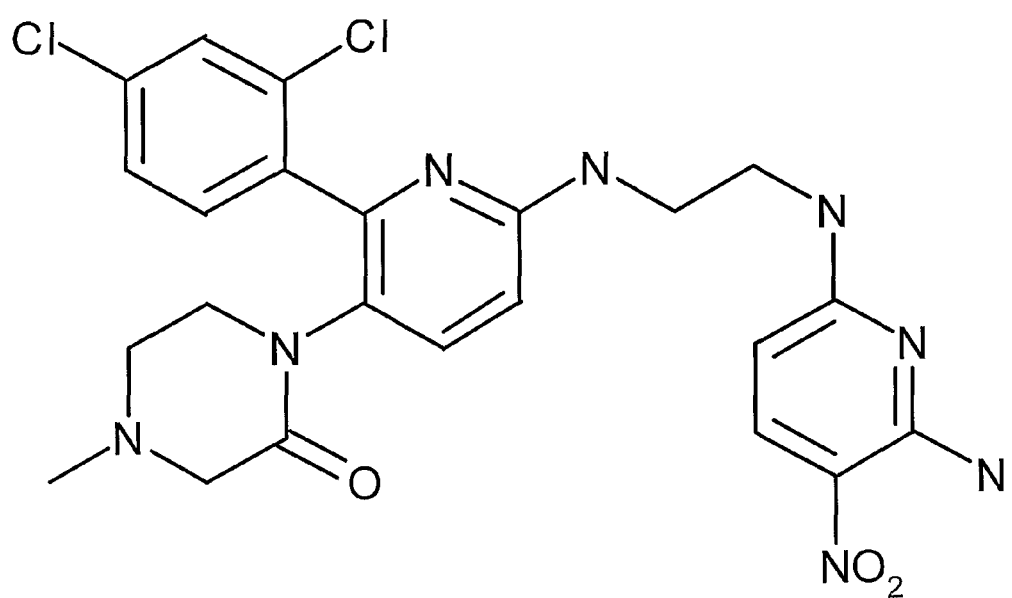
FIG. 5 shows the structure of iGSK-3β (Eli Lilly).

Morphologically, H1 cells show distinct signs of differentiation such as loss of a tight colony morphology and appearance of cells with a distinct shape within a colony (FIG. 3D). To analyze the percentage of pluripotent cells remaining at the end of day 21, we performed FACS analysis on cells stained with an antibody against pluripotency specific cell surface marker, SSEA4. As seen in FIG. 4, untreated H1 cells showed a distinct peak of SSEA4 stained cells (FIG. 4A). However, upon Wnt activation there is a significant loss in SSEA4 stained cells in Wnt-3A and even more strongly in iGSK-3β treated cells (FIGS. 4B & 4C respectively). Lack of SSEA4 stained cells again confirmed that activation of Wnt pathway induces differentiation of ES cells.

In contrast to studies by (Sato et al. 2004) that suggest the involvement of Wnt pathway in maintaining pluripotency, our data demonstrate conclusively that sustained activation of Wnt pathway induces differentiation of ES cells.

Example 13

Expression of Constitutively Active Beta-Catenin Mutants in Embryonic Stem (ES) Cells A variety of beta-catenin mutants having constitutive activity are found in various human cancers. These mutations are very specific and are in residues in the aminoterminal domain of the protein. Such residues can become phosphorylated and play a role in the destabilization of the protein. The mutations block phosphorylation and therefore lead to increased stability of the beta-catenin protein.

Wnt signaling and cancer. Genes Dev. 2000 Aug. 1; 14(15):1837-51 shows a table which lists the frequency and the positions of point mutations in beta catenin. Site directed mutagenesis of each of the listed amino acids in the table from Polakis (2000) to alanine is conducted to produce constitutively active beta-catenin mutants. A deletion mutant of beta-catenin lacking N-terminal 50-90 amino acids (i.e., lacking all the residues which are phosphorylated by GSK-3b, APC, Dsh complex) is also constructed.

Nucleic acid constructs encoding the mutants are subcloned into a mammalian transfection vector. The resulting construct is transfected into mammalian, mouse and human cells using lipids such as Lipofectamine. Transfection is also carried out using electroporation according to the manufacturer's protocol. Host cells transfected or electroporated with the expression constructs over-express mutant constitutively active beta-catenin. Stable ES cell lines which express only the mutant forms of b-catenin are also generated.

Development of ES cells along the mesodermal and endodermal pathway is assessed and observed using markers of mesodermal and endodermal differentiation.

The promise of ES cells in regenerative medicine lies in their potential to give rise to any type of cell within the body. However, since the ES cells can spontaneously differentiate (e.g. embryoid body formation) into multiple lineages, the major obstacle in generating specific types of cells for therapeutic use is the difficulty in getting a homogenous and pure population of differentiated cells. Understanding lineage commitment at early stage is crucial to use of ES cells in regenerative medicine.

Here, we provide the first conclusive evidence of the role of Wnt pathway in meso/endoderm development. Since these meso/endodermal cells can be moulded into either mesoderm or endoderm by activation of specific pathways, the ultimate fate of these cells can indeed be fine tuned to make the desired lineage specific cell type useful in regenerative medicine.

Example 14

Isolation of the Single Cell Clones from a Population of mES Cells with Sustained Wnt Pathway Activation Using GSK-3b Inhibitor Mouse ES cells are treated with GSK3b inhibitor in continuous culture to activate Wnt pathway. To isolate single cell clones from the population, we used BD FACS Aria Cell Sorter.

Briefly, mouse embryonic feeders are seeded onto a 96 well dish. GSK3b inhibitor treated mouse ES cells are trypsinized to obtain single cell suspension and single cell sorting is performed using FACS Aria cell Sorter. A single mES cell is seeded onto each well of a 96-well dish in which feeder cells (mouse embryo fibroblasts) are already established.

After sorting, the ES cells are grown for 2 weeks in presence of GSK3b inhibitor and are further expanded from 96 well dishes to 10 cm plates gradually without feeders.

Example 15

Analysis of Single Cell Clones

RNA is extracted from the single cells clones and analysed by Q-RT-PCR to confirm up-regulation of a variety of meso/endodermal markers.

Figure 8:
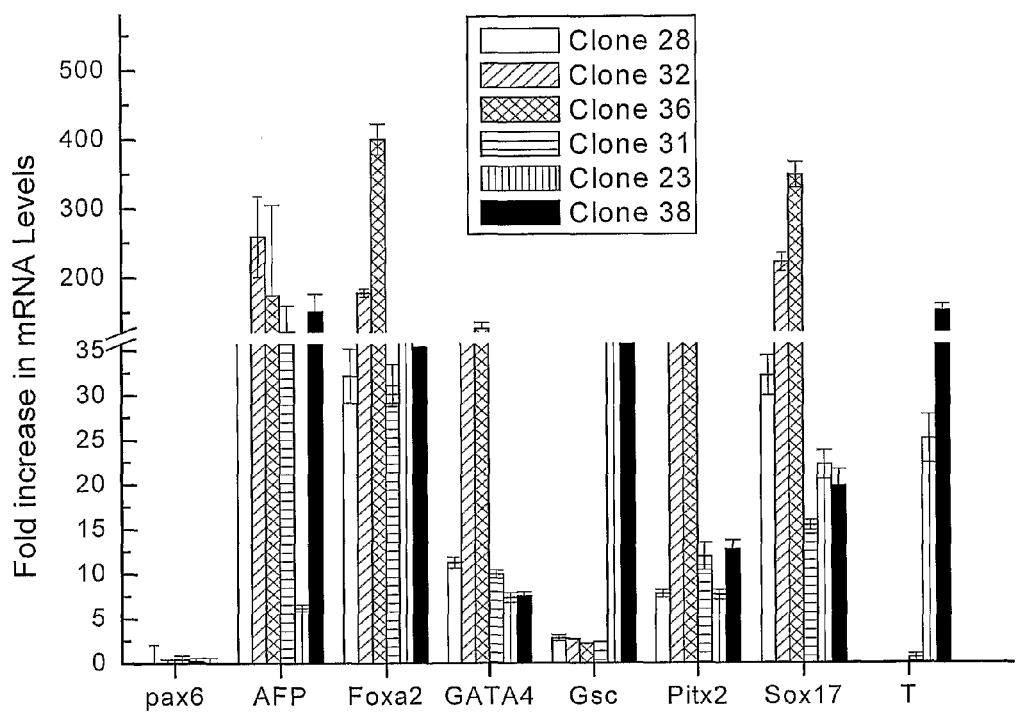
FIG. 8 shows results from Real-Time PCR analysis of the mES clones.

As shown in FIG. 8, key meso/endodermal markers such as T-brachyury, Foxa2, Sox17, goosecoid, Gata4, Gata6, AFP, Pitx2 are up-regulated by as much as 400 fold.

Figure 9:
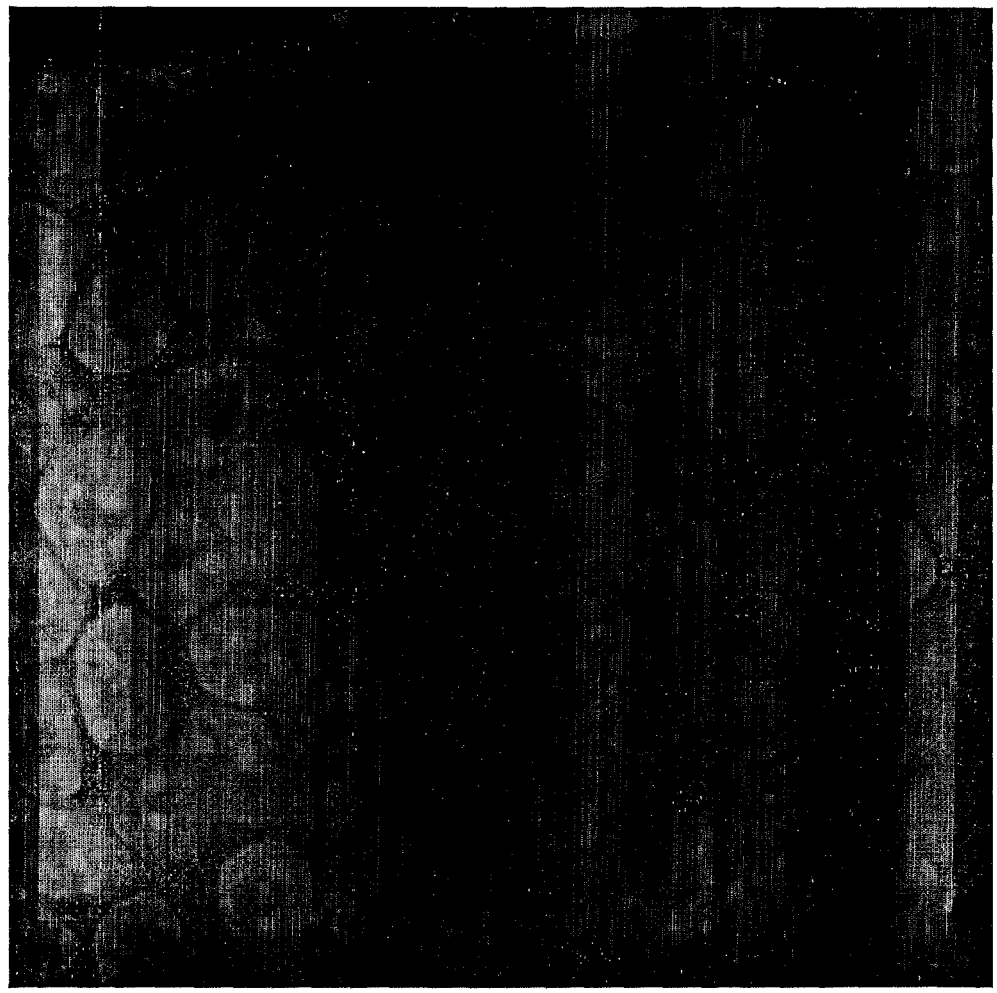
FIG. 9 shows results from immunostaining for markers of differentiation using mES Clone 23.
Figure 9:
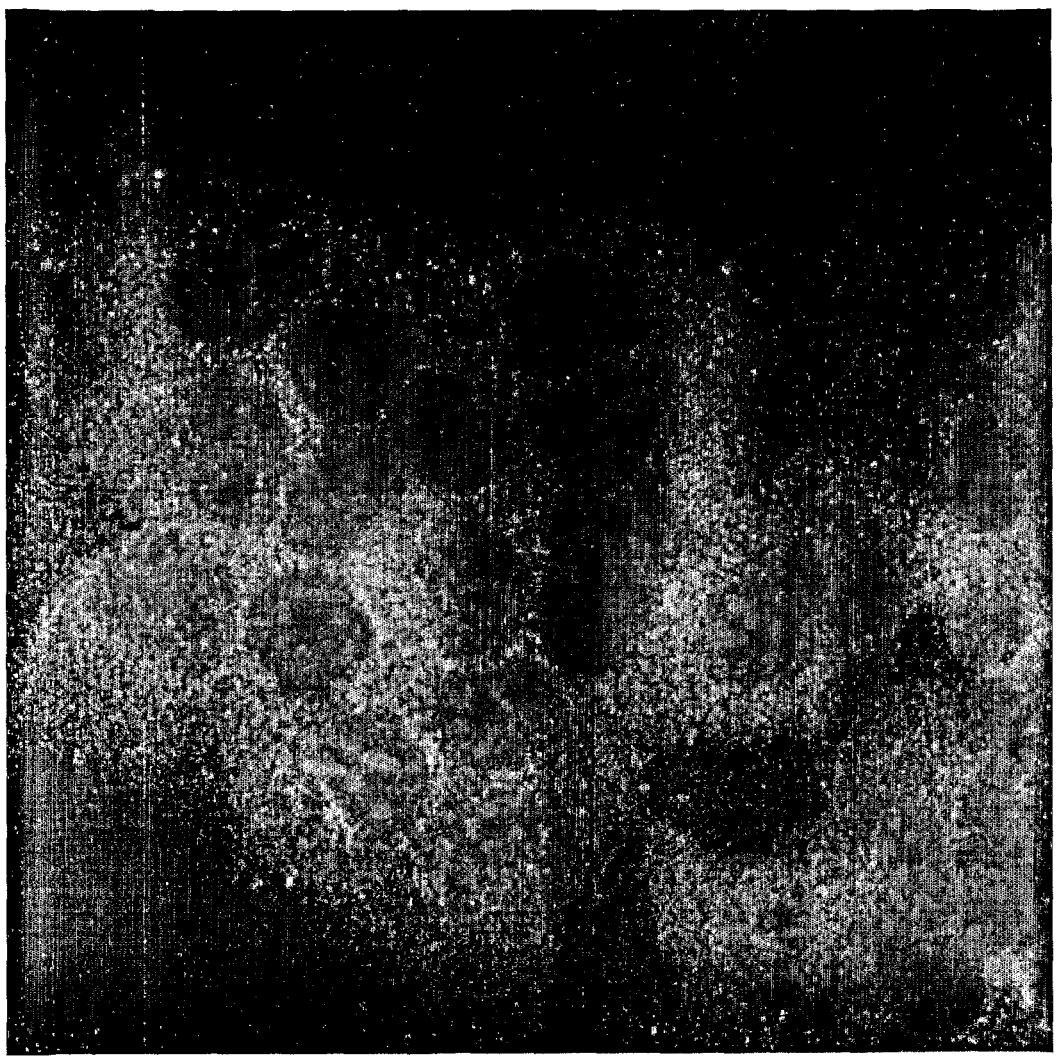
Figure 9:
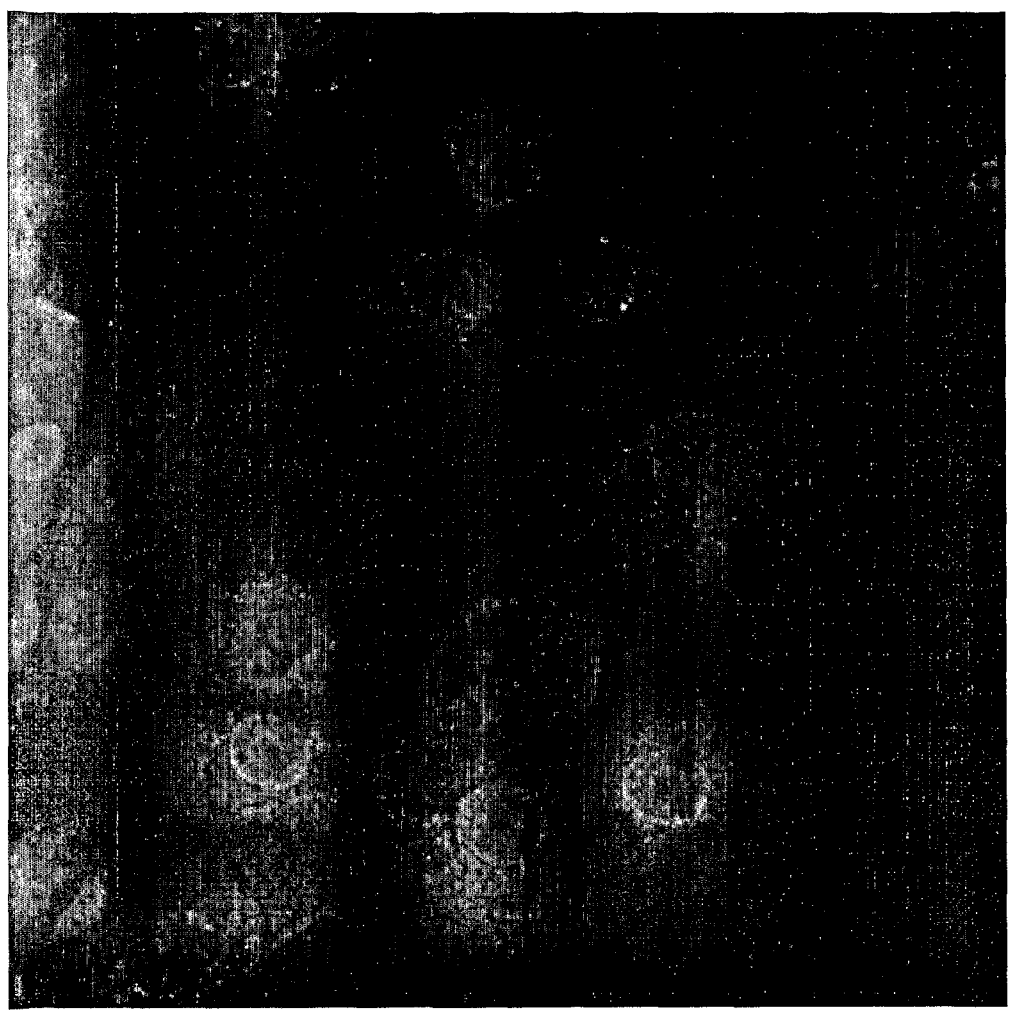

We performed immunocytochemistry to confirm up-regulation of some of these markers of differentiation (see FIG. 9).

We next analyzed the potential of the clones to differentiate into mesodermal cell types such as endothelial, cardiac, osteogenic and chondrogenic.

Example 16

Endothelial Differentiation

Wnt pathway activated clones are trypsinized and aggregated to form embryoid bodies (EB) and plated in methyl cellulose for 11 days in the presence of growth factors required for endothelial cell formation (Choi K et al 1998, *Development* 125:725-732 Balconi et al 2000, *Atherioscler Thromb Vasc Biol* 20:1443-1451).

On day 11, the EBs are harvested and re-suspended in collagen gel in presence and absence of growth factors. The appearance of endothelial sprouts is assessed after 2-3 days of culture in collagen gel.

Figure 10:
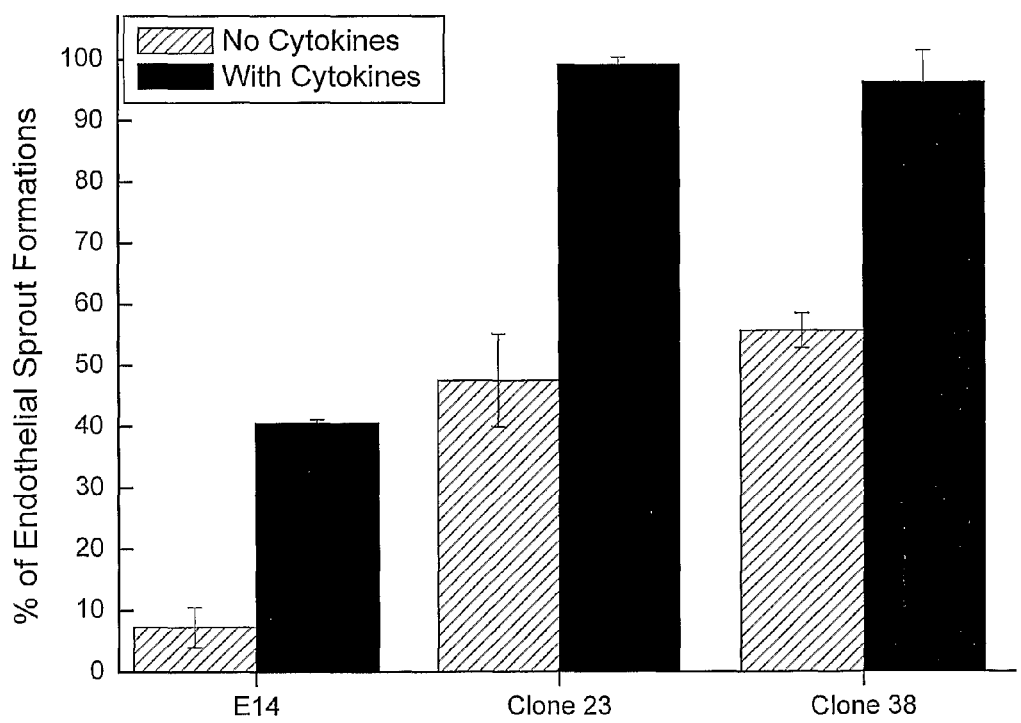
FIG. 10 shows results from analysis of differentiation of E14 cells and the clones along Endothelial lineage

We found that clones 23 and 38 had significantly more sprouted EBs than control untreated E14 cells (FIG. 10).

Figure 11:
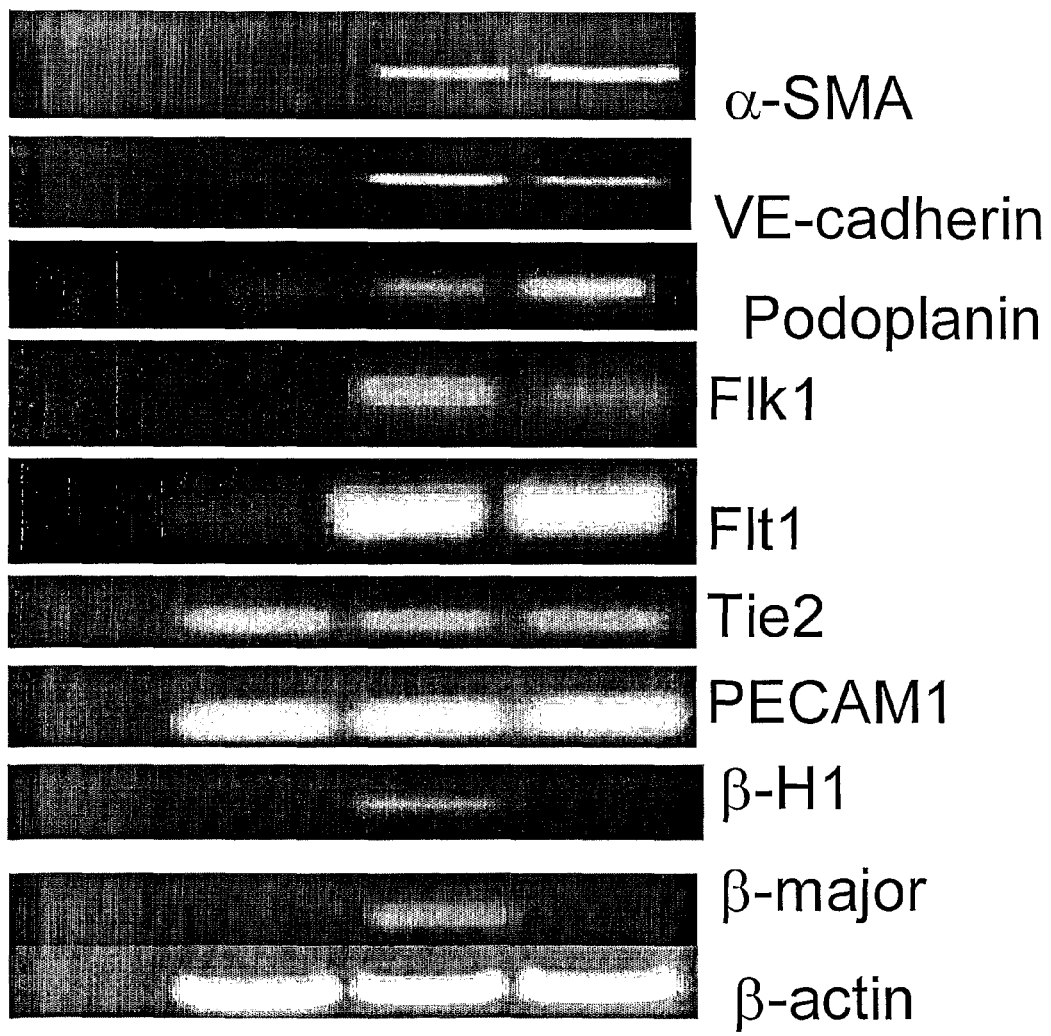
FIG. 11 shows results from RT PCR analysis for markers of endothelial lineage for Clone # 23 and 38.

Sprouted EBs are collected after 3-4 days and RNA is extracted to confirm up-regulation of key endothelial markers (FIG. 11). The sprouted EBs are also seeded onto chamber slides and immuno staining is performed using antibodies against key markers of endothelial cells.

Example 17

Cardiac Differentiation

Clones are trypsinized, and are re-suspended at 25,000 cells per ml. EBs are made by the well-established hanging drop method using Petri dishes for 2 days. At the end of 2 days, EBs are collected and re-suspended in medium for 3 days. At the end of 3 days, EBs are allowed to attach onto gelatine coated dishes. Potential of cardiac lineage is scored based on observation of 3 or more beating areas in each EB.

Figure 12:
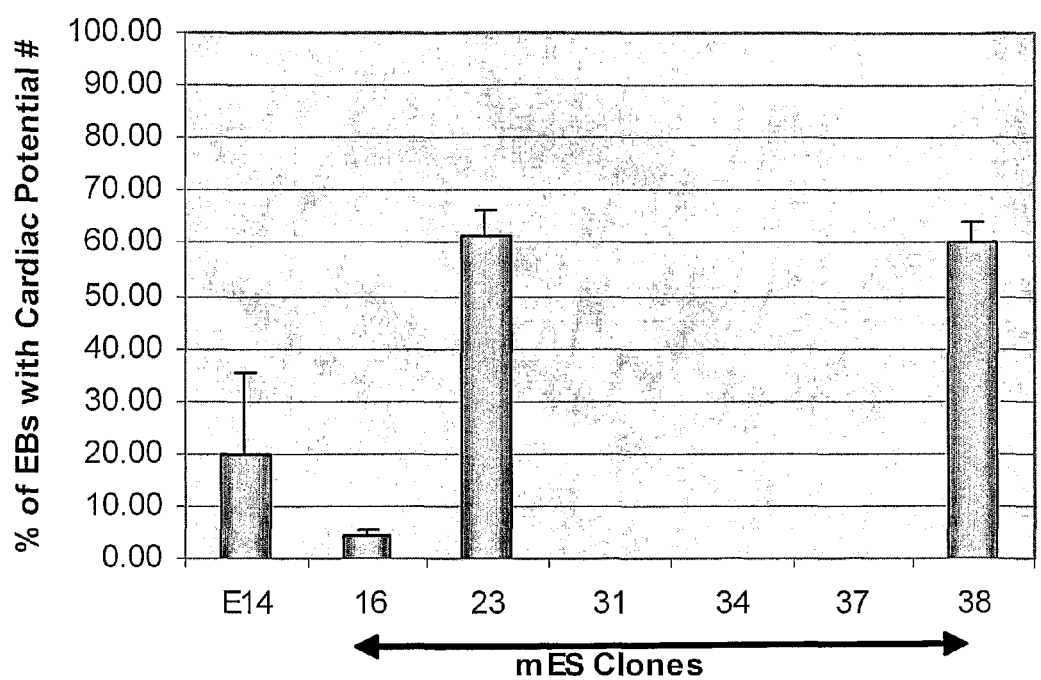
FIG. 12 shows results from analysis of differentiation of E14 cells and the clones along Cardiac lineage.

Clones 23 and 38 showed higher percentage of beating EBs than control E14 cells (FIG. 12).

Example 18

Osteogenic and Chondrogenic Differentiation

Clones are seeded onto gelatine coated dishes and are cultured for 3 weeks in presence of a variety of growth factors required for osteogenesis and chondrogenesis as described in (Zuk P A et al 2001, *Tissue Engineering* Vol 7, number 2, pg 211-227). At the end of 3 weeks, RNA is extracted and differentiation status is confirmed using RT-PCR and staining protocols as described in Zuk et al.

Example 19

Microarray Analysis

We performed Microarray analysis using RNA extracted from E14 cells and clones Using Ilumina mouse gene expression analysis tools. Data obtained are analyzed using Gene Spring software using FDR (False Discovery Rate) of 0.03. The data generated is statistically validated using Mann-Whitney U test. The statistically significant genes were then evaluated for functional and lieneage relationships by comparison to the PANTHER gene onology database (Applied Biosystems).

We found 700 genes which are (statistically) significantly changed (up and down regulated) in the clones as compared the starting undifferentiated ES cells. Analysis of the up-regulated genes indicated that most of them belong to a variety of developmental processes such as mesoderm induction, skeletal development, ECM signalling, Growth factor Signaling, Cell Adhesion. (see Table E1 below).

TABLE E1

Microarray Analysis: Table A shows the different pathways and processes that are significantly upregulated of the GSK3b inhibitor treated clones as compared to E14 control.

| | Total Genes on Array | No of Genes that fall within the pathway | No of Genes expected to fall within the pathway | P value |
|---|---|---|---|---|
| Biological Process | | | | |
| Cell communication | 359 | 74 | 27.63 | 0.0000 |
| Signal transduction | 1140 | 153 | 87.74 | 0.0000 |
| Developmental processes | 824 | 109 | 63.42 | 0.0000 |
| Cell surface receptor mediated signal transduction | 488 | 74 | 37.56 | 0.0000 |
| Mesoderm development | 223 | 42 | 17.16 | 0.0000 |
| Immunity and defense | 453 | 65 | 34.87 | 0.0000 |
| Ligand-mediated signaling | 105 | 24 | 8.08 | 0.0007 |
| Cytokine and chemokine mediated signaling pathway | 64 | 18 | 4.93 | 0.0008 |
| Cell adhesion | 207 | 34 | 15.93 | 0.0013 |
| Cell proliferation and differentiation | 415 | 56 | 31.94 | 0.0014 |
| Cell structure | 273 | 40 | 21.01 | 0.0161 |
| Receptor protein tyrosine kinase signaling pathway | 81 | 18 | 6.23 | 0.0165 |
| Macrophage-mediated immunity | 35 | 11 | 2.69 | 0.0165 |
| Skeletal development | 55 | 14 | 4.23 | 0.0255 |
| Signaling Pathways | | | | |
| Integrin signalling pathway | 134 | 29 | 10.31 | 0.0000 |
| TGF-beta signaling pathway | 88 | 13 | 6.77 | 0.0209 |
| Insulin/IGF pathway-protein kinase B signaling cascade | 38 | 7 | 2.92 | 0.0295 |
| Molecular Function | | | | |
| Extracellular matrix | 126 | 44 | 9.7 | 0.0000 |
| Extracellular matrix structural protein | 34 | 20 | 2.62 | 0.0000 |
| Signaling molecule | 279 | 57 | 21.47 | 0.0000 |
| Receptor | 357 | 58 | 27.48 | 0.0000 |

REFERENCES

1) Angerer L M, Angerer R C. 2000 Animal-vegetal axis patterning mechanisms in the early sea urchin embryo. Dev Biol. 218:1-12.

2) Aubert J, Dunstan H, Chambers I, Smith A. 2002 Functional gene screening in embryonic stem cells implicates Wnt antagonism in neural differentiation. Nat Biotechnol. 20:1240-5.

3) Brandenberger R, Wei H, Zhang S, Lei S, Murage J, Fisk G J, Li Y, Xu C, Fang R, Guegler K, Rao M S, Mandalam R, Lebkowski J, Stanton L W. 2004 Transcriptome characterization elucidates signaling networks that control human ES cell growth and differentiation. Nat. Biotechnol. 22:707-16.

4) Fehling H J, Lacaud G, Kubo A, Kennedy M, Robertson S, Keller G, Kouskoff V. 2003 Tracking mesoderm induction and its specification to the hemangioblast during embryonic stem cell differentiation. Development 130:4217-27.

5) Ginis I, Luo Y, Miura T, Thies S, Brandenberger R, Gerecht-Nir S, Amit M, Hoke A, Carpenter M K, Itskovitz-Eldor J, Rao M S. 2004 Differences between human and mouse embryonic stem cells. Dev Biol. 269:360-80

6) Gregorieff A, Clevers H. 2005 Wnt signaling in the intestinal epithelium: from endoderm to cancer. Genes Dev. 19:877-90.

7) Hart A H, Hartley L, Sourris K, Stadler E S, Li R, Stanley E G, Tam P P, Elefanty A G, Robb L. 2002 Mixl1 is required for axial mesendoderm morphogenesis and patterning in the murine embryo. Development 129:3597-608.

8) Hay D C, Sutherland L, Clark J, Burdon T. 2004 Oct-4 knockdown induces similar patterns of endoderm and trophoblast differentiation markers in human and mouse embryonic stem cells. Stem Cells. 22:225-35.

9) Keller G. 2005 Embryonic stem cell differentiation: emergence of a new era in biology and medicine. Genes Dev. 19:1129-55.

10) Kimelman D, Griffin K J. 2000 Vertebrate mesendoderm induction and patterning. Curr Opin Genet Dev. 10:350-6

11) Kubo A, Shinozaki K, Shannon J M, Kouskoff V, Kennedy M, Woo S, Fehling H J, Keller G. 2004 Development of definitive endoderm from embryonic stem cells in culture. Development 131:1651-62.

12) Liu P, Wakamiya M, Shea M J, Albrecht U, Behringer R R, Bradley A. 1999 Requirement for Wnt3 in vertebrate axis formation. Nat. Genet. 22:361-5

13) Miller J R, Moon R T. 1996 Signal transduction through beta-catenin and specification of cell fate during embryogenesis. Genes Dev. 10:2527-39.

14) Mitsui K, Tokuzawa Y, Itoh H, Segawa K, Murakami M, Takahashi K, Maruyama M, Maeda M, Yamanaka S. 2003 The homeoprotein Nanog is required for maintenance of pluripotency in mouse epiblast and ES cells. Cell 113:631-42.

15) Nusse R. 2005 Wnt signaling in disease and in development. Cell Res. 15:28-32.

16) Rathjen J, Lake J A, Bettess M D, Washington J M, Chapman G, Rathjen P D. 1999 Formation of a primitive ectoderm like cell population, EPL cells, from ES cells in response to biologically derived factors. J Cell Sci. 112: 601-12.

17) Rodaway A, Patient R. 2001 Mesendoderm. an ancient germ layer? Cell 105:169-72.

18) Sato N, Meijer L, Skaltsounis L, Greengard P, Brivanlou A H. 2004 Maintenance of pluripotency in human and mouse embryonic stem cells through activation of Wnt signaling by a pharmacological GSK-3-specific inhibitor. Nat. Med. 10: 55-63.

19) Shibamoto, S. K, Higano, R. Takada, F. Ito, M. Takeichi, and S. Takada. 1998. Cytoskeletal reorganization by soluable Wnt-3a protein signaling. Gene Cells 3: 659-670

20) Shivdasani R A. 200 Molecular regulation of vertebrate early endoderm development. Dev Biol. 249:191-203

21) Siegfried E, Perrimon N. 1994 *Drosophila* wingless: a paradigm for the function and mechanism of Wnt signaling. Bioessays. 16:395-404.

22) Technau U, Scholz C B 2003 Origin and evolution of endoderm and mesoderm. Int J Dev Biol. 47: 531-9

23) Thomson J A, Itskovitz-Eldor J, Shapiro S S, Waknitz M A, Swiergiel J J, Marshall V S, Jones J M. 1998 Embryonic stem cell lines derived from human blastocysts. Science 282: 1145-7

24) Willert K, Nusse R. 1998 Beta-catenin: a key mediator of Wnt signaling. Curr Opin Genet Dev. 8:95-102.

Ogawa K et al Biochem Biophys Res Commun. 2006, 343(1):159-66. Synergistic action of Wnt and LIF in maintaining pluripotency of mouse ES cells.

Dravid G, et al Stem Cells. 2005, 23(10):1489-501 Defining the role of Wnt/beta-catenin signaling in the survival, proliferation, and self-renewal of human embryonic stem cells.

Singla D K, Schneider D J, LeWinter M M, Sobel B E. Wnt3a but not wnt11 supports self-renewal of embryonic stem cells. Biochem Biophys Res Commun. 2006, 345(2): 789-95

Lindsley R C, Gill J G, Kyba M, Murphy T L, Murphy K M. Canonical Wnt signaling is required for development of embryonic stem cell-derived mesoderm. Development. 2006, 133(19):3787-96.

Assady, S., G. Maor, et al. (2001). "Insulin production by human embryonic stem cells." Diabetes 50(8): 1691-7.

Buttery, L. D., S. Bourne, et al. (2001). "Differentiation of osteoblasts and in vitro bone formation from murine embryonic stem cells." Tissue Eng 7(1): 89-99.

Cao, T., B. C. Heng, et al. (2005). "Osteogenic differentiation within intact human embryoid bodies result in a marked increase in osteocalcin secretion after 12 days of in vitro culture, and formation of morphologically distinct nodule-like structures." Tissue Cell 37(4): 325-34.

Kania, G., P. Blyszczuk, et al. (2003). "Differentiation of mouse embryonic stem cells into pancreatic and hepatic cells." Methods Enzymol 365: 287-303.

Kania, G., P. Blyszczuk, et al. (2004). "Generation of glycogen- and albumin-producing hepatocyte-like cells from embryonic stem cells." Biol Chem 385(10): 943-53.

Kehat, I., M. Amit, et al. (2003). "Development of cardiomyocytes from human ES cells." Methods Enzymol 365: 461-73.

Kramer, J., F. Bohrnsen, et al. (2006). "Stem cell-derived chondrocytes for regenerative medicine." Transplant Proc 38(3): 762-5.

Mummery, C., D. Ward, et al. (2002). "Cardiomyocyte differentiation of mouse and human embryonic stem cells." J Anat 200 (Pt 3): 233-42.

Mummery, C., D. Ward-van Oostwaard, et al. (2003). "Differentiation of human embryonic stem cells to cardiomyocytes: role of coculture with visceral endoderm-like cells." Circulation 107(21): 2733-40.

Segev, H., B. Fishman, et al. (2004). "Differentiation of human embryonic stem cells into insulin-producing clusters." Stem Cells 22(3): 265-74.

Xu, C., S. Police, et al. (2002). "Characterization and enrichment of cardiomyocytes derived from human embryonic stem cells." Circ Res 91(6): 501-8.

Yamashita, J., H. Itoh, et al. (2000). "Flk1-positive cells derived from embryonic stem cells serve as vascular progenitors." Nature 408(6808): 92-6.

Annex A: Wnt Genes

| Symbol | Name | ID* |
| --- | --- | --- |
| Wnt1 | wingless-related MMTV integration site 1 | MGI: 98953 |
| Wnt2 | wingless-related MMTV integration site 2 | MGI: 98954 |
| Wnt2b | wingless related MMTV integration site 2b | MGI: 1261834 |
| Wnt3 | wingless-related MMTV integration site 3 | MGI: 98955 |
| Wnt3a | wingless-related MMTV integration site 3A | MGI: 98956 |
| Wnt4 | wingless-related MMTV integration site 4 | MGI: 98957 |
| Wnt5a | wingless-related MMTV integration site 5A | MGI: 98958 |
| Wnt5b | wingless-related MMTV integration site 5B | MGI: 98959 |
| Wnt6 | wingless-related MMTV integration site 6 | MGI: 98960 |
| Wnt7a | wingless-related MMTV integration site 7A | MGI: 98961 |
| Wnt7b | wingless-related MMTV integration site 7B | MGI: 98962 |
| Wnt8a | wingless-related MMTV integration site 8A | MGI: 107924 |
| Wnt8b | wingless related MMTV integration site 8b | MGI: 109485 |
| Wnt9a | wingless-type MMTV integration site 9A | MGI: 2446084 |
| Wnt9b | wingless-type MMTV integration site 9B | MGI: 1197020 |
| Wnt10a | wingless related MMTV integration site 10a | MGI: 108071 |
| Wnt10b | wingless related MMTV integration site 10b | MGI: 108061 |
| Wnt11 | wingless-related MMTV integration site 11 | MGI: 101948 |
| Wnt16 | wingless-related MMTV integration site 16 | MGI: 2136018 |

*Mouse Genome Informatics ID Number (http://www.informatics.jax.org/)

Annex B: Wnt Pathway Genes

| GeneID_NCBI | Name | Symbol | Chromosome |
| --- | --- | --- | --- |
| 17125 | wingless-related MMTV integration site 6 | Wnt6 | 1 |
| 17129 | retinal S-antigen | Sag | 1 |
| 18797 | similar to cadherin 19, type 2 preproprotein (Interim) | na | 1 |
| 18761 | frizzled homolog 7 (*Drosophila*) | Fzd7 | 1 |
| 18753 | Swi/SNF related matrix associated, actin dependent regulator of chromatin, subfamily a-like 1 | Smarcal1 | 1 |
| 20377 | cadherin 7, type 2 | Cdh7 | 1 |
| 19055 | cadherin 20 | Cdh20 | 1 |
| 19016 | wingless related MMTV integration site 10a | Wnt10a | 1 |
| 14676 | zinc finger, RAN-binding domain containing 3 | Zranb3 | 1 |
| 14672 | phospholipase C, delta 4 | Plcd4 | 1 |
| 17883 | adenylosuccinate synthetase, non muscle | Adss | 1 |
| 17879 | phospholipase C-like 1 | Plcl1 | 1 |
| 21414 | protein phosphatase 2, regulatory subunit B (B56), alpha isoform | Ppp2r5a | 1 |
| 16973 | frizzled homolog 5 (*Drosophila*) | Fzd5 | 1 |
| 12562 | engrailed 1 | En1 | 1 |
| 12558 | ankyrin repeat domain 23 | Ankrd23 | 1 |
| 12554 | protein kinase C, theta | Prkcq | 2 |
| 12550 | protein phosphatase 6, catalytic subunit | Ppp6c | 2 |

-continued

| GeneID_NCBI | Name | Symbol | Chromosome |
|---|---|---|---|
| 21885 | nuclear factor of activated T-cells, cytoplasmic, calcineurin-dependent 2 | Nfatc2 | 2 |
| 11565 | phospholipase C, beta 2 | Plcb2 | 2 |
| 20890 | activin A receptor, type IC | Acvr1c | 2 |
| 13017 | phospholipase C, gamma 1 | Plcg1 | 2 |
| 13001 | phospholipase C, beta 1 | Plcb1 | 2 |
| 11465 | casein kinase II, alpha 1 polypeptide | Csnk2a1 | 2 |
| 11461 | cadherin 22 | Cdh22 | 2 |
| 57265 | RIKEN cDNA 4632409L19 gene | 4632409L19Rik | 2 |
| 56811 | frizzled-related protein | Frzb | 2 |
| 21372 | phospholipase C, beta 4 | Plcb4 | 2 |
| 353237 | brain expressed myelocytomatosis oncogene | Bmyc | 2 |
| 12006 | similar to KIAA1512 protein (Interim) | na | 2 |
| 11994 | cadherin-like 26 | Cdh26 | 2 |
| 13542 | similar to MYH7B protein (Interim) | LOC381400 | 2 |
| 13380 | actin, alpha, cardiac | Actc1 | 2 |
| 11789 | cadherin 4 | Cdh4 | 2 |
| 22420 | GA repeat binding protein, beta 1 | Gabpb1 | 2 |
| 22416 | gremlin 1 | Grem1 | 2 |
| 22412 | LOC433451 (Interim) | na | 2 |
| 22408 | protein phosphatase 3, catalytic subunit, alpha isoform | Ppp3ca | 3 |
| 20997 | dickkopf homolog 2 (*Xenopus laevis*) | Dkk2 | 3 |
| 12942 | phospholipase C-like 3 | Plcl3 | 3 |
| 12914 | bone morphogenetic protein receptor, type 1B | Bmpr1b | 3 |
| 22059 | chromodomain helicase DNA binding protein 1-like | Chd1l | 3 |
| 245827 | B-cell CLL/lymphoma 9 | Bcl9 | 3 |
| 245578 | secreted frizzled-related sequence protein 2 | Sfrp2 | 3 |
| 245355 | protein kinase C, iota | Prkci | 3 |
| 73159 | SWI/SNF related, matrix associated, actin dependent regulator of chromatin, subfamily a, member 3 | Smarca3 | 3 |
| 239985 | seven in absentia 2 | Siah2 | 3 |
| 67857 | protocadherin 10 | Pcdh10 | 3 |
| 238939 | lymphoid enhancer binding factor 1 | Lef1 | 3 |
| 319757 | dachsous 2 (*Drosophila*) | Dchs2 | 3 |
| 104318 | transducin (beta)-like 1X-linked receptor 1 | Tbl1xr1 | 3 |
| 93702 | protocadherin 18 | Pcdh18 | 3 |
| 269437 | cadherin EGF LAG seven-pass G-type receptor 2 | Celsr2 | 3 |
| 93892 | MAD homolog 9 (*Drosophila*) | Smad9 | 3 |
| 93888 | wingless related MMTV integration site 2b | Wnt2b | 3 |
| 93884 | guanine nucleotide binding protein, beta 4 | Gnb4 | 3 |
| 93880 | guanine nucleotide binding protein (G protein), gamma 5 subunit | Gng5 | 3 |
| 93876 | GA repeat binding protein, beta 2 | Gabpb2 | 3 |
| 93872 | transducin-like enhancer of split 1, homolog of *Drosophila* E(spl) | Tle1 | 4 |
| 93760 | dishevelled, dsh homolog 1 (*Drosophila*) | Dvl1 | 4 |
| 93724 | AT rich interactive domain 1A (Swi1 like) | Arid1a | 4 |
| 93716 | ankyrin repeat domain 6 | Ankrd6 | 4 |
| 93712 | wingless-related MMTV integration site 4 | Wnt4 | 4 |
| 93708 | lung carcinoma myc related oncogene 1 | Lmyc1 | 4 |
| 93704 | protein kinase C, zeta | Prkcz | 4 |
| 18099 | cerberus 1 homolog (*Xenopus laevis*) | Cer1 | 4 |
| 18019 | mitogen activated protein kinase kinase kinase 7 | Map3k7 | 4 |
| 14695 | similar to ATP-dependent chromatin remodeling protein SNF2H (Interim) | na | 4 |
| 14675 | histone deacetylase 1 | Hdac1 | 4 |
| 18018 | cadherin 17 | Cdh17 | 4 |
| 17882 | catenin alpha-like 1 | Catnal1 | 4 |
| 17870 | transforming growth factor, beta receptor I | Tgfbr1 | 4 |
| 14370 | guanine nucleotide binding protein, beta 1 | Gnb1 | 4 |
| 14366 | RIKEN cDNA A930027K05 gene | A930027K05Rik | 4 |
| 14362 | similar to SWI/SNF related, matrix associated, actin dependent regulator of chromatin, subfamily e, member 1 | BAF57 (Interim) | 4 |
| 17393 | protein phosphatase 3, regulatory subunit B, alpha isoform (calcineurin B, type II) | Ppp3r2 | 4 |
| 19015 | similar to Protein phosphatase 2, regulatory subunit B (B56), alpha isoform (Interim) | na | 4 |
| 20215 | similar to Protein phosphatase 2, regulatory subunit B (B56), alpha isoform (Interim) | na | 4 |
| 18796 | guanine nucleotide binding protein (G protein), gamma 10 | Gng10 | 4 |
| 18752 | actin, beta, cytoplasmic | Actb | 5 |
| 17128 | frizzled homolog 1 (*Drosophila*) | Fzd1 | 5 |
| 216869 | E1A binding protein p400 | Ep400 | 5 |
| 12167 | frizzled homolog 10 (*Drosophila*) | Fzd10 | 5 |
| 219228 | SWI/SNF related, matrix associated, actin dependent regulator of chromatin, subfamily d, member 3 | Smarcd3 | 5 |
| 12005 | guanine nucleotide binding protein, beta 2 | Gnb2 | 5 |
| 236969 | protocadherin 7 | Pcdh7 | 5 |

-continued

| GeneID_NCBI | Name | Symbol | Chromosome |
|---|---|---|---|
| 57376 | C-terminal binding protein 1 | Ctbp1 | 5 |
| 239096 | frizzled homolog 9 (Drosophila) | Fzd9 | 5 |
| 238880 | engrailed 2 | En2 | 5 |
| 353236 | peroxisome proliferator activated receptor gamma | Pparg | 6 |
| 23805 | smoothened homolog (Drosophila) | Smo | 6 |
| 22423 | guanine nucleotide binding protein, beta 3 | Gnb3 | 6 |
| 22419 | wingless-related MMTV integration site 5B | Wnt5b | 6 |
| 22415 | wingless-related MMTV integration site 16 | Wnt16 | 6 |
| 22411 | phospholipase C, zeta 1 | Plcz1 | 6 |
| 227485 | actin, gamma 2, smooth muscle, enteric | Actg2 | 6 |
| 269275 | catenin alpha 2 | Catna2 | 6 |
| 68058 | wingless-related MMTV integration site 7A | Wnt7a | 6 |
| 67155 | wingless-related MMTV integration site 2 | Wnt2 | 6 |
| 107934 | transcription factor 3 | Tcf3 | 6 |
| 93701 | low density lipoprotein receptor-related protein 6 | Lrp6 | 6 |
| 77578 | inositol 1,4,5-triphosphate receptor 2 | Itpr2 | 6 |
| 320873 | inositol 1,4,5-triphosphate receptor 1 | Itpr1 | 6 |
| 93891 | cyclin D2 | Ccnd2 | 6 |
| 93887 | homeo box A6 | Hoxa6 | 6 |
| 93883 | guanine nucleotide binding protein (G protein), gamma 12 | Gng12 | 6 |
| 93879 | C-terminal binding protein 2 | Ctbp2 | 7 |
| 93875 | RIKEN cDNA 3110041P15 gene | 3110041P15Rik | 7 |
| 93735 | frizzled homolog 4 (Drosophila) | Fzd4 | 7 |
| 93723 | wingless-related MMTV integration site 11 | Wnt11 | 7 |
| 93715 | protein kinase C, beta 1 | Prkcb1 | 7 |
| 93711 | arrestin, beta 1 | Arrb1 | 7 |
| 93707 | paternally expressed 12 | Peg12 | 7 |
| 75560 | similar to Snf2-related CBP activator protein (Interim) | na | 7 |
| 72469 | dachsous 1 (Drosophila) | Dchs1 | 7 |
| 211712 | cyclin D1 | Ccnd1 | 7 |
| 14369 | similar to Snf2-related CBP activator protein (Interim) | na | 7 |
| 14365 | guanine nucleotide binding protein (G protein), gamma 8 subunit | Gng8 | 7 |
| 114875 | MAD homolog 1 (Drosophila) | Smad1 | 8 |
| 19057 | secreted frizzled-related sequence protein 1 | Sfrp1 | 8 |
| 19053 | cadherin 5 | Cdh5 | 8 |
| 14107 | cadherin 13 | Cdh13 | 8 |
| 20379 | cadherin 1 | Cdh1 | 8 |
| 20319 | protein phosphatase 2a, catalytic subunit, beta isoform | Ppp2cb | 8 |
| 18803 | fat tumor suppressor homolog (Drosophila) | Fath | 8 |
| 18799 | actin, alpha 1, skeletal muscle | Acta1 | 8 |
| 18795 | cadherin 8 | Cdh8 | 8 |
| 18759 | cadherin 3 | Cdh3 | 8 |
| 18755 | cadherin 11 | Cdh11 | 8 |
| 18751 | nuclear factor of activated T-cells, cytoplasmic, calcineurin-dependent 3 | Nfatc3 | 8 |
| 12166 | cadherin 15 | Cdh15 | 8 |
| 192164 | gene model 1841, (NCBI) | na | 8 |
| 13544 | dickkopf homolog 4 (Xenopus laevis) | Dkk4 | 8 |
| 140781 | seven in absentia 1A | Siah1a | 8 |
| 140577 | gene model 1467, (NCBI) | na | 8 |
| 12995 | SWI/SNF related, matrix associated, actin dependent regulator of chromatin, subfamily a, member 5 | Smarca5 | 8 |
| 11468 | casein kinase II, alpha 2, polypeptide | Csnk2a2 | 8 |
| 11459 | phospholipase C, gamma 2 | Plcg2 | 8 |
| 12936 | similar to Guanine nucleotide-binding protein G(I)/G(S)/G(O) gamma-12 subunit (Interim) | na | 8 |
| 12564 | DAN domain family, member 5 | Dand5 | 8 |
| 12560 | matrix metalloproteinase 7 | Mmp7 | 9 |
| 12552 | cadherin EGF LAG seven-pass G-type receptor 3 | Celsr3 | 9 |
| 12386 | phospholipase C, delta 1 | Plcd1 | 9 |
| 104010 | casein kinase 1, gamma 1 | Csnk1g1 | 9 |
| 109689 | guanine nucleotide binding protein, beta 5 | Gnb5 | 9 |
| 103583 | gene model 1132, (NCBI) | Gm1132 | 9 |
| 279653 | SWI/SNF related, matrix associated, actin dependent regulator of chromatin, subfamily a, member 4 | Smarca4 | 9 |
| 103236 | transducin-like enhancer of split 3, homolog of Drosophila E(spl) | Tle3 | 9 |
| 93703 | catenin beta | Catnb | 9 |
| 93699 | DIX domain containing 1 | Dixdc1 | 9 |
| 93687 | RIKEN cDNA B230218L05 gene | B230218L05Rik | 9 |
| 83796 | guanine nucleotide binding protein, alpha 15 | Gna15 | 10 |
| 93897 | guanine nucleotide binding protein, alpha 11 | Gna11 | 10 |
| 93893 | protocadherin 15 | Pcdh15 | 10 |
| 93889 | adenomatosis polyposis coli 2 | Apc2 | 10 |
| 93885 | casein kinase 1, gamma 2 | Csnk1g2 | 10 |
| 93881 | cadherin 23 (otocadherin) | Cdh23 | 10 |

| GeneID_NCBI | Name | Symbol | Chromosome |
|---|---|---|---|
| 93877 | transducin-like enhancer of split 2, homolog of *Drosophila* E(spl) | Tle2 | 10 |
| 93873 | catenin alpha 3 | Catna3 | 10 |
| 93761 | histone deacetylase 2 | Hdac2 | 10 |
| 93717 | SWI/SNF related, matrix associated, actin dependent regulator of chromatin, subfamily b, member 1 | Smarcb1 | 10 |
| 93713 | amino-terminal enhancer of split | Aes | 10 |
| 93709 | transducin-like enhancer of split 6, homolog of *Drosophila* E(spl) | Tle6 | 10 |
| 93705 | guanine nucleotide binding protein (G protein), gamma 7 subunit | Gng7 | 10 |
| 74055 | similar to protocadherin (Interim) | na | 10 |
| 68142 | myosin, heavy polypeptide 3, skeletal muscle, embryonic | Myh3 | 11 |
| 70425 | myosin, heavy polypeptide 1, skeletal muscle, adult | Myh1 | 11 |
| 70315 | transcription factor 7, T-cell specific | Tcf7 | 11 |
| 66993 | actin, gamma, cytoplasmic 1 | Actg1 | 11 |
| 54380 | frizzled homolog 2 (*Drosophila*) | Fzd2 | 11 |
| 241201 | axin2 | Axin2 | 11 |
| 59036 | wingless-related MMTV integration site 3A | Wnt3a | 11 |
| 23836 | wingless-type MMTV integration site 9B | Wnt9b | 11 |
| 353235 | transformation related protein 53 | Trp53 | 11 |
| 22421 | gene model 523, (NCBI) | Gm523 | 11 |
| 22417 | casein kinase 1, delta | Csnk1d | 11 |
| 22413 | nemo like kinase | Nlk | 11 |
| 22409 | myosin, heavy polypeptide 2, skeletal muscle, adult | Myh2 | 11 |
| 226409 | arrestin, beta 2 | Arrb2 | 11 |
| 22295 | SWI/SNF related, matrix associated, actin dependent regulator of chromatin, subfamily e, member 1 | Smarce1 | 11 |
| 353234 | wingless-related MMTV integration site 3 | Wnt3 | 11 |
| 27412 | phospholipase C, delta 3 | Plcd3 | 11 |
| 20585 | F-box and WD-40 domain protein 11 | Fbxw11 | 11 |
| 21886 | SWI/SNF related, matrix associated, actin dependent regulator of chromatin, subfamily d, member 2 | Smarcd2 | 11 |
| 26932 | myosin, heavy polypeptide 4, skeletal muscle | Myh4 | 11 |
| 20439 | wingless-type MMTV integration site 9A | Wnt9a | 11 |
| 216033 | protein phosphatase 2a, catalytic subunit, alpha isoform | Ppp2ca | 11 |
| 21415 | protein kinase C, alpha | Prkca | 11 |
| 16974 | dishevelled 2, dsh homolog (*Drosophila*) | Dvl2 | 11 |
| 16918 | myosin, heavy polypeptide 8, skeletal muscle, perinatal | Myh8 | 11 |
| 18530 | similar to Protein phosphatase 2, regulatory subunit B (B56), alpha isoform (Interim) | na | 11 |
| 18526 | protein phosphatase 3, regulatory subunit B, alpha isoform (calcineurin B, type I) | Ppp3r1 | 11 |
| 16842 | adenylosuccinate synthetase like 1 | Adssl1 | 12 |
| 215654 | protein kinase C, eta | Prkch | 12 |
| 15182 | dapper homolog 1, antagonist of beta-catenin (*xenopus*) | Dact1 | 12 |
| 16439 | protein phosphatase 2, regulatory subunit B (B56), epsilon isoform | Ppp2r5e | 12 |
| 18109 | neuroblastoma myc-related oncogene 1 | Nmyc1 | 12 |
| 18021 | protein phosphatase 2, regulatory subunit B (B56), gamma isoform | Ppp2r5c | 12 |
| 214897 | similar to Tle6 protein (Interim) | na | 12 |
| 14697 | similar to hypothetical protein FLJ23834 (Interim) | na | 12 |
| 14693 | RIKEN cDNA 1110049B09 gene | 1110049B09Rik | 12 |
| 17888 | MAD homolog 5 (*Drosophila*) | Smad5 | 13 |
| 17884 | RIKEN cDNA 4732495G21 gene | 4732495G21Rik | 13 |
| 212398 | secreted frizzled-related sequence protein 4 | Sfrp4 | 13 |
| 225849 | endothelin 1 | Edn1 | 13 |
| 219257 | cDNA sequence BC040758 | BC040758 | 13 |
| 216795 | guanine nucleotide binding protein (G protein), gamma 4 subunit | Gng4 | 13 |
| 14368 | similar to PC-LKC gene product (Interim) | na | 13 |
| 14296 | protein kinase C, delta | Prkcd | 14 |
| 19056 | gene model 281, (NCBI) | na | 14 |
| 19052 | gene model 78, (NCBI) | Gm78 | 14 |
| 19013 | cadherin-like 24 | Cdh24 | 14 |
| 20378 | protocadherin 9 | Pcdh9 | 14 |
| 18802 | frizzled homolog 3 (*Drosophila*) | Fzd3 | 14 |
| 18798 | protein phosphatase 3, catalytic subunit, gamma isoform | Ppp3cc | 14 |
| 18762 | bone morphogenetic protein receptor, type 1A | Bmpr1a | 14 |
| 18754 | myosin, heavy polypeptide 7, cardiac muscle, beta | Myh7 | 14 |
| 18750 | protocadherin 8 | Pcdh8 | 14 |
| 13614 | myosin, heavy polypeptide 6, cardiac muscle, alpha | Myh6 | 14 |
| 13543 | protocadherin 20 | Pcdh20 | 14 |
| 192163 | protein phosphatase 3, catalytic subunit, beta isoform | Ppp3cb | 14 |
| 11566 | nuclear factor of activated T-cells, cytoplasmic, calcineurin-dependent 4 | Nfatc4 | 14 |

-continued

| GeneID_NCBI | Name | Symbol | Chromosome |
|---|---|---|---|
| 11479 | wingless-related MMTV integration site 5A | Wnt5a | 14 |
| 11475 | protocadherin 21 | Pcdh21 | 14 |
| 170735 | gene model 912, (NCBI) | na | 14 |
| 12943 | guanine nucleotide binding protein (G protein), gamma 2 subunit | Gng2 | 14 |
| 12939 | RIKEN cDNA C330003B14 gene | C330003B14Rik | 14 |
| 12622 | LOC432902 (Interim) | na | 14 |
| 12614 | wingless-related MMTV integration site 1 | Wnt1 | 15 |
| 12563 | cadherin 10 | Cdh10 | 15 |
| 12555 | cadherin 12 | Cdh12 | 15 |
| 107771 | frizzled homolog 6 (*Drosophila*) | Fzd6 | 15 |
| 12385 | peroxisome proliferator activated receptor alpha | Ppara | 15 |
| 12234 | activin A receptor, type 1B | Acvr1b | 15 |
| 192161 | cadherin EGF LAG seven-pass G-type receptor 1 | Celsr1 | 15 |
| 227120 | cadherin 6 | Cdh6 | 15 |
| 21926 | similar to Cadherin-18 precursor (Cadherin-14) (Interim) | na | 15 |
| 229459 | SWI/SNF related, matrix associated, actin dependent regulator of chromatin, subfamily d, member 1 | Smarcd1 | 15 |
| 20587 | E1A binding protein p300 | Ep300 | 15 |
| 234217 | wingless-related MMTV integration site 7B | Wnt7b | 15 |
| 21888 | wingless related MMTV integration site 10b | Wnt10b | 15 |
| 234130 | casein kinase 1, epsilon | Csnk1e | 15 |
| 20437 | myelocytomatosis oncogene | Myc | 15 |
| 26409 | cadherin 9 | Cdh9 | 15 |
| 434895 | homeo box C6 | Hoxc6 | 15 |
| 434683 | homeo box C5 | Hoxc5 | 15 |
| 434245 | RIKEN cDNA B230220E17 gene | B230220E17Rik | 15 |
| 433797 | CREB binding protein | Crebbp | 16 |
| 433759 | dishevelled 3, dsh homolog (*Drosophila*) | Dvl3 | 16 |
| 433548 | glycogen synthase kinase 3 beta | Gsk3b | 16 |
| 433493 | similar to CREB-binding protein (Interim) | na | 16 |
| 432937 | open reading frame 63 | ORF63 | 16 |
| 385356 | similar to G protein gamma-5 subunit (Interim) | na | 16 |
| 384866 | casein kinase II, beta subunit | Csnk2b | 17 |
| 382129 | brachyury | T | 17 |
| 381409 | AT rich interactive domain 1B (Swi1 like) | Arid1b | 17 |
| 381400 | peroxisome proliferator activator receptor delta | Ppard | 17 |
| 93700 | axin 1 | Axin1 | 17 |
| 83797 | protein kinase C, epsilon | Prkce | 17 |
| 328572 | tumor necrosis factor | Tnf | 17 |
| 81004 | phospholipase C-like 2 | Plcl2 | 17 |
| 93890 | protein phosphatase 2, regulatory subunit B (B56), delta isoform | Ppp2r5d | 17 |
| 93886 | inositol 1,4,5-triphosphate receptor 3 | Itpr3 | 17 |
| 93882 | cyclin D3 | Ccnd3 | 17 |
| 93878 | dapper homolog 2, antagonist of beta-catenin (*xenopus*) | Dact2 | 17 |
| 93874 | guanine nucleotide binding protein 13, gamma | Gng13 | 17 |
| 93762 | cadherin 2 | Cdh2 | 18 |
| 93722 | wingless-related MMTV integration site 8A | Wnt8a | 18 |
| 93714 | protocadherin alpha subfamily C, 2 | Pcdhac2 | 18 |
| 93710 | adenomatosis polyposis *coli* | Apc | 18 |
| 93706 | protocadherin alpha 11 | Pcdha11 | 18 |
| 75599 | protocadherin gamma subfamily B, 5 | Pcdhgb5 | 18 |
| 73181 | protocadherin beta 21 | Pcdhb21 | 18 |
| 73173 | protocadherin beta 17 | Pcdhb17 | 18 |
| 54612 | protocadherin beta 13 | Pcdhb13 | 18 |
| 54216 | protocadherin beta 9 | Pcdhb9 | 18 |
| 53883 | protocadherin beta 5 | Pcdhb5 | 18 |
| 53601 | protocadherin beta 1 | Pcdhb1 | 18 |
| 56637 | protocadherin gamma subfamily A, 12 | Pcdhga12 | 18 |
| 55994 | protocadherin gamma subfamily A, 8 | Pcdhga8 | 18 |
| 233651 | protocadherin gamma subfamily A, 4 | Pcdhga4 | 18 |
| 22422 | protocadherin gamma subfamily C, 5 | Pcdhgc5 | 18 |
| 22418 | protocadherin gamma subfamily B, 7 | Pcdhgb7 | 18 |
| 22414 | nuclear factor of activated T-cells, cytoplasmic, calcineurin-dependent 1 | Nfatc1 | 18 |
| 22410 | frizzled homolog 8 (*Drosophila*) | Fzd8 | 18 |
| 27373 | MAD homolog 4 (*Drosophila*) | Smad4 | 18 |
| 20586 | protocadherin alpha subfamily C, 1 | Pcdhac1 | 18 |
| 21887 | protocadherin gamma subfamily B, 4 | Pcdhgb4 | 18 |
| 224860 | protocadherin beta 20 | Pcdhb20 | 18 |
| 21770 | protocadherin beta 16 | Pcdhb16 | 18 |
| 21416 | protocadherin beta 12 | Pcdhb12 | 18 |
| 16440 | protocadherin beta 8 | Pcdhb8 | 18 |
| 14797 | protocadherin beta 4 | Pcdhb4 | 18 |
| 14682 | protocadherin gamma subfamily A, 11 | Pcdhga11 | 18 |
| 17885 | protocadherin gamma subfamily A, 7 | Pcdhga7 | 18 |
| 17869 | protocadherin gamma subfamily A, 3 | Pcdhga3 | 18 |

| GeneID_NCBI | Name | Symbol | Chromosome |
|---|---|---|---|
| 114606 | protocadherin gamma subfamily C, 4 | Pcdhgc4 | 18 |
| 13016 | protocadherin alpha 12 | Pcdha12 | 18 |
| 13000 | protocadherin alpha 4 | Pcdha4 | 18 |
| 11464 | protocadherin gamma subfamily B, 6 | Pcdhgb6 | 18 |
| 12941 | protocadherin gamma subfamily B, 1 | Pcdhgb1 | 18 |
| 12937 | casein kinase 1, alpha 1 | Csnk1a1 | 18 |
| 12565 | protocadherin beta 22 | Pcdhb22 | 18 |
| 12561 | protocadherin beta 18 | Pcdhb18 | 18 |
| 12557 | protocadherin beta 14 | Pcdhb14 | 18 |
| 12387 | protocadherin beta 10 | Pcdhb10 | 18 |
| 225805 | protocadherin beta 6 | Pcdhb6 | 18 |
| 116731 | protocadherin beta 2 | Pcdhb2 | 18 |
| 170677 | protocadherin gamma subfamily A, 9 | Pcdhga9 | 18 |
| 234779 | protocadherin gamma subfamily A, 5 | Pcdhga5 | 18 |
| 226849 | protocadherin gamma subfamily A, 1 | Pcdhga1 | 18 |
| 54366 | protocadherin gamma subfamily B, 8 | Pcdhgb8 | 18 |
| 26931 | casein kinase 1, gamma 3 | Csnk1g3 | 18 |
| 21812 | protocadherin alpha 8 | Pcdha8 | 18 |
| 20438 | protocadherin alpha 2 | Pcdha2 | 18 |
| 15201 | protocadherin alpha 3 | Pcdha3 | 18 |
| 16438 | protocadherin alpha 10 | Pcdha10 | 18 |
| 14696 | protocadherin alpha 7 | Pcdha7 | 18 |
| 14688 | catenin alpha 1 | Catna1 | 18 |
| 14371 | protocadherin alpha 9 | Pcdha9 | 18 |
| 14367 | protocadherin gamma subfamily B, 2 | Pcdhgb2 | 18 |
| 12444 | protocadherin beta 19 | Pcdhb19 | 18 |
| 434495 | protocadherin beta 15 | Pcdhb15 | 18 |
| 12443 | protocadherin beta 11 | Pcdhb11 | 18 |
| 269615 | protocadherin beta 7 | Pcdhb7 | 18 |
| 12445 | protocadherin beta 3 | Pcdhb3 | 18 |
| 432545 | protocadherin gamma subfamily A, 10 | Pcdhga10 | 18 |
| 13799 | protocadherin gamma subfamily A, 6 | Pcdhga6 | 18 |
| 433545 | protocadherin gamma subfamily A, 2 | Pcdhga2 | 18 |
| 13798 | protocadherin gamma subfamily C, 3 | Pcdhgc3 | 18 |
| 268663 | RIKEN cDNA 2010005A06 gene | 2010005A06Rik | 18 |
| 383994 | protocadherin 12 | Pcdh12 | 18 |
| 432994 | protocadherin alpha 5 | Pcdha5 | 18 |
| 19059 | protocadherin alpha 6 | Pcdha6 | 18 |
| 15183 | similar to RPD3 protein (Interim) | na | 18 |
| 15425 | protocadherin alpha 1 | Pcdha1 | 18 |
| 382645 | histone deacetylase 3 | Hdac3 | 18 |
| 434573 | RIKEN cDNA C330049O21 gene | C330049O21Rik | 18 |
| 434244 | phospholipase C, beta 3 | Plcb3 | 19 |
| 19058 | low density lipoprotein receptor-related protein 5 | Lrp5 | 19 |
| 224419 | dickkopf homolog 1 (*Xenopus laevis*) | Dkk1 | 19 |
| 381598 | guanine nucleotide binding protein, alpha 14 | Gna14 | 19 |
| 15403 | wingless related MMTV integration site 8b | Wnt8b | 19 |
| 380918 | SWI/SNF related, matrix associated, actin dependent regulator of chromatin, subfamily a, member 2 | Smarca2 | 19 |
| 15424 | phospholipase C, epsilon 1 | Plce1 | 19 |
| 240025 | frequently rearranged in advanced T-cell lymphomas 2 | Frat2 | 19 |
| 436177 | protein phosphatase 2, regulatory subunit B (B56), beta isoform | Ppp2r5b | 19 |
| 382175 | frequently rearranged in advanced T-cell lymphomas | Frat1 | 19 |
| 14704 | actin, alpha 2, smooth muscle, aorta | Acta2 | 19 |
| 14706 | beta-transducin repeat containing protein | Btrc | 19 |
| 14702 | transducin-like enhancer of split 4, homolog of *Drosophila* E(spl) | Tle4 | 19 |
| 14701 | secreted frizzled-related sequence protein 5 | Sfrp5 | 19 |
| 14708 | transcription factor 7-like 2, T-cell specific, HMG-box | Tcf7l2 | 19 |
| 64337 | guanine nucleotide binding protein, alpha q polypeptide | Gnaq | 19 |
| 434496 | helicase, lymphoid specific | Hells | 19 |
| 14709 | guanine nucleotide binding protein (G protein), gamma 3 subunit | Gng3 | 19 |
| 433793 | ankyrin repeat domain 2 (stretch responsive muscle) | Ankrd2 | 19 |
| 436049 | ankyrin repeat domain 1 (cardiac muscle) | Ankrd1 | 19 |
| 381574 | similar to Inositol 1,4,5-trisphosphate receptor type 3 (Type 3 inositol 1,4,5-trisphosphate receptor) (Type 3 InsP3 receptor) (IP3 receptor isoform 3) (InsP3R3) (IP3R-3) (Interim) | na | 17: NT_039671 |
| 435469 | similar to Frizzled-related protein (Interim) | na | 2: NT_080128 |
| 14700 | similar to activin receptor-like kinase 7 (Interim) | na | 2: NT_092545 |
| 56642 | RIKEN cDNA 2610005L07 gene | 2610005L07Rik | 4: NT_101052 |
| 107765 | protein kinase C, gamma, | Prkcc | 7: NT_104311 |
| 436486 | similar to OB-cadherin precursor-mouse (Interim) | na | Un: NT_046901 |
| 14707 | similar to Protein phosphatase 2, regulatory subunit B (B56), alpha isoform (Interim) | na | Un: NT_046916 |
| 78321 | similar to Cadherin-11 precursor (Osteoblast-cadherin) (OB-cadherin) (OSF-4) (Interim) | na | Un: NT_073870 |

-continued

| GeneID_NCBI | Name | Symbol | Chromosome |
|---|---|---|---|
| 432648 | similar to Cadherin-11 precursor (Osteoblast-cadherin) (OB-cadherin) (OSF-4) (Interim) | na | Un: NT_073870 |
| 14391 | similar to Cadherin-11 precursor (Osteoblast-cadherin) (OB-cadherin) (OSF-4) (Interim) | na | Un: NT_102748 |
| 213054 | similar to BAF57 (Interim) | na | Un: NT_105941 |
| 320865 | transducin (beta)-like 1 X-linked | Tbl1x | |
| 432762 | protocadherin 11 X-linked | Pcdh11x | |
| 330938 | similar to Casein kinase II, alpha 1 polypeptide (Interim) | na | |
| 68764 | myc-like oncogene, s-myc protein | Mycs | |
| 330998 | similar to SWI/SNF related, matrix associated, actin dependent regulator of chromatin, subfamily a, member 3 (Interim) | na | |
| 320493 | protocadherin 19 | Pcdh19 | |
| 23863 | SWI/SNF related, matrix associated, actin dependent regulator of chromatin, subfamily a, member 1 | Smarca1 | |
| 23892 | histone deacetylase 8 | Hdac8 | |
| 432472 | arrestin 3, retinal | Arr3 | |
| 105594 | similar to actin, gamma, cytoplasmic (Interim) | na | |
| 433451 | seven in absentia 1B | Siah1b | |
| 432902 | similar to SWI/SNF related, matrix associated, actin dependent regulator of chromatin, subfamily a, member 3 (Interim) | na | X: NT_097788 |

The invention claimed is:

1. A method for producing a mesodermal progenitor cell from an embryonic stem cell, the method comprising activating a Wnt signaling pathway in the embryonic stem cell by culturing the embryonic stem cell in Wnt-3A conditioned medium (CM) or in a medium comprising a chemical inhibitor of glycogen synthase kinase-3β, wherein the Wnt signaling pathway is activated for at least 8 days, thereby producing a mesodermal progenitor cell, wherein the method does not produce an ectodermal cell.

2. The method of claim 1, in which the embryonic stem cell is in a substantially 2 dimensional configuration for at least a portion of the time when the Wnt signaling pathway is activated.

3. The method of claim 2, in which the embryonic stem cell is in a substantially 2 dimensional configuration for substantially all of the time when the Wnt signaling pathway is activated.

4. The method of claim 2, in which the 2 dimensional configuration is a monolayer.

5. The method of claim 1, further comprising terminally differentiating the mesodeimal cell to a cell selected from the group consisting of an adipocyte, a cardiomyocyte, a chondrocyte, a fibroblast, a hematopoietic cell, a myocyte, an osteoblast, and an endothelial cell.

6. The method of claim 1, in which the mesodermal cell expresses a mesodermal marker selected from the group consisting of: T-brachyury, Runx 1 and Pitx2.

7. The method of claim 1, in which the chemical inhibitor comprises iGSK-3β or BIO, or a variant thereof capable of reducing GSK activity.

8. A method of inducing expression of a mesoderm specific marker in a cell comprising culturing an embryonic stem cell in Wnt-3A conditioned medium (CM) or in a medium comprising a chemical inhibitor of glycogen synthase kinase-3β, wherein the culturing is for at least 8 days, thereby inducing expression of a mesoderm specific marker in the cell.

9. The method of claim 8, in which the mesoderm specific marker is selected from the group consisting of: T-brachyury, Runx1 and Pitx2.

10. The method of claim 1, wherein the Wnt signaling pathway is activated for at least 10 days.

11. The method of claim 1, wherein the embryonic stem cell is a human embryonic stem cell.

12. The method of claim 1, wherein the Wnt signaling pathway is activated for at least 2 weeks.

13. The method of claim 1, wherein the Wnt signaling pathway is activated for at least 3 weeks.

14. The method of claim 1, wherein the Wnt signaling pathway is activated for at least 4 weeks.

* * * * *

UNITED STATES PATENT AND TRADEMARK OFFICE
CERTIFICATE OF CORRECTION

PATENT NO.         : 8,460,928 B2
APPLICATION NO.    : 12/091210
DATED              : June 11, 2013
INVENTOR(S)        : Bakre et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1075 days.

Signed and Sealed this
Fourth Day of March, 2014

Michelle K. Lee
*Deputy Director of the United States Patent and Trademark Office*

SEQUENCE LISTING

<160> NUMBER OF SEQ ID NOS: 12

<210> SEQ ID NO 1
<211> LENGTH: 15
<212> TYPE: DNA
<213> ORGANISM: Artificial
<220> FEATURE:
<223> OTHER INFORMATION: TCF/LEF binding site and spacer

<400> SEQUENCE: 1
agatcaaagg gggta                                                      15

<210> SEQ ID NO 2
<211> LENGTH: 20
<212> TYPE: DNA
<213> ORGANISM: Artificial
<220> FEATURE:
<223> OTHER INFORMATION: Oligonucleotide primer

<400> SEQUENCE: 2
accatggagc cccacctgct                                                 20

<210> SEQ ID NO 3
<211> LENGTH: 20
<212> TYPE: DNA
<213> ORGANISM: Artificial
<220> FEATURE:
<223> OTHER INFORMATION: Oligonucleotide primer

<400> SEQUENCE: 3
tgcaggtgtg cacatcgtag                                                 20

<210> SEQ ID NO 4
<211> LENGTH: 20
<212> TYPE: DNA
<213> ORGANISM: Artificial
<220> FEATURE:
<223> OTHER INFORMATION: Oligonucleotide primer

<400> SEQUENCE: 4

```
accatgaaga agcccattgg                                              20

<210> SEQ ID NO 5
<211> LENGTH: 20
<212> TYPE: DNA
<213> ORGANISM: Artificial
<220> FEATURE:
<223> OTHER INFORMATION: Oligonucleotide primer

<400> SEQUENCE: 5
tgcacacgaa ctgatccaca                                              20

<210> SEQ ID NO 6
<211> LENGTH: 5
<212> TYPE: PRT
<213> ORGANISM: Artificial
<220> FEATURE:
<223> OTHER INFORMATION: Peptide substrate motif
<220> FEATURE:
<221> NAME/KEY: misc_feature
<222> LOCATION: (2)..(4)
<223> OTHER INFORMATION: Xaa can be any naturally occurring amino acid

<400> SEQUENCE: 6

Ser Xaa Xaa Xaa Ser
1               5

<210> SEQ ID NO 7
<211> LENGTH: 20
<212> TYPE: DNA
<213> ORGANISM: Artificial
<220> FEATURE:
<223> OTHER INFORMATION: Oligonucleotide primer

<400> SEQUENCE: 7
acatcgccta caaccagacc                                              20

<210> SEQ ID NO 8
<211> LENGTH: 20
<212> TYPE: DNA
<213> ORGANISM: Artificial
<220> FEATURE:
<223> OTHER INFORMATION: Oligonucleotide primer

<400> SEQUENCE: 8
gagataggac ggcaccttga                                              20

<210> SEQ ID NO 9
<211> LENGTH: 20
<212> TYPE: DNA
<213> ORGANISM: Artificial
<220> FEATURE:
<223> OTHER INFORMATION: Oligonucleotide primer

<400> SEQUENCE: 9
ggcatcttca ccctgctcta                                              20

<210> SEQ ID NO 10
<211> LENGTH: 20
<212> TYPE: DNA
<213> ORGANISM: Artificial
<220> FEATURE:
<223> OTHER INFORMATION: Oligonucleotide primer

<400> SEQUENCE: 10
gcctccaggc cttcctatac                                              20
```

```
<210> SEQ ID NO 11
<211> LENGTH: 20
<212> TYPE: DNA
<213> ORGANISM: Artificial
<220> FEATURE:
<223> OTHER INFORMATION: Oligonucleotide primer

<400> SEQUENCE: 11
tctgtccctc acttggttcc                                                  20

<210> SEQ ID NO 12
<211> LENGTH: 20
<212> TYPE: DNA
<213> ORGANISM: Artificial
<220> FEATURE:
<223> OTHER INFORMATION: Oligonucleotide primer

<400> SEQUENCE: 12
aagtagcagg ccaacacgat                                                  20
```